(12) United States Patent
Lee et al.

(10) Patent No.: US 10,227,338 B2
(45) Date of Patent: Mar. 12, 2019

(54) SUBSTITUTED BENZENESULFONAMIDES AS SODIUM CHANNEL BLOCKERS

(71) Applicant: Daewoong Pharmaceutical Co., Ltd., Gyeonggi-do (KR)

(72) Inventors: Hyung-Geun Lee, Gyeonggi-do (KR); Il-Hwan Kim, Chungcheongbuk-do (KR); Myunggi Jung, Gyeonggi-do (KR); Hyo Shin Kim, Incheon (KR); Chun Ho Lee, Seoul (KR); Sun Ah Jun, Gyeonggi-do (KR); Ji Sung Yoon, Gyeonggi-do (KR); Sung-Young Kim, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/771,775

(22) PCT Filed: Nov. 11, 2016

(86) PCT No.: PCT/KR2016/013029
§ 371 (c)(1),
(2) Date: Apr. 27, 2018

(87) PCT Pub. No.: WO2017/082688
PCT Pub. Date: May 18, 2017

(65) Prior Publication Data
US 2018/0346459 A1    Dec. 6, 2018

(30) Foreign Application Priority Data

Nov. 13, 2015 (KR) .......................... 10-2015-0159637

(51) Int. Cl.
| | | |
|---|---|---|
| A61K 31/18 | (2006.01) |
| C07C 311/21 | (2006.01) |
| C07D 417/12 | (2006.01) |
| A61K 31/427 | (2006.01) |
| A61K 31/497 | (2006.01) |
| C07D 417/14 | (2006.01) |
| C07D 277/52 | (2006.01) |

(52) U.S. Cl.
CPC .......... *C07D 417/12* (2013.01); *A61K 31/427* (2013.01); *A61K 31/497* (2013.01); *C07D 277/52* (2013.01); *C07D 417/14* (2013.01)

(58) Field of Classification Search
CPC .............................. A61K 31/18; C07C 311/21
USPC ............................................. 514/604; 564/84
See application file for complete search history.

(56) References Cited

U.S. PATENT DOCUMENTS 5,464,853 A    11/1995 Chan et al.
8,153,814 B2    4/2012 Beaudoin et al.
(Continued)

FOREIGN PATENT DOCUMENTS

JP    2006290791 A    10/2006
KR    20110104558    9/2011
(Continued)

OTHER PUBLICATIONS

Fertleman et al., "SCN9A Mutations in Paroxysmal Extreme Pain Disorder: Allelic Variants Underlie Distinct Channel Defects and Phenotypes", Neuron 52, Dec. 7, 2006, pp. 767-774.
(Continued)

*Primary Examiner* — Douglas M Willis
(74) *Attorney, Agent, or Firm* — Marshall, Gerstein & Borun LLP

(57) ABSTRACT

The invention relates to a compound represented by Chemical Formula 1, below, a pharmaceutically acceptable salt thereof, and a pharmaceutical composition comprising the compound or salt. The compound of the invention or pharmaceutically acceptable salts thereof can be used for the prevention or treatment of sodium channel blocker-related diseases.

[Chemical Formula 1]

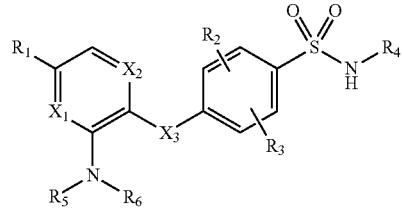

in Chemical Formula 1,
$R_1$ is hydrogen, $C_{1-4}$ alkyl, $C_{1-4}$ alkoxy, $C_{1-4}$ haloalkyl, $C_{1-4}$ haloalkoxy, halogen, or cyano,
$R_2$ and $R_3$ are each independently hydrogen, or halogen,
$R_4$ is $C_{5-10}$ heteroaryl containing one or two elements each independently selected from the group consisting of N, S and O, wherein the $C_{5-10}$ heteroaryl is unsubstituted or substituted with $C_{1-4}$ alkyl or halogen,
$R_5$ is $-CH_2CH_2-N(R_7)(R_8)$, or $-CH_2CH_2CH_2-N(R_7)(R_8)$, $R_6$ is hydrogen, or $C_{1-4}$ alkyl; or $R_5$ and $R_6$ together form $C_{3-5}$ alkylene, $(C_{2-4}$ alkylene)-$N(R_9)$—$(C_{2-4}$ alkylene), or $(C_{2-4}$ alkylene)-O—$(C_{2-4}$ alkylene), wherein the $C_{3-5}$ alkylene, or $C_{2-4}$ alkylene is each independently unsubstituted or substituted with one or two $R_{10}$,
$R_7$, $R_8$, and $R_9$ are each independently hydrogen, or $C_{1-4}$ alkyl,
$R_{10}$ is $C_{1-4}$ alkyl, $C_{1-4}$ alkoxy, halogen, amino, $NH(C_{1-4}$ alkyl), $N(C_{1-4}$ alkyl$)_2$, $NHCO(C_{1-4}$ alkyl), or pyrrolidinyl,
$X_1$ is C—R', or N, wherein R' is hydrogen, or halogen,
$X_2$ is CH, or N, and
$X_3$ is N—R", wherein R" is hydrogen, or $C_{1-4}$ alkyl.

22 Claims, No Drawings

(56) References Cited

U.S. PATENT DOCUMENTS

| 9,481,677 B2 | 11/2016 | Liu et al. |
| 2010/0197655 A1 | 8/2010 | Beaudoin et al. |
| 2012/0010183 A1 | 1/2012 | Bell et al. |
| 2012/0238579 A1 | 9/2012 | Besidki et al. |

FOREIGN PATENT DOCUMENTS

| KR | 20140105445 A | 9/2014 |
| WO | WO-2007/145922 A2 | 12/2007 |
| WO | WO-2009/012242 A2 | 1/2009 |
| WO | WO-2013/086229 A1 | 6/2013 |
| WO | WO-2013/088315 A1 | 6/2013 |
| WO | WO-2013/093688 A1 | 6/2013 |
| WO | WO-2013/177224 A1 | 11/2013 |

OTHER PUBLICATIONS

Cox et al., "An SCN9A Channelopathy Causes Congenital Inability to Experience Pain", Nature, vol. 444, Dec. 14, 2006, pp. 894-898.
Dib-Hajj et al., "From Genes to Pain: $Na_v1.7$ and Human Pain Disorders", Trends in Neurosciences vol. 30, No. 11, 2007, pp. 555-563.
Norinder et al., "QSAR Investigation of NaV1.7 Active Compounds Using the SVM/Signature Approach and the Bioclipse Modeling Platform", Bioorganic & Medicinal Chemistry Letters 23, 2013, pp. 261-263.
Written Opinion and Search Report in International Application No. PCT/KR2016/013029 dated Feb. 22, 2017, 16 pages.
Office Action in AU Application No. 2016351526 dated Oct. 10, 2018, 3 pages.
Office Action in NZ Application No. 742069 dated Aug. 23, 2018, 3 pages.
Notice of Opposition for Ecuador Patent Application No. IEPI-2018-38014, dated Dec. 3, 2018.

SUBSTITUTED BENZENESULFONAMIDES AS SODIUM CHANNEL BLOCKERS

BACKGROUND OF THE INVENTION

Field of the Invention

The present invention relates to a compound having sodium ion channel blocking activity, a process for preparing the same and use thereof.

Description of Related Art

Voltage-gated sodium (Nav) channels are found in all excitable cells, including muscle and nerve cells of the central and peripheral nervous systems. The sodium channels are essential for the initiation and propagation of electrical signals in the nervous system. Therefore, proper function of the sodium channels is essential to the normal function of the nerves. Ultimately, abnormal Nav channels play an important role in various diseases such as epilepsy, arrhythmia, myotonia, ataxia, multiple sclerosis, irritable bowel syndrome, urinary incontinence, visceral pain, depression, and pains. Currently, ten types of Nav channels are found in Human (Nav 1.1-1.9, Nax). Among them, four channels of Nav1.3, Nav1.7, Nav1.8 and Nav 1.9 are known to have a close connection with pain signaling, and thus are recognized as an important analgesic drug target.

A total of 10 types of Nav channels are found so far as summarized in Table 1 below. Among the 10 types, 9 types of Nav 1.1 to Nav1.9 form channels, among which NG 1.3, Nav 1.6, Nav 1.7, Nav 1.8 and Nav 1.9 are expressed in DRG.

TABLE 1

| Type | Gene | Distribution tissue | TTX IC-50 nM | Indications |
| --- | --- | --- | --- | --- |
| Nav1.1 | SCN1A | CNS/PNS | 10 | Pain, epilepsy, neurodegeneration |
| Nav1.2 | SCN2A | CNS | 10 | neurodegeneration, epilepsy |
| Nav1.3 | SCN3A | CNS | 15 | Pain, epilepsy |
| Nav1.4 | SCN4A | Sk. muscle | 25 | myotonia |
| Nav1.5 | SCN5A | Heart | 2000 | arrhythmia |
| Nav1.6 | SCN6A | CNS/PNS | 6 | pain, motor disorder |
| Nav1.7 | SCN7A | PNS | 25 | pain, neuroenedocrine disorder |
| Nav1.8 | SCN8A | PNS | 50000 | pain |
| Nav1.9 | SCN9A | PNS | 1000 | pain |

In particular, Nav1.7 is known to be preferentially expressed in dorsal root ganglia (DRG) and sympathetic ganglia. In the sensory ganglia DRG, Nav1.7 channel is expressed in A- or C-fiber neurons, but frequently distributed in small neurons having a deep connection with pain. In particular, 85% of DRG are present in cells defined as nociceptors. This fact indicates that Nav1.7 has a close connection with pain.

The fact that Nav1.7 channel has a close connection with pain is well demonstrated in the results of not only animal studies but also human disease studies. The results of animal studies indicated that, when inflammation occurs, the gene transcript of Nav1.7 significantly increases and the expression of proteins also increases. This increase in transcript is believed to be attributable to an increase in NGF. The increased expression of Nav1.7 is believed to be the direct cause of an increase in excitability of sensory cells. In particular, when the gene of the Nav1.7 channel is removed or reduced, inflammatory pain is greatly reduced. However, animal studies do not indicate that the removal or reduction of the Nav1.7 channel gene reduces neuropathic pain. However, there are many evidences that Nav1.7 is involved in neuropathic pain in humans.

Survey results for lineages that feel severe pain or no pain give many answers to pain studies. Particularly, these results directly indicate the importance of Nav1.7 in causing pain. There are two types of inherited diseases that cause severe pain. In the case of erythromelalgia or erythermalgia among these diseases, severe pain is sometimes felt for a few hours when the body is slightly warm or takes exercises. In some cases, the skin becomes red, and the hand, the foot or the face swell. The results of genetic research indicated that SCN9A (the human gene name of Nav1.7) is present at chromosomal sites associated with diseases. Nine mutations of Nav1.7 were found until now. These mutations lower activation threshold or result in slow deactivation of the channel. Thus, these mutations can easily generate action potential even upon depolarization of some neurons (see Dib-Hajj, S D. et al., Trends in Neurosci., 30, 555-563: (2007)).

In the case of paroxysmal extreme pain disorder (PEPD) that is another inherited disease, pain is felt through life and caused when the bowels are evacuated or the anal region is stimulated. In addition to pain, the leg becomes red. As is known in the art, in PEPD, eight mutations occur in Nav1.7. These mutations occur mainly in sites that cause inactivation. The Nav channel has an inactivation ball in the linker between domains III and IV, and a peptide receiving region in the linker between the S5 and S6 segments of domains III and IV. Interestingly, mutations that cause PEPD all occur in these two regions. It appears that these cause a problem in the inactivation of Nav1.7. As expected, these mutations cause a problem in the inactivation of Nav1.7, resulting in slow deactivation of the channel (see Fertleman, C. R. et al., Neuron, 52, 767-774 (2006)). Thus, the amount of electric current that enters through the channel increases.

Still another inherited disease is congenital indifference to pain (CIP). This disease results from mutation of the Nav1.7 channel and exist in Pakistani and Chinese lineages. Persons suffering from this disease feel no pain (see Cox, J. J. et al., Nature, 444, 894-898 (2006)). CIP causes the loss of function of the Nav1.7 channel. Particularly, a mutation in this channel inhibits the expression of this channel. Thus, this channel is not expressed (see Cox, J. J. et al., Nature, 444, 894-898 (2006)). Interestingly, the knock-out of Nav1.7 does not influence other sensations. However, it influences the olfactory sensation. This fact directly indicates that Nav1.7 does not overlap with other channels in pain transmission and the function thereof is not compensated for by other Nav channels.

As described above for the above diseases, when a mutation in the Nav1.7 channel causes a gain of function, severe pain is felt, and when it causes a loss of function, pain is relieved. This is a good clinical example that directly shows that the Nav1.7 channel is the major cause of pain. Thus, it is considered that an antagonist that inhibits this channel will naturally result in a pain-relieving effect.

However, if the Nav1.7 channel antagonist inhibits a plurality of Nav channels including the Nav1.7 channel, it can show adverse effects of various CNS disturbances, such as blurring of vision, dizziness, vomiting and depression. Particularly, if it inhibits the Nav1.5 channel, it can cause cardiac arrhythmia and heart failure, which threaten life. For these reasons, selective inhibition of the Nav1.7 channels is very important.

Pains can be largely classified into three: acute pain, inflammatory pain, and neuropathic pain. Acute pain plays an important protective function of maintaining the safety of organisms from stimuli that can cause tissue injury. Thus, it is generally temporary and intense. On the other hand, inflammatory pain can be longer lasting, and the intensity thereof further increases. Inflammatory pain is mediated by various substances that are released during inflammation, including substance P, histamine, acids, prostaglandin, bradykinin, CGRP, cytokines, ATP and other substances. The third pain is neuropathic and involves nerve injury or a nerve injury caused by viral infection. It causes reconstitution of circuits with neuron proteins to cause pathological "sensitization", which can result in chronic pain that is lasting for several years. This type of pain does not provide an advantage of adaptability and is difficult to treat by current therapy.

Particularly, neuropathic pain and intractable pain are great medical problems that have not been solved. Several hundred million patients are suffering from severe pain that is not well inhibited by current therapeutic methods. Drugs that are currently used for the treatment of pain include NSAIDS, COX-2 inhibitors, opioids, tricyclic antidepressants and anticonvulsants. Neuropathic pain is particularly difficult to treat, because it does not well respond to opioids until a high dose is reached. Currently, gabapentin is most widely used as a therapeutic agent against neuropathic pain, but it is effective for 60% of the patients and is not greatly effective. This drug is generally safe, but is problematic in terms of sedative action at high doses.

Accordingly, studies on the discovery of new regulators of the Nav1.7 channel and the use thereof for the treatment of acute pain, chronic acute, inflammatory pain and neuropathic pain have been actively conducted by global pharmaceutical companies, including Merck, AstraZeneca and the like (see US2010-0197655; US2012-0010183; WO2013-086229; WO2013-177224; US2012-0238579; WO2007-145922).

BRIEF SUMMARY OF THE INVENTION

In view of the above, as a result of studying novel compounds, the present inventors has found that a compound having a chemical structure different from sodium channel blockers reported so far not only has excellent sodium channel blocking effects, thereby completing the present invention. The compounds belonging to the present invention mainly have sodium channel inhibitory activity on their own, but do not exclude a possibility of exhibiting a pharmacological action as an efficacious agent by a special body environment or by products of metabolic process, after absorption into the body.

DETAILED DESCRIPTION OF THE INVENTION

Technical Problem

It is one object of the present invention to provide a compound having a blocking effect against sodium ion channels, particularly Nav 1.7, a process for its preparation and its use.

Technical Solution

In order to achieve the above objects, the present invention provides a compound represented by Chemical Formula 1 below, or a pharmaceutically acceptable salt thereof:

[Chemical Formula 1]

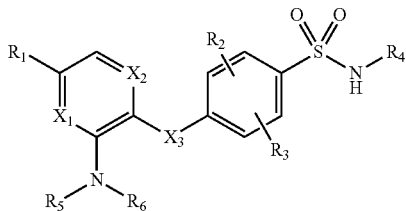

in Chemical Formula 1, $R_1$ is hydrogen, $C_{1-4}$ alkyl, $C_{1-4}$ alkoxy, $C_{1-4}$ haloalkyl, $C_{1-4}$ haloalkoxy, halogen, or cyano, $R_2$ and $R_3$ are each independently hydrogen, or halogen, $R_4$ is $C_{5-10}$ heteroaryl containing one or two elements each independently selected from the group consisting of N, S and O, wherein the $C_{5-10}$ heteroaryl is unsubstituted or substituted with $C_{1-4}$ alkyl or halogen, $R_5$ is —$CH_2CH_2$—$N(R_7)(R_8)$, or —$CH_2CH_2CH_2$—$N(R_7)(R_8)$, $R_6$ is hydrogen, or $C_{1-4}$ alkyl; or $R_5$ and $R_6$ together form $C_{3-5}$ alkylene, ($C_{2-4}$ alkylene)-$N(R_9)$—($C_{2-4}$ alkylene), or ($C_{2-4}$ alkylene)-O—($C_{2-4}$ alkylene), wherein the $C_{3-5}$ alkylene, or $C_{2-4}$ alkylene is each independently unsubstituted or substituted with one or two $R_{10}$, $R_7$, $R_8$, and $R_9$ are each independently hydrogen, or $C_{1-4}$ alkyl, $R_{10}$ is $C_{1-4}$ alkyl, $C_{1-4}$ alkoxy, halogen, amino, NH($C_{1-4}$ alkyl), N($C_{1-4}$ alkyl)$_2$, NHCO($C_{1-4}$ alkyl), or pyrrolidinyl, $X_1$ is C—R', or N, wherein R' is hydrogen, or halogen, $X_2$ is CH, or N, and $X_3$ is N—R", wherein R" is hydrogen, or $C_{1-4}$ alkyl.

Preferably, the compound represented by Chemical Formula 1 is represented by Chemical Formula 1' below:

[Chemical Formula 1']

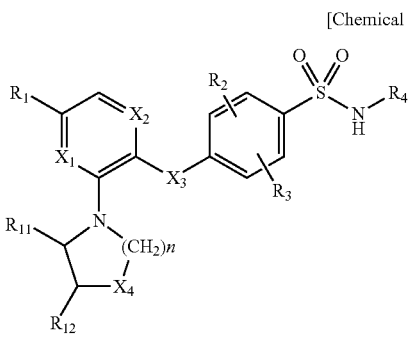

wherein, $R_1$ is hydrogen, $C_{1-4}$ alkyl, $C_{1-4}$ alkoxy, $C_{1-4}$ haloalkyl, $C_{1-4}$ haloalkoxy, halogen, or cyano, $R_2$ and $R_3$ are each independently hydrogen, or halogen, $R_4$ is $C_{5-10}$ heteroaryl containing one or two elements each independently selected from the group consisting of N, S and O, $R_{11}$ is hydrogen, or $C_{1-4}$ alkyl, $R_{12}$ is hydrogen, $C_{1-4}$ alkyl, $C_{1-4}$ alkoxy, halogen, amino, NH($C_{1-4}$ alkyl), N($C_{1-4}$ alkyl)$_2$, NHCO($C_{1-4}$ alkyl), or pyrrolidinyl, $X_1$ is C—R', or N, wherein R' is hydrogen, or halogen, $X_2$ is CH, or N, and $X_3$ is N—R″, wherein R″ is hydrogen, or $C_{1-4}$ alkyl,
$X_4$ is a bond, NH, N($C_{1-4}$ alkyl), or o (oxygen), and
n is an integer of 1 to 4.

Preferably, $R_1$ is hydrogen, methyl, methoxy, trifluoromethyl, difluoromethoxy, trifluoromethoxy, fluoro, chloro, or cyano.

Preferably, $R_2$ and $R_3$ are each independently hydrogen, fluoro, or chloro.

Preferably, $R_4$ is thiazolyl, isoxazolyl, oxazolyl, pyrazinyl, pyrazolyl, pyridinyl, pyrimidinyl, or thiadiazolyl, wherein the $R_4$ is unsubstituted or substituted with $C_{1-4}$ alkyl, or halogen.

Preferably, $R_5$ and $R_6$ together form $C_{3-5}$ alkylene, ($C_{2-4}$ alkylene)-N($R_9$)—($C_{2-4}$ alkylene), or ($C_{2-4}$ alkylene)-O—($C_{2-4}$ alkylene), wherein the $C_{3-5}$ alkylene or $C_{2-4}$ alkylene is each independently unsubstituted or substituted with methyl, methoxy, fluoro, amino, $NHCH_3$, $N(CH_3)_2$, $N(CH_2CH_3)_2$, $NHCOCH_3$, or pyrrolidinyl.

Preferably, $R_5$, $R_6$, and $R_5$ and $R_6$ together with the nitrogen to which they are attached form any one selected from the group consisting of:

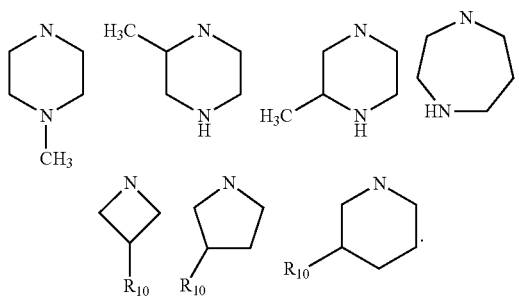

wherein, $R_{10}$ is as defined above.

Preferably, $R_5$ is —$CH_2CH_2$—NH—$CH_3$, —$CH_2CH_2CH_2$—NH—$CH_3$, or —$CH_2CH_2$—N($CH_3$)$_2$, and $R_6$ is hydrogen, or methyl.

Preferably, $X_1$ is CH, CF, or N, $X_2$ is CH, or N, provided that both $X_1$ and $X_2$ are not N.

Preferably, $X_3$ is NH.

Representative examples of the compound represented by Chemical Formula 1 or a pharmaceutically acceptable salt thereof are as follows:

1) 5-chloro-2-fluoro-4-((4-fluoro-2-(3-(methylamino)pyrrolidin-1-yl)phenyl)amino)-N-(thiazol-4-yl)benzenesulfonamide,
2) 5-chloro-4-((4-chloro-2-(3-(methylamino)pyrrolidin-1-yl)phenyl)amino)-2-fluoro-N-(thiazol-4-yl)benzenesulfonamide,
3) (R)-5-chloro-4-((4-chloro-2-(2-methylpiperazin-1-yl)phenyl)amino)-2-fluoro-N-(thiazol-4-yl)benzenesulfonamide,
4) (R)-5-chloro-4-((4-chloro-2-(3-(methylamino)piperidin-1-yl)phenyl)amino)-2-fluoro-N-(thiazol-4-yl)benzenesulfonamide,
5) (R)—N-(1-(5-chloro-2-((2-chloro-5-fluoro-4-(N-(thiazol-4-yl)sulfamoyl)phenyl)amino)phenyl)pyrrolidin-3-yl)acetamide,
6) 5-chloro-4-((4-chloro-2-(3-(diethylamino)pyrrolidin-1-yl)phenyl)amino)-2-fluoro-N-(thiazol-4-yl)benzenesulfonamide,
7) 4-((2-([1,3'-bipyrrolidin]-1'-yl)-4-chlorophenyl)amino)-5-chloro-2-fluoro-N-(thiazol-4-yl)benzenesulfonamide,
8) 5-chloro-2-fluoro-4-((4-methyl-2-(3-(methylamino)pyrrolidin-1-yl)phenyl)amino)-N-(thiazol-4-yl)benzenesulfonamide,
9) (S)-5-chloro-4-((4-chloro-2-(3-methylpiperazin-1-yl)phenyl)amino)-2-fluoro-N-(thiazol-4-yl)benzenesulfonamide,
10) 4-((4-fluoro-2-(3-(methylamino)pyrrolidin-1-yl)phenyl)amino)-N-(thiazol-4-yl)benzenesulfonamide,
11) 3-chloro-4-((4-fluoro-2-(3-(methylamino)pyrrolidin-1-yl)phenyl)amino)-N-(thiazol-4-yl)benzenesulfonamide,
12) 3,5-difluoro-4-((4-fluoro-2-(3-(methylamino)pyrrolidin-1-yl)phenyl)amino)-N-(thiazol-4-yl)benzenesulfonamide,
13) 2-fluoro-4-((4-fluoro-2-(3-(methylamino)pyrrolidin-1-yl)phenyl)amino)-N-(thiazol-4-yl)benzenesulfonamide,
14) 4-((2-(3-(methylamino)pyrrolidin-1-yl)-4-(trifluoromethoxy)phenyl)amino)-N-(thiazol-4-yl)benzenesulfonamide,
15) 3,5-difluoro-4-((2-(3-(methylamino)pyrrolidin-1-yl)-4-(trifluoromethoxy)phenyl)amino)-N-(thiazol-4-yl)benzenesulfonamide,
16) 2-fluoro-4-((2-(3-(methylamino)pyrrolidin-1-yl)-4-(trifluoromethoxy)phenyl)amino)-N-(thiazol-4-yl)benzenesulfonamide,
17) 5-chloro-2-fluoro-4-((2-(3-(methylamino)pyrrolidin-1-yl)-4-(trifluoromethoxy)phenyl)amino)-N-(thiazol-4-yl)benzenesulfonamide,
18) 5-chloro-4-((5-chloro-3-(3-(methylamino)pyrrolidin-1-yl)pyridin-2-yl)amino)-2-fluoro-N-(thiazol-4-yl)benzenesulfonamide,
19) 5-chloro-4-((6-chloro-2-(3-(methylamino)pyrrolidin-1-yl)pyridin-3-yl)amino)-2-fluoro-N-(thiazol-4-yl)benzenesulfonamide,
20) 5-chloro-2-fluoro-4-((2-(3-(methylamino)pyrrolidin-1-yl)-4-(trifluoromethyl)phenyl)amino)-N-(thiazol-4-yl)benzenesulfonamide,
21) 5-chloro-4-((4-(difluoromethoxy)-2-(3-(methylamino)pyrrolidin-1-yl)phenyl)amino)-2-fluoro-N-(thiazol-4-yl)benzenesulfonamide,
22) (R)-4-((4-fluoro-2-(3-(methylamino)piperidin-1-yl)phenyl)amino)-N-(thiazol-4-yl)benzenesulfonamide,
23) (R)-2-fluoro-4-((4-fluoro-2-(3-(methylamino)piperidin-1-yl)phenyl)amino)-N-(thiazol-4-yl)benzenesulfonamide,
24) (R)-3-chloro-4-((4-fluoro-2-(3-(methylamino)piperidin-1-yl)phenyl)amino)-N-(thiazol-4-yl)benzenesulfonamide,
25) (R)-3,5-difluoro-4-((4-fluoro-2-(3-(methylamino)piperidin-1-yl)phenyl)amino)-N-(thiazol-4-yl)benzenesulfonamide,
26) (R)-5-chloro-2-fluoro-4-((4-fluoro-2-(3-(methylamino)piperidin-1-yl)phenyl)amino)-N-(thiazol-4-yl)benzenesulfonamide,
27) (R)-4-((4-fluoro-2-(3-(methylamino)pyrrolidin-1-yl)phenyl)amino)-N-(thiazol-4-yl)benzenesulfonamide,
28) (R)-2-fluoro-4-((4-fluoro-2-(3-(methylamino)pyrrolidin-1-yl)phenyl)amino)-N-(thiazol-4-yl)benzenesulfonamide,
29) (R)-3-chloro-4-((4-fluoro-2-(3-(methylamino)pyrrolidin-1-yl)phenyl)amino)-N-(thiazol-4-yl)benzenesulfonamide,
30) (R)-3,5-difluoro-4-((4-fluoro-2-(3-(methylamino)pyrrolidin-1-yl)phenyl)amino)-N-(thiazol-4-yl)benzenesulfonamide,
31) (R)-5-chloro-2-fluoro-4-((4-fluoro-2-(3-(methylamino)pyrrolidin-1-yl)phenyl)amino)-N-(thiazol-4-yl)benzenesulfonamide, 32) 5-chloro-2-fluoro-4-((4-fluoro-2-(3-(methylamino)pyrrolidin-1-yl)phenyl)amino)-N-(thiazol-4-yl)benzenesulfonamide,
33) 4-((2-(3-aminopyrrolidin-1-yl)-4-fluorophenyl)amino)-2-fluoro-N-(thiazol-4-yl)benzenesulfonamide,
34) 4-((2-(3-aminopyrrolidin-1-yl)-4-fluorophenyl)amino)-3-chloro-N-(thiazol-4-yl)benzenesulfonamide,
35) 4-((2-(3-aminopyrrolidin-1-yl)-4-fluorophenyl)amino)-5-chloro-2-fluoro-N-(thiazol-4-yl)benzenesulfonamide,
36) 4-((2-(3-(methylamino)pyrrolidin-1-yl)phenyl)amino)-N-(thiazol-4-yl)benzenesulfonamide,
37) 2-fluoro-4-((2-(3-(methylamino)pyrrolidin-1-yl)-4-(trifluoromethyl)phenyl)amino)-N-(thiazol-4-yl)benzenesulfonamide,
38) 3-chloro-4-((2-(3-(methylamino)pyrrolidin-1-yl)-4-(trifluoromethyl)phenyl)amino)-N-(thiazol-4-yl)benzenesulfonamide,
39) 4-((4-(difluoromethoxy)-2-(3-(methylamino)pyrrolidin-1-yl)phenyl)amino)-2-fluoro-N-(thiazol-4-yl)benzenesulfonamide,
40) 3-chloro-4-((4-(difluoromethoxy)-2-(3-(methylamino)pyrrolidin-1-yl)phenyl)amino)-N-(thiazol-4-yl)benzenesulfonamide,
41) (R)-4-((4-fluoro-2-(3-fluoropyrrolidin-1-yl)phenyl)amino)-N-(thiazol-4-yl)benzenesulfonamide,
42) (R)-2-fluoro-4-((4-fluoro-2-(3-fluoropyrrolidin-1-yl)phenyl)amino)-N-(thiazol-4-yl)benzenesulfonamide,
43) (R)-3-chloro-4-((4-fluoro-2-(3-fluoropyrrolidin-1-yl)phenyl)amino)-N-(thiazol-4-yl)benzenesulfonamide,
44) (R)-3,5-difluoro-4-((4-fluoro-2-(3-fluoropyrrolidin-1-yl)phenyl)amino)-N-(thiazol-4-yl)benzenesulfonamide,
45) (R)-5-chloro-2-fluoro-4-((4-fluoro-2-(3-fluoropyrrolidin-1-yl)phenyl)amino)-N-(thiazol-4-yl)benzenesulfonamide,
46) 2-fluoro-4-((3-fluoro-2-(3-(methylamino)pyrrolidin-1-yl)phenyl)amino)-N-(thiazol-4-yl)benzenesulfonamide,
47) 3-chloro-4-((3-fluoro-2-(3-(methylamino)pyrrolidin-1-yl)phenyl)amino)-N-(thiazol-4-yl)benzenesulfonamide,
48) 5-chloro-2-fluoro-4-((3-fluoro-2-(3-(methylamino)pyrrolidin-1-yl)phenyl)amino)-N-(thiazol-4-yl)benzenesulfonamide,
49) 2-fluoro-4-((2-(3-(methylamino)pyrrolidin-1-yl)phenyl)amino)-N-(thiazol-4-yl)benzenesulfonamide,
50) 3-chloro-4-((2-(3-(methylamino)pyrrolidin-1-yl)phenyl)amino)-N-(thiazol-4-yl)benzenesulfonamide,
51) 3,5-difluoro-4-((2-(3-(methylamino)pyrrolidin-1-yl)phenyl)amino)-N-(thiazol-4-yl)benzenesulfonamide,
52) 5-chloro-2-fluoro-4-((2-(3-(methylamino)pyrrolidin-1-yl)phenyl)amino)-N-(thiazol-4-yl)benzenesulfonamide,
53) 2-fluoro-4-((4-methoxy-2-(3-(methylamino)pyrrolidin-1-yl)phenyl)amino)-N-(thiazol-4-yl)benzenesulfonamide,
54) 3-chloro-4-((4-methoxy-2-(3-(methylamino)pyrrolidin-1-yl)phenyl)amino)-N-(thiazol-4-yl)benzenesulfonamide,
55) 5-chloro-2-fluoro-4-((4-methoxy-2-(3-(methylamino)pyrrolidin-1-yl)phenyl)amino)-N-(thiazol-4-yl)benzenesulfonamide,
56) (R)-4-((4-methoxy-2-(3-(methylamino)piperidin-1-yl)phenyl)amino)-N-(thiazol-4-yl)benzenesulfonamide,
57) (R)-2-fluoro-4-((4-methoxy-2-(3-(methylamino)piperidin-1-yl)phenyl)amino)-N-(thiazol-4-yl)benzenesulfonamide,
58) (R)-3-chloro-4-((4-methoxy-2-(3-(methylamino)piperidin-1-yl)phenyl)amino)-N-(thiazol-4-yl)benzenesulfonamide,
59) (R)-3,5-difluoro-4-((4-methoxy-2-(3-(methylamino)piperidin-1-yl)phenyl)amino)-N-(thiazol-4-yl)benzenesulfonamide,
60) (R)-5-chloro-2-fluoro-4-((4-methoxy-2-(3-(methylamino)piperidin-1-yl)phenyl)amino)-N-(thiazol-4-yl)benzenesulfonamide,
61) 3-chloro-4-((4-fluoro-2-(4-methylpiperazin-1-yl)phenyl)amino)-N-(thiazol-4-yl)benzenesulfonamide,
62) 5-chloro-2-fluoro-4-((4-fluoro-2-(4-methylpiperazin-1-yl)phenyl)amino)-N-(thiazol-4-yl)benzenesulfonamide,
63) (S)-5-chloro-4-((2-(3-(dimethylamino)pyrrolidin-1-yl)-4-fluorophenyl)amino)-2-fluoro-N-(thiazol-4-yl)benzenesulfonamide,
64) (S)-5-chloro-4-((2-(3-(dimethylamino)pyrrolidin-1-yl)-4-(trifluoromethyl)phenyl)amino)-2-fluoro-N-(thiazol-4-yl)benzenesulfonamide,
65) 5-chloro-2-fluoro-4-((2-(4-methylpiperazin-1-yl)-4-(trifluoromethyl)phenyl)amino)-N-(thiazol-4-yl)benzenesulfonamide,
66) 5-chloro-4-((4-(difluoromethoxy)-2-(4-methylpiperazin-1-yl)phenyl)amino)-2-fluoro-N-(thiazol-4-yl)benzenesulfonamide,
67) 5-chloro-2-fluoro-4-((2-(4-methylpiperazin-1-yl)-4-(trifluoromethoxy)phenyl)amino)-N-(thiazol-4-yl)benzenesulfonamide,
68) (S)-3-chloro-4-((2-(3-(dimethylamino)pyrrolidin-1-yl)-4-(trifluoromethyl)phenyl)amino)-N-(thiazol-4-yl)benzenesulfonamide,
69) (S)-2-fluoro-4-((4-fluoro-2-(3-(methylamino)pyrrolidin-1-yl)phenyl)amino)-N-(thiazol-4-yl)benzenesulfonamide,
70) (S)-5-chloro-2-fluoro-4-((4-fluoro-2-(3-(methylamino)pyrrolidin-1-yl)phenyl)amino)-N-(thiazol-4-yl)benzenesulfonamide,
71) (S)-5-chloro-4-((2-(3-(dimethylamino)pyrrolidin-1-yl)-4-methoxyphenyl)amino)-2-fluoro-N-(thiazol-4-yl)benzenesulfonamide,
72) (S)-5-chloro-4-((4-(difluoromethoxy)-2-(3-(dimethylamino)pyrrolidin-1-yl)phenyl)amino)-2-fluoro-N-(thiazol-4-yl)benzenesulfonamide,
73) (R)-5-chloro-4-((2-(3-(dimethylamino)pyrrolidin-1-yl)-4-fluorophenyl)amino)-2-fluoro-N-(thiazol-4-yl)benzenesulfonamide,
74) (R)-5-chloro-4-((2-(3-(dimethylamino)pyrrolidin-1-yl)-4-(trifluoromethyl)phenyl)amino)-2-fluoro-N-(thiazol-4-yl)benzenesulfonamide,
75) (R)-5-chloro-4-((4-(difluoromethoxy)-2-(3-(dimethylamino)pyrrolidin-1-yl)phenyl)amino)-2-fluoro-N-(thiazol-4-yl)benzenesulfonamide,
76) 4-((2-(1,4-diazepan-1-yl)-4-fluorophenyl)amino)-5-chloro-2-fluoro-N-(thiazol-4-yl)benzenesulfonamide,
77) 5-chloro-4-((4-cyano-2-(3-(methylamino)pyrrolidin-1-yl)phenyl)amino)-2-fluoro-N-(thiazol-4-yl)benzenesulfonamide,
78) (R)—N-(1-(2-((2-chloro-5-fluoro-4-(N-(thiazol-4-yl)sulfamoyl)phenyl)amino)-5-(trifluoromethyl)phenyl)pyrrolidin-3-yl)acetamide,
79) (R)—N-(1-(2-((2-chloro-4-(N-(thiazol-4-yl)sulfamoyl)phenyl)amino)-5-(trifluoromethyl)phenyl)pyrrolidin-3-yl)acetamide,
80) (S)-3-chloro-4-((2-(3-(methylamino)pyrrolidin-1-yl)-4-(trifluoromethyl)phenyl)amino)-N-(thiazol-4-yl)benzenesulfonamide,
81) (S)-5-chloro-2-fluoro-4-((2-(3-(methylamino)pyrrolidin-1-yl)-4-(trifluoromethyl)phenyl)amino)-N-(thiazol-4-yl)benzenesulfonamide, 82) 5-chloro-2-fluoro-4-((4-fluoro-2-(3-(methylamino)azetidin-1-yl)phenyl)amino)-N-(thiazol-4-yl)benzenesulfonamide,
83) 4-((2-(3-aminoazetidin-1-yl)-4-fluorophenyl)amino)-5-chloro-2-fluoro-N-(thiazol-4-yl)benzenesulfonamide,
84) 5-chloro-4-((2-(3-(dimethylamino)azetidin-1-yl)-4-fluorophenyl)amino)-2-fluoro-N-(thiazol-4-yl)benzenesulfonamide,
85) N-(1-(2-((2-chloro-5-fluoro-4-(N-(thiazol-4-yl)sulfamoyl)phenyl)amino)-5-fluorophenyl)azetidin-3-yl)acetamide,
86) 5-chloro-2-fluoro-4-((4-fluoro-2-(3-methoxypyrrolidin-1-yl)phenyl)amino)-N-(thiazol-4-yl)benzenesulfonamide,
87) 5-chloro-2-fluoro-4-((2-(3-methoxypyrrolidin-1-yl)-4-(trifluoromethyl)phenyl)amino)-N-(thiazol-4-yl)benzenesulfonamide,
88) (R)—N-(1-(2-((2-chloro-5-fluoro-4-(N-(thiazol-4-yl)sulfamoyl)phenyl)amino)-5-fluorophenyl)pyrrolidin-3-yl)acetamide,
89) 3-chloro-4-((4-fluoro-2-(3-methoxypyrrolidin-1-yl)phenyl)amino)-N-(thiazol-4-yl)benzenesulfonamide,
90) 3-chloro-4-((2-(3-methoxypyrrolidin-1-yl)-4-(trifluoromethyl)phenyl)amino)-N-(thiazol-4-yl)benzenesulfonamide,
91) (R)—N-(1-(2-((2-chloro-4-(N-(thiazol-4-yl)sulfamoyl)phenyl)amino)-5-fluorophenyl)pyrrolidin-3-yl)acetamide,
92) 5-chloro-2-fluoro-4-((4-fluoro-2-(methyl(2-(methylamino)ethyl)amino)phenyl)amino)-N-(thiazol-4-yl)benzenesulfonamide,
93) 3-chloro-4-((2-((2-(dimethylamino)ethyl)(methyl)amino)-4-fluorophenyl)amino)-N-(thiazol-4-yl)benzenesulfonamide,
94) 5-chloro-4-((2-((2-(dimethylamino)ethyl)(methyl)amino)-4-fluorophenyl)amino)-2-fluoro-N-(thiazol-4-yl)benzenesulfonamide,
95) 5-chloro-2-fluoro-4-((2-(methyl(2-(methylamino)ethyl)amino)-4-(trifluoromethyl)phenyl)amino)-N-(thiazol-4-yl)benzenesulfonamide,
96) 5-chloro-2-fluoro-4-((4-fluoro-2-(methyl(2-(methylamino)ethyl)amino)phenyl)amino)-N-(5-fluoropyrimidin-2-yl)benzenesulfonamide,
97) 5-chloro-2-fluoro-N-(5-fluoropyrimidin-2-yl)-4-((2-(methyl(2-(methylamino)ethyl)amino)-4-(trifluoromethyl)phenyl)amino)benzenesulfonamide,
98) 5-chloro-4-((4-(difluoromethoxy)-2-(methyl(2-(methylamino)ethyl)amino)phenyl)amino)-2-fluoro-N-(thiazol-4-yl)benzenesulfonamide,
99) 5-chloro-4-((4-cyano-2-(methyl(2-(methylamino)ethyl)amino)phenyl)amino)-2-fluoro-N-(thiazol-4-yl)benzenesulfonamide,
100) 5-chloro-4-((4-cyano-2-(methyl(2-(methylamino)ethyl)amino)phenyl)amino)-2-fluoro-N-(5-fluoropyrimidin-2-yl)benzenesulfonamide,
101) 5-chloro-4-((4-(difluoromethoxy)-2-(methyl(2-(methylamino)ethyl)amino)phenyl)amino)-2-fluoro-N-(5-fluoropyrimidin-2-yl)benzenesulfonamide,
102) 5-chloro-2-fluoro-N-(5-fluoropyrimidin-2-yl)-4-((2-(methyl(2-(methylamino)ethyl)amino)phenyl)amino)benzenesulfonamide,
103) 5-chloro-2-fluoro-4-((4-fluoro-2-(methyl(2-(methylamino)ethyl)amino)phenyl)amino)-N-(5-fluoropyridin-2-yl)benzenesulfonamide,
104) 5-chloro-2-fluoro-4-((4-fluoro-2-(methyl(2-(methylamino)ethyl)amino)phenyl)amino)-N-(pyridin-2-yl)benzenesulfonamide,
105) 5-chloro-2-fluoro-4-((4-fluoro-2-(methyl(2-(methylamino)ethyl)amino)phenyl)amino)-N-(thiazol-2-yl)benzenesulfonamide,
106) 5-chloro-4-((4-cyano-2-(methyl(2-(methylamino)ethyl)amino)phenyl)amino)-2-fluoro-N-(5-fluoropyridin-2-yl)benzenesulfonamide,
107) 5-chloro-4-((4-cyano-2-(methyl(2-(methylamino)ethyl)amino)phenyl)amino)-2-fluoro-N-(pyridin-2-yl)benzenesulfonamide,
108) 5-chloro-4-((4-cyano-2-(methyl(2-(methylamino)ethyl)amino)phenyl)amino)-2-fluoro-N-(thiazol-2-yl)benzenesulfonamide,
109) 5-chloro-2-fluoro-N-(5-fluoropyridin-2-yl)-4-((2-(methyl(2-(methylamino)ethyl)amino)-4-(trifluoromethyl)phenyl)amino)benzenesulfonamide,
110) 5-chloro-2-fluoro-4-((2-(methyl(2-(methylamino)ethyl)amino)-4-(trifluoromethyl)phenyl)amino)-N-(pyridin-2-yl)benzenesulfonamide,
111) 5-chloro-2-fluoro-4-((2-(methyl(2-(methylamino)ethyl)amino)-4-(trifluoromethyl)phenyl)amino)-N-(thiazol-2-yl)benzenesulfonamide,
112) 5-chloro-2-fluoro-N-(5-fluoropyridin-2-yl)-4-((2-(methyl(2-(methylamino)ethyl)amino)phenyl)amino)benzenesulfonamide,
113) 5-chloro-2-fluoro-4-((2-(methyl(2-(methylamino)ethyl)amino)phenyl)amino)-N-(pyridin-2-yl)benzenesulfonamide,
114) 5-chloro-2-fluoro-4-((2-(methyl(2-(methylamino)ethyl)amino)phenyl)amino)-N-(thiazol-2-yl)benzenesulfonamide,
115) 5-chloro-4-((4-(difluoromethoxy)-2-(methyl(2-(methylamino)ethyl)amino)phenyl)amino)-2-fluoro-N-(5-fluoropyridin-2-yl)benzenesulfonamide,
116) 5-chloro-4-((4-(difluoromethoxy)-2-(methyl(2-(methylamino)ethyl)amino)phenyl)amino)-2-fluoro-N-(thiazol-2-yl)benzenesulfonamide,
117) 5-chloro-4-((4-(difluoromethoxy)-2-(methyl(2-(methylamino)ethyl)amino)phenyl)amino)-2-fluoro-N-(pyridin-2-yl)benzenesulfonamide,
118) 5-chloro-2-fluoro-N-(5-fluoropyridin-2-yl)-4-((4-methoxy-2-(methyl(2-(methylamino)ethyl)amino)phenyl)amino)benzenesulfonamide,
119) 5-chloro-2-fluoro-4-((4-methoxy-2-(methyl(2-(methylamino)ethyl)amino)phenyl)amino)-N-(thiazol-2-yl)benzenesulfonamide,
120) 5-chloro-2-fluoro-4-((4-methoxy-2-(methyl(2-(methylamino)ethyl)amino)phenyl)amino)-N-(thiazol-4-yl)benzenesulfonamide,
121) 5-chloro-2-fluoro-4-((2-(methyl(2-(methylamino)ethyl)amino)phenyl)amino)-N-(thiazol-4-yl)benzenesulfonamide,
122) 5-chloro-2-fluoro-N-(5-fluoropyrimidin-2-yl)-4-((4-methoxy-2-(methyl(2-(methylamino)ethyl)amino)phenyl)amino)benzenesulfonamide,
123) 5-chloro-4-((4-chloro-2-(methyl(2-(methylamino)ethyl)amino)phenyl)amino)-2-fluoro-N-(thiazol-4-yl)benzenesulfonamide,
124) 5-chloro-4-((4-chloro-2-(methyl(2-(methylamino)ethyl)amino)phenyl)amino)-2-fluoro-N-(5-fluoropyrimidin-2-yl)benzenesulfonamide,
125) 5-chloro-4-((4-chloro-2-(methyl(2-(methylamino)ethyl)amino)phenyl)amino)-2-fluoro-N-(5-fluoropyridin-2-yl)benzenesulfonamide,
126) 5-chloro-4-((4-chloro-2-(methyl(2-(methylamino)ethyl)amino)phenyl)amino)-2-fluoro-N-(thiazol-2-yl)benzenesulfonamide,
127) 5-chloro-N-(5-chlorothiazol-2-yl)-2-fluoro-4-((4-fluoro-2-(methyl(2-(methylamino)ethyl)amino)phenyl)amino)benzenesulfonamide,
128) 5-chloro-2-fluoro-4-((4-fluoro-2-(methyl(2-(methylamino)ethyl)amino)phenyl)amino)-N-(5-fluorothiazol-2-yl)benzenesulfonamide, 129) 5-chloro-N-(5-chlorothiazol-2-yl)-2-fluoro-4-((2-(methyl(2-(methylamino)ethyl)amino)phenyl)amino)benzenesulfonamide,
130) 5-chloro-N-(5-chlorothiazol-2-yl)-2-fluoro-4-((4-methoxy-2-(methyl(2-(methylamino)ethyl)amino)phenyl)amino)benzenesulfonamide,
131) 5-chloro-2-fluoro-N-(5-fluorothiazol-2-yl)-4-((2-(methyl(2-(methylamino)ethyl)amino)phenyl)amino)benzenesulfonamide,
132) 5-chloro-2-fluoro-N-(5-fluorothiazol-2-yl)-4-((4-methoxy-2-(methyl(2-(methylamino)ethyl)amino)phenyl)amino)benzenesulfonamide,
133) 5-chloro-2-fluoro-4-((4-fluoro-2-(methyl(2-(methylamino)ethyl)amino)phenyl)amino)-N-(5-methylisoxazol-3-yl)benzenesulfonamide,
134) 5-chloro-2-fluoro-4-((2-(methyl(2-(methylamino)ethyl)amino)phenyl)amino)-N-(5-methylisoxazol-3-yl)benzenesulfonamide,
135) 5-chloro-2-fluoro-4-((4-fluoro-2-(methyl(2-(methylamino)ethyl)amino)phenyl)amino)-N-(5-methyl-1H-pyrazol-3-yl)benzenesulfonamide,
136) 5-chloro-2-fluoro-4-((2-(methyl(2-(methylamino)ethyl)amino)phenyl)amino)-N-(5-methyl-1H-pyrazol-3-yl)benzenesulfonamide,
137) 5-chloro-4-((2-((2-(dimethylamino)ethyl)(methyl)amino)-4-fluorophenyl)amino)-2-fluoro-N-(5-fluoropyridin-2-yl)benzenesulfonamide,
138) 5-chloro-4-((2-((2-(dimethylamino)ethyl)(methyl)amino)-4-fluorophenyl)amino)-2-fluoro-N-(thiazol-2-yl)benzenesulfonamide,
139) 5-chloro-N-(5-chlorothiazol-2-yl)-4-((2-((2-(dimethylamino)ethyl)(methyl)amino)-4-fluorophenyl)amino)-2-fluorobenzenesulfonamide,
140) 5-chloro-N-(5-chlorothiazol-2-yl)-4-((2-((2-(dimethylamino)ethyl)(methyl)amino)phenyl)amino)-2-fluorobenzenesulfonamide,
141) 5-chloro-2-fluoro-4-((4-fluoro-2-(methyl(2-(methylamino)ethyl)amino)phenyl)amino)-N-(5-methylthiazol-2-yl)benzenesulfonamide,
142) 5-chloro-2-fluoro-4-((4-fluoro-2-(methyl(2-(methylamino)ethyl)amino)phenyl)amino)-N-(oxazol-2-yl)benzenesulfonamide,
143) N-(5-(tert-butyl)isoxazol-3-yl)-5-chloro-2-fluoro-4-((4-fluoro-2-(methyl(2-(methylamino)ethyl)amino)phenyl)amino)benzenesulfonamide,
144) N-(5-(tert-butyl)isoxazol-3-yl)-5-chloro-2-fluoro-4-((2-(methyl(2-(methylamino)ethyl)amino)phenyl)amino)benzenesulfonamide,
145) 5-chloro-2-fluoro-4-((4-fluoro-2-(3-(methylamino)pyrrolidin-1-yl)phenyl)amino)-N-(1,2,4-thiadiazol-5-yl)benzenesulfonamide,
146) 5-chloro-2-fluoro-4-((4-fluoro-2-(3-(methylamino)pyrrolidin-1-yl)phenyl)amino)-N-(1-methyl-1H-pyrazol-3-yl)benzenesulfonamide,
147) 5-chloro-2-fluoro-4-((4-fluoro-2-(3-(methylamino)pyrrolidin-1-yl)phenyl)amino)-N-(pyrimidin-4-yl)benzenesulfonamide,
148) 5-chloro-2-fluoro-4-((4-fluoro-2-(3-(methylamino)pyrrolidin-1-yl)phenyl)amino)-N-(5-fluoropyrimidin-2-yl)benzenesulfonamide,
149) 5-chloro-2-fluoro-4-((4-fluoro-2-(3-(methylamino)pyrrolidin-1-yl)phenyl)amino)-N-(pyrazin-2-yl)benzenesulfonamide,
150) 5-chloro-2-fluoro-4-((4-fluoro-2-(3-(methylamino)pyrrolidin-1-yl)phenyl)amino)-N-(5-methylisoxazol-3-yl)benzenesulfonamide,
151) 5-chloro-2-fluoro-4-((4-fluoro-2-(3-(methylamino)pyrrolidin-1-yl)phenyl)amino)-N-(pyrimidin-5-yl)benzenesulfonamide,
152) 5-chloro-2-fluoro-4-((4-fluoro-2-((2-(methylamino)ethyl)amino)phenyl)amino)-N-(thiazol-4-yl)benzenesulfonamide,
153) 5-chloro-4-((2-((2-(dimethylamino)ethyl)amino)-4-fluorophenyl)amino)-2-fluoro-N-(thiazol-4-yl)benzenesulfonamide, and
154) 5-chloro-2-fluoro-4-((4-fluoro-2-(methyl(3-(methylamino)propyl)amino)phenyl)amino)-N-(thiazol-4-yl)benzenesulfonamide.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

As the free acid, an organic acid and an inorganic acid can be used. Examples of the inorganic acids include hydrochloric acid, phosphoric acid, sulfuric acid, nitric acid, tartaric acid and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto.

In addition, a pharmaceutically acceptable metal salt can be obtained by a conventional method using a base. For example, a compound represented by Chemical Formula 1 is dissolved in an excessive amount of an alkali metal hydroxide or an alkaline earth metal hydroxide solution, the non-soluble salt is filtered, and the filtrate is evaporated and dried to obtain a pharmaceutically acceptable metal salt. At this time, it is particularly preferable to prepare a sodium salt, a potassium salt or a calcium salt as the metal salt.

A pharmaceutically unacceptable salt or solvate of the compound of Chemical Formula 1 may be used as an intermediate when preparing the compound of Chemical Formula 1, or the pharmaceutically acceptable salt or the solvate thereof.

Further, the compound of Chemical Formula 1 according to the present invention includes not only pharmaceutically acceptable salts thereof, but also solvates such as hydrates that can be prepared therefrom, and includes all possible stereoisomers, but are not limited thereto. The solvate and the stereoisomer of the compound of Chemical Formula 1 may be prepared from the compound of Chemical Formula 1 using common methods known in the art.

In addition, the compound of Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

Furthermore, as an example, the present invention can produce the compound represented by Chemical Formula 1 through Reaction Scheme 1 below.

[Reaction Scheme 1]

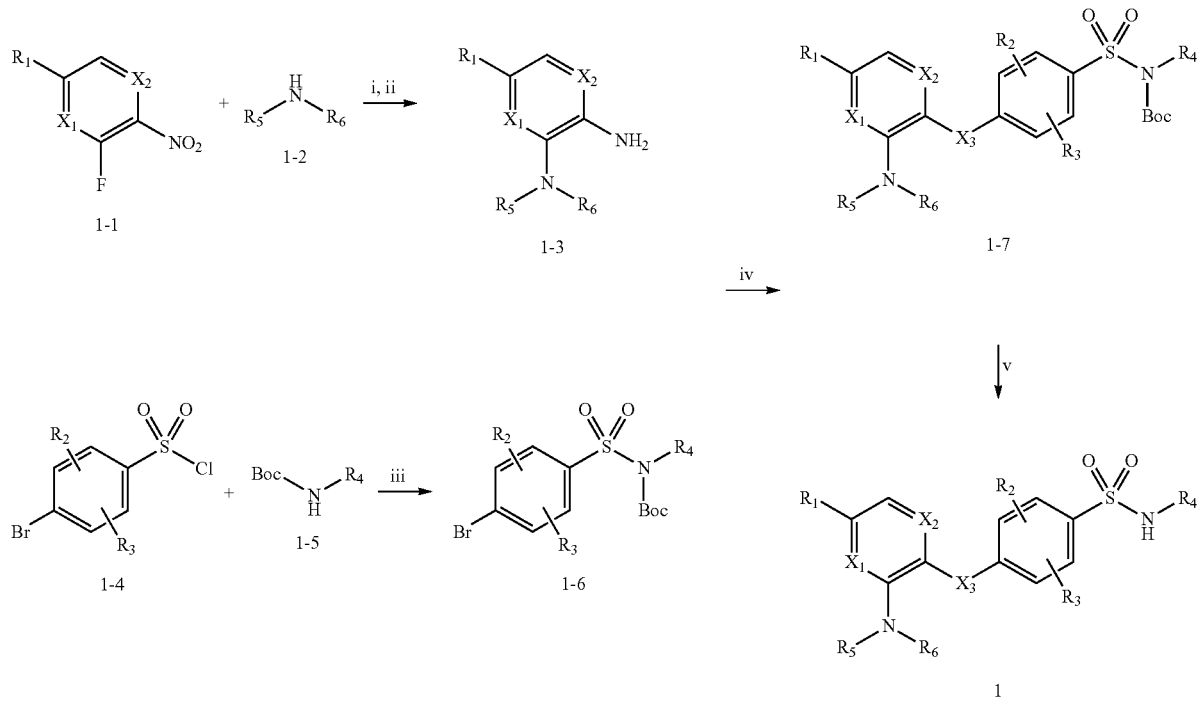

in Reaction Scheme 1, $X_1$ to $X_4$, $R_1$ to $R_6$, and n are as previously defined in Chemical Formula 1.

According to the steps i, ii and iii, the respective compounds represented by Chemical Formulas 1-3 and 1-6 can be prepared as intermediates. The step i is preferably reacted at 50 to 60° C. in the presence of potassium carbonate, and the solvent is preferably dimethylformamide. The step ii is preferably carried out at 50 to 60° C. in the presence of sodium hyposulfite, and as the solvent, a mixed solvent of ethanol and water (1:1) is preferably used. The step iii is preferably carried out at −78° C. in the presence of lithium hexamethyldisilylamide, and the solvent is preferably tetrahydrofuran.

The intermediate represented by Chemical Formula 1-7 can be prepared according to the step iv. The above step is a step of reacting the compound represented by Chemical Formula 1-3 with the compound represented by Chemical Formula 1-6. The reaction is preferably carried out at 120° C. in the presence of palladium diacetate, bis(diphenylphosphino)binaphthyl and cesium carbonate, and the solvent is preferably dioxane.

The compound represented by Chemical Formula 1 can be obtained according to the step v. The reaction is preferably carried out at 60 to 80° C. in the presence of hydrochloric acid, and the solvent is preferably methanol. Also, depending on the type of substituent of $R_1$ to $R_6$, if it is necessary to protect in the reaction of the steps i to iv, the steps i to iv may be carried out in a state of being protected with a protective group, which can be then removed in the step v.

Further, the present invention provides a pharmaceutical composition for preventing or treating diseases, which is effective for sodium channel blocking activity, comprising the compound represented by Chemical Formula 1, or a pharmaceutically acceptable salt, hydrate, solvate or isomer thereof as an active ingredient.

In this case, the disease includes acute pain, chronic pain, neuropathic pain, postoperative pain, migraine, arthralgia, neuropathy, nerve damage, diabetic neuropathy, neuropathic disease, epilepsy, arrhythmia, myotonia, ataxia, multiple sclerosis, irritable bowel syndrome, urinary incontinence, visceral pain, depression, erythralgia, PEPD (paroxysmal extreme pain disorder) or the like.

As used herein, the term "prevention" refers to any act to delay or inhibit occurrence, spread or recurrence of the above-mentioned diseases by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the Pharmaceutical composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof can be usefully used for the prevention or treatment of sodium channel blocker-related diseases.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1: Preparation of 5-chloro-2-fluoro-4-((4-fluoro-2-(3-(methylamino)pyrrolidin-1-yl)phenyl) amino)-N-(thiazol-4-yl)benzenesulfonamide hydrochloride

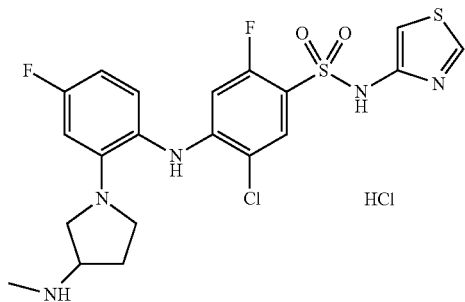 [SMILES: CNC1CCN(c2cc(F)ccc2Nc2cc(F)c(S(=O)(=O)Nc3cscn3)cc2Cl)C1 ; Cl]

Step 1) Preparation of tert-butyl(1-(2-amino-5-fluorophenyl)pyrrolidin-3-yl)(methyl)carbamate 2,4-difluoro-1-nitrobenzene (2.0 g, 12.6 mmol) and tert-butylmethyl(pyrrolidin-3-yl)carbamate (2.5 g, 1.0 eq.) were dissolved in DMF (20 mL), and then $K_2CO_3$ (2.6 g, 1.5 eq.) was added thereto. While maintaining the internal temperature at 60 to 70° C., the reaction mixture was stirred for 2 hours. When the reaction solution became dark yellow, the completion of the reaction was confirmed by TLC. After cooling to room temperature, ethyl acetate (EA)/$H_2O$ was added and stirred, and then the layers were separated. $MgSO_4$ was added to the separated organic layer, which was stirred, dried and then filtered. The filtrate was concentrated under reduced pressure, and the residue was dissolved in EtOH (10 mL) and distilled water (10 mL), to which $Na_2S_2O_4$ (13.0 g, 6 eq.) was added. While maintaining the internal temperature at 60 to 70° C., the reaction mixture was stirred for 2 hours. When the yellow color of the reaction solution faded and became almost colorless, the completion of the reaction was confirmed by TLC. After cooling to room temperature, distilled water (50 mL) was added and extracted twice with EA (100 mL). $MgSO_4$ was added to the organic layer, which was stirred, dried and then filtered. The filtrate was concentrated under reduced pressure, and the resulting residue was separated by column chromatography (n-Hexane/EA=3/1) to obtain the title compound (2.0 g, 51.1%).

1H NMR (MeOD): 6.73 (m, 1H), 6.57 (t, 1H), 3.23 (m, 1H), 3.10 (m, 2H), 2.94 (m, 1H), 2.91 (s, 3H), 2.25 (m, 1H), 1.99 (m, 1H)

Step 2) Preparation of tert-butyl thiazol-4-yl carbamate

Thiazol-4-carboxylic acid (5.0 g, 38.8 mmol) was dissolved in t-BuOH (100 mL), and then TEA (8.1 mL, 1.5 eq.) and DPPA (7.1 mL, 1.5 eq.) were added thereto. While maintaining the internal temperature at 90 to 100° C., the reaction mixture was stirred for 3 days, and then the completion of the reaction was confirmed by TLC. The product was concentrated under reduced pressure, distilled water (50 mL) was added, and extracted twice with EA (100 mL). $MgSO_4$ was added to the organic layer, which was stirred, dried and then filtered. The filtrate was concentrated under reduced pressure, and the residue was added to a small amount of EA and slurried. The resulting solid was filtered to obtain a white title compound (4.0 g, 51.5%).

1H NMR (MeOD): 8.73 (s, 1H), 7.24 (s, 1H), 1.52 (s, 9H)

Step 3) Preparation of tert-butyl((4-bromo-5-chloro-2-fluorophenyl)sulfonyl)(thiazol-4-yl)carbamate Tert-butyl thiazol-4-yl carbamate (4.0 g, 20.0 mmol) prepared in the step 2) was added to a reaction vessel and the inside of the vessel was replaced with nitrogen gas. After dissolving in THF (32 mL), the solution was cooled to −78° C. using dry ice-acetone. After cooling, LiHMDS (22.4 mL, 1.5 eq.) was slowly added and the reaction mixture was stirred for 30 minutes. 4-Bromo-5-chloro-2-fluorobenzenesulfonyl chloride (6.0 g, 1.0 eq.) was dissolved in THF (10 mL) and then slowly added to the reaction solution. The reaction mixture was stirred overnight and the completion of the reaction was confirmed by TLC. Distilled water (50 mL) was added and extracted twice with EA (100 mL). $MgSO_4$ was added to the organic layer, which was stirred, dried and then filtered. The filtrate was concentrated under reduced pressure, and the residue was crystallized with THF/n-Hexane to obtain the title compound (4.4 g, 59.0%).

1H NMR (MeOD): 9.00 (s, 1H), 8.22 (d, 1H), 7.90 (d, 1H), 7.78 (s, 1H), 1.35 (s, 9H)

Step 4) Preparation of tert-butyl(1-(2-((4-(N-(tert-butoxycarbonyl)-N-(thiazol-4-yl)sulfamoyl)-2-chloro-5-fluorophenyl)amino)-5-fluorophenyl)pyrrolidin-3-yl)(methyl)carbamate Tert-butyl (1-(2-amino-5-fluorophenyl)pyrrolidin-3-yl)(methyl)carbamate (0.5 g, 1.1 mmol) prepared in the step 1)

and tert-butyl ((4-bromo-5-chloro-2-fluorophenyl)sulfonyl)(thiazol-4-yl)carbamate (0.9 g, 1.2 eq.) prepared in the step 3) were dissolved in 1,4-dioxane (10 mL). Pd(OAc)$_2$ (0.03 g, 0.1 eq), rac-BINAP (0.19 g, 0.2 eq.) and Cs$_2$CO$_3$ (1.5 g, 3.0 eq.) were added to the reaction solution. After reacting at 120° C. for 30 minutes using a microwave initiator, the completion of the reaction was confirmed by TLC. Distilled water (50 mL) was added and extracted twice with EA (100 mL). MgSO$_4$ was added to the organic layer, which was stirred, filtered and then dried. The filtrate was concentrated under reduced pressure, and the residue was separated by column chromatography (EA/n-Hexane=1/1). This procedure was repeated twice to obtain the title compound (2.0 g, 88.2%).

1H NMR (MeOD): 8.95 (s, 1H), 7.94 (d, 1H), 7.65 (s, 1H), 7.14 (t, 1H), 6.70 (d, 1H), 6.64 (t, 1H), 6.07 (d, 1H), 3.40 (m, 1H), 3.28 (m, 2H), 3.16 (m, 1H), 2.64 (s, 3H), 2.06 (m, 1H), 1.89 (m, 1H), 1.41 (s, 9H), 1.36 (s, 9H)

Step 5) Preparation of 5-chloro-2-fluoro-4-((4-fluoro-2-(3-(methylamino)pyrrolidin-1-yl)phenyl)amino)-N-(thiazol-4-yl)benzenesulfonamide hydrochloride To tert-butyl (1-(2-((4-(N-(tert-butoxycarbonyl)-N-(thiazol-4-yl)sulfamoyl)-2-chloro-5-fluorophenyl)amino)-5-fluorophenyl)pyrrolidin-3-yl)(methyl)carbamate (2.0 g, 2.9 mmol) prepared in the step 4) was added 1.25 M HCl in MeOH (15 mL). After stirring the mixture overnight while heating to 40 to 50° C., the completion of the reaction was confirmed by TLC. The product was concentrated, methylene chloride (15 mL) was added to the obtained residue, stirred for 1 hour, and the produced solid was filtered to give the title compound (0.9 g, 58.8%).

1H NMR (MeOD): 8.73 (s, 1H), 7.75 (d, 1H), 7.12 (t, 1H), 7.00 (s, 1H), 6.69 (d, 1H), 6.67 (t, 1H), 6.05 (d, 1H), 3.73 (m, 1H), 3.54 (m, 1H), 3.45 (m, 1H), 3.38 (m, 1H), 3.26 (m, 1H), 2.63 (s, 3H), 2.31 (m, 1H), 1.96 (m, 1H)

Hereinafter, the compounds of Examples 2 to 9 were prepared in the same manner as described in Example 1, except that the reactants corresponding to the structures of the compounds to be produced were used.

Example 2: Preparation of 5-chloro-4-((4-chloro-2-(3-(methylamino)pyrrolidin-1-yl)phenyl)amino)-2-fluoro-N-(thiazol-4-yl)benzenesulfonamide hydrochloride

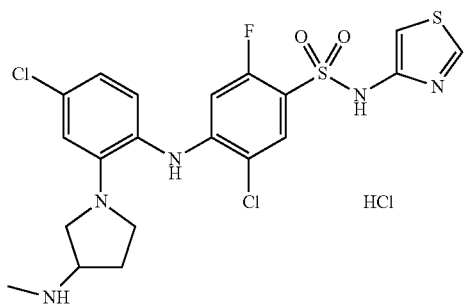 [SMILES: CNC1CCN(c2cc(Cl)ccc2Nc2cc(F)c(S(=O)(=O)Nc3cscn3)cc2Cl)C1 ; Cl]

1H NMR (500 MHz, MeOD): 8.79 (s, 1H), 7.74 (d, 1H), 7.09 (d, 1H), 7.02 (s, 1H), 6.98 (s, 1H), 6.92 (d, 1H), 6.13 (d, 1H), 3.76 (m, 1H), 3.53 (m, 3H), 2.64 (s, 3H), 2.31 (m, 1H), 2.01 (m, 1H), 1.27 (m, 1H)

Example 3: Preparation of (R)-5-chloro-4-((4-chloro-2-(2-methylpiperazin-1-yl)phenyl)amino)-2-fluoro-N-(thiazol-4-yl)benzenesulfonamide hydrochloride

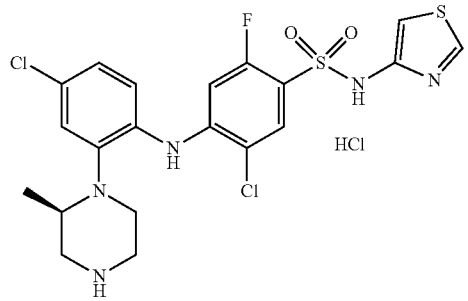 [SMILES: C[C@@H]1CNCCN1c1cc(Cl)ccc1Nc1cc(F)c(S(=O)(=O)Nc2cscn2)cc1Cl ; Cl]

1H NMR (500 MHz, MeOD): 8.73 (d, 1H), 7.84 (d, 1H), 7.38 (d, 1H), 7.30 (d, 1H), 7.28 (d, 1H), 7.04 (d, 1H), 6.99 (d, 1H), 3.40 (m, 3H), 3.15 (m, 2H), 3.07 (m, 1H), 2.86 (m, 1H), 0.93 (m, 3H)

Example 4: Preparation of (R)-5-chloro-4-((4-chloro-2-(3-(methylamino)piperidin-1-yl)phenyl)amino)-2-fluoro-N-(thiazol-4-yl)benzenesulfonamide hydrochloride

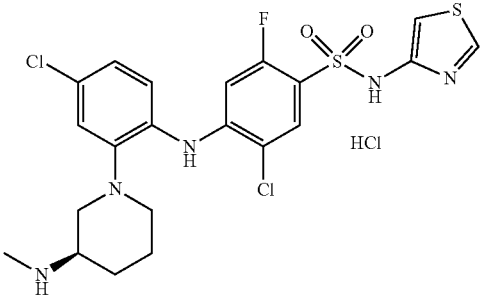 [SMILES: CN[C@@H]1CCCN(c2cc(Cl)ccc2Nc2cc(F)c(S(=O)(=O)Nc3cscn3)cc2Cl)C1 ; Cl]

1H NMR (500 MHz, MeOD): 8.75 (d, 1H), 7.80 (d, 1H), 7.28 (d, 1H), 7.20 (d, 1H), 7.17 (m, 1H), 7.03 (d, 1H), 6.58 (d, 1H), 3.44 (m, 1H), 3.02 (m, 1H), 2.94 (m, 1H), 2.78 (m, 1H), 2.67 (s, 3H), 2.08 (m, 1H), 1.79 (m, 1H), 1.50 (m, 1H), 1.41 (m, 1H), 0.87 (m, 1H)

Example 5: Preparation of (R)—N-(1-(5-chloro-2-((2-chloro-5-fluoro-4-(N-(thiazol-4-yl)sulfamoyl)phenyl)amino)phenyl)pyrrolidin-3-yl)acetamide hydrochloride

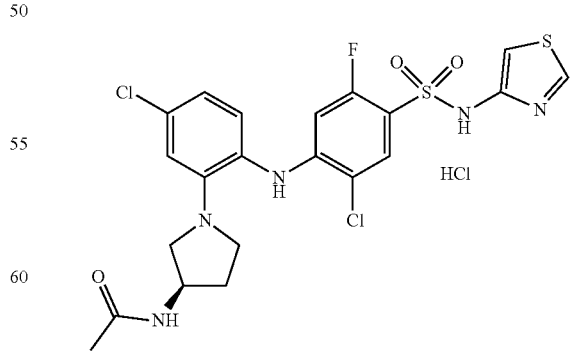

1H NMR (500 MHz, MeOD): 8.78 (m, 1H), 7.76 (d, 1H), 7.17 (d, 1H), 7.08 (m, 1H), 7.02 (s, 1H), 6.92 (m, 1H), 6.15 (t, 1H), 4.26 (m, 1H), 3.55 (m, 1H), 3.35 (m, 1H), 3.25 (m, 1H), 2.27 (m, 1H), 1.93 (m, 1H), 1.90 (s, 3H)

Example 6: Preparation of 5-chloro-4-((4-chloro-2-(3-(diethylamino)pyrrolidin-1-yl)phenyl)amino)-2-fluoro-N-(thiazol-4-yl)benzenesulfonamide hydrochloride

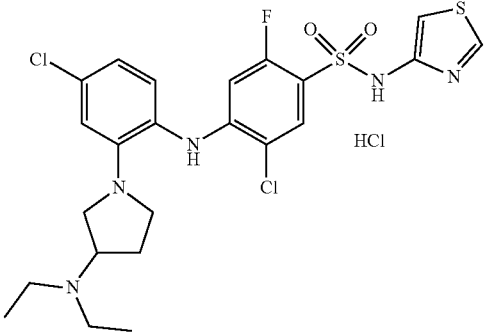 [SMILES: CCN(CC)C1CCN(c2cc(Cl)ccc2Nc2cc(F)c(S(=O)(=O)Nc3cscn3)cc2Cl)C1 ; Cl]

1H NMR (500 MHz, MeOD): 8.78 (d, 1H), 7.77 (d, 1H), 7.12 (d, 1H), 7.03 (m, 1H), 6.99 (dd, 1H), 6.03 (d, 1H), 4.08 (m, 1H), 3.52 (m, 3H), 3.17 (m, 4H), 3.05 (m, 1H), 2.39 (m, 1H), 2.01 (m, 1H), 1.26 (m, 6H)

Example 7: Preparation of 4-((2-([1,3'-bipyrrolidin]-1'-yl)-4-chlorophenyl)amino)-5-chloro-2-fluoro-N-(thiazol-4-yl)benzenesulfonamide hydrochloride

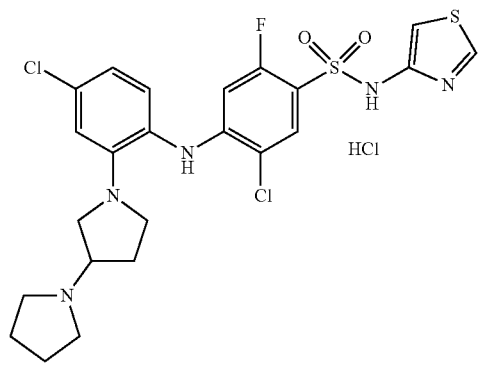 [SMILES: O=S(=O)(Nc1cscn1)c1cc(Cl)c(Nc2ccc(Cl)cc2N2CCC(N3CCCC3)C2)cc1F ; Cl]

1H NMR (500 MHz, MeOD): 8.76 (d, 1H), 7.77 (d, 1H), 7.11 (d, 1H), 7.02 (m, 2H), 6.97 (m, 1H), 6.07 (d, 1H), 3.91 (m, 1H), 3.50 (m, 5H), 3.22 (m, 1H), 3.05 (m, 2H), 2.36 (m, 1H), 1.97 (m, 5H)

Example 8: Preparation of 5-chloro-2-fluoro-4-((4-methyl-2-(3-(methylamino)pyrrolidin-1-yl)phenyl)amino)-N-(thiazol-4-yl)benzenesulfonamide hydrochloride

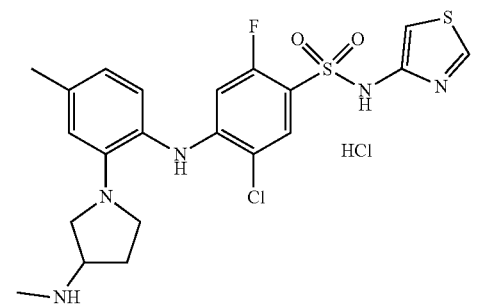 [SMILES: CNC1CCN(c2cc(C)ccc2Nc2cc(F)c(S(=O)(=O)Nc3cscn3)cc2Cl)C1 ; Cl]

1H NMR (500 MHz, MeOD): 8.76 (d, 1H), 7.74 (d, 1H), 7.02 (m, 2H), 6.91 (s, 1H), 6.85 (d, 1H), 6.16 (d, 1H), 3.78 (m, 1H), 3.45 (m, 3H), 3.23 (m, 1H), 2.65 (s, 3H), 2.35 (s, 3H), 2.34 (m, 1H), 2.01 (m, 1H)

Example 9: Preparation of (S)-5-chloro-4-((4-chloro-2-(3-methylpiperazin-1-yl)phenyl)amino)-2-fluoro-N-(thiazol-4-yl)benzenesulfonamide hydrochloride

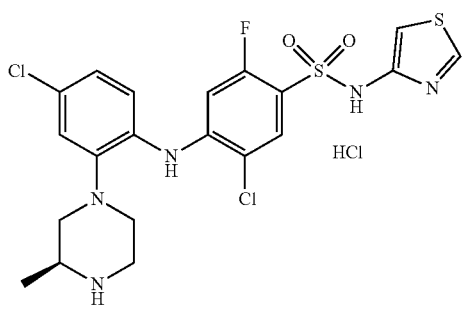 [SMILES: C[C@H]1CN(c2cc(Cl)ccc2Nc2cc(F)c(S(=O)(=O)Nc3cscn3)cc2Cl)CCN1 ; Cl]

1H NMR (500 MHz, MeOD): 8.73 (d, 1H), 7.79 (d, 1H), 7.29 (d, 1H), 7.20 (m, 2H), 7.03 (d, 1H), 6.54 (d, 1H), 3.88 (m, 1H), 3.44 (s, 3H), 3.04 (m, 1H), 2.97 (m, 1H), 2.80 (m, 1H), 1.27 (m, 3H)

Example 10: Preparation of 4-((4-fluoro-2-(3-(methylamino)pyrrolidin-1-yl)phenyl)amino)-N-(thiazol-4-yl)benzenesulfonamide

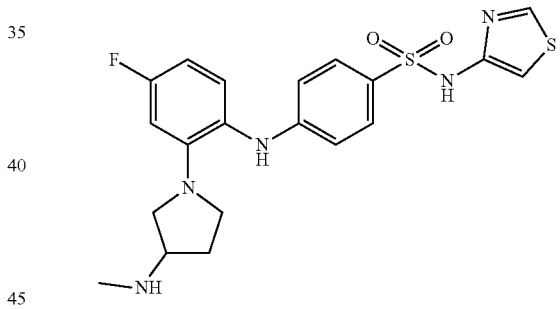

Intermediate tert-butyl (1-(2-((4-(N-(tert-butoxycarbonyl)-N-(thiazole-4-yl)sulfamoyl)phenyl)amino)-5-fluorophenyl)pyrrolidin-3-yl)(methyl)carbamate was prepared in the same manner as described in the steps 1 to 4 of Example 1, except that 4-bromobenzenesulfonyl chloride was used instead of 4-bromo-5-chloro-2-fluorobenzenesulfonyl chloride in the step 3 of Example 1.

To the obtained intermediate was added 1.25 M HCl in MeOH (15 mL). After stirring the mixture overnight while heating to 40 to 50° C., the completion of the reaction was confirmed by TLC. The product was concentrated, and the obtained residue was separated and purified by PLC to obtain 0.05 g of the target compound (yield: 48%).

1H NMR (500 MHz, MeOD): 8.68 (s, 1H), 7.57 (d, 2H), 7.07 (t, 1H), 6.92 (s, 1H), 6.66-6.54 (m, 4H), 3.42-3.30 (m, 4H), 3.14-3.13 (m, 1H), 2.42 (s, 3H), 2.18-2.16 (m, 1H), 1.84-1.40 (m, 1H)

Hereinafter, the compounds of Examples 11 to 91 were prepared in the same manner as described in Example 10, except that the reactants corresponding to the structures of the compounds to be produced were used.

Example 11: Preparation of 3-chloro-4-((4-fluoro-2-(3-(methylamino)pyrrolidin-1-yl)phenyl)amino)-N-(thiazol-4-yl)benzenesulfonamide

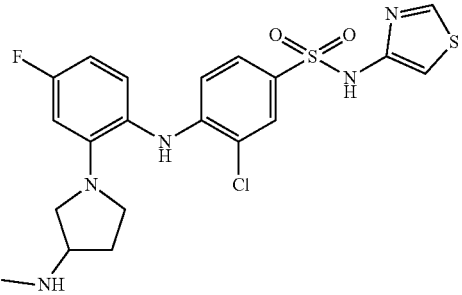 [SMILES: CNC1CCN(c2cc(F)ccc2Nc2ccc(S(=O)(=O)Nc3cscn3)cc2Cl)C1]

1H NMR (500 MHz, MeOD): 8.69 (s, 1H), 7.74 (s, 1H), 7.47 (d, 1H), 7.05 (t, 1H), 6.93 (s, 1H), 6.63 (d, 1H), 6.54 (t, 1H), 6.33 (d, 1H), 3.40-3.37 (m, 2H), 3.17-3.11 (m, 3H), 2.31 (s, 3H), 2.08-2.00 (m, 1H), 1.72-1.68 (m, 1H)

Example 12: Preparation of 3,5-difluoro-4-((4-fluoro-2-(3-(methylamino)pyrrolidin-1-yl)phenyl)amino)-N-(thiazol-4-yl)benzenesulfonamide

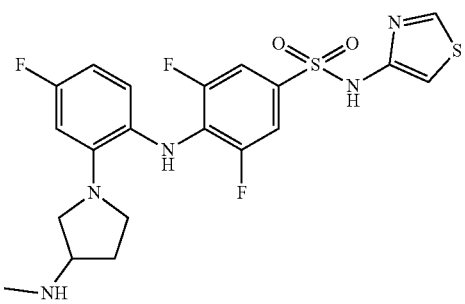 [SMILES: CNC1CCN(c2cc(F)ccc2Nc2c(F)cc(S(=O)(=O)Nc3cscn3)cc2F)C1]

1H NMR (500 MHz, MeOD): 8.73 (s, 1H), 7.43 (d, 2H), 7.04 (s, 1H), 6.63 (t, 1H), 6.75 (d, 1H), 6.60 (t, 1H), 3.66-3.63 (m, 1H), 3.49-3.35 (m, 3H), 3.08-3.04 (m, 1H), 2.63 (s, 3H), 2.31-2.28 (m, 1H), 1.96-1.93 (m, 1H)

Example 13: Preparation of 2-fluoro-4-((4-fluoro-2-(3-(methylamino)pyrrolidin-1-yl)phenyl)amino)-N-(thiazol-4-yl)benzenesulfonamide

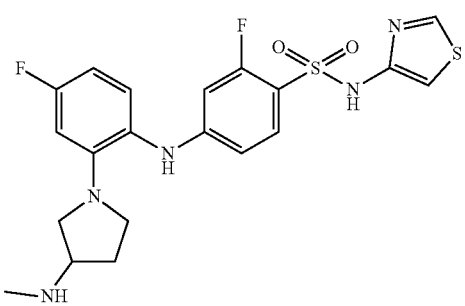 [SMILES: CNC1CCN(c2cc(F)ccc2Nc2ccc(S(=O)(=O)Nc3cscn3)c(F)c2)C1]

1H NMR (500 MHz, MeOD): 8.68 (s, 1H), 7.56 (t, 1H), 7.03 (t, 1H), 6.84 (s, 1H), 6.63 (d, 1H), 6.55 (t, 1H), 6.40 (d, 1H), 6.23 (d, 1H), 3.35-3.30 (m, 3H), 3.18-3.16 (m, 2H), 2.36 (s, 3H), 2.11-2.05 (m, 1H), 1.78-1.75 (m, 1H)

Example 14: Preparation of 4-((2-(3-(methylamino)pyrrolidin-1-yl)-4-(trifluoromethoxy)phenyl)amino)-N-(thiazol-4-yl)benzenesulfonamide

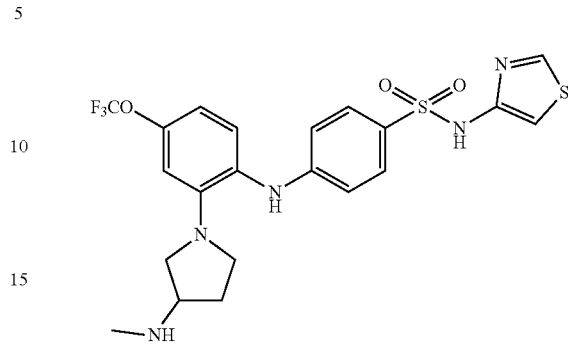

1H NMR (500 MHz, MeOD): 8.68 (s, 1H), 7.60 (d, 2H), 7.16 (d, 1H), 6.92 (s, 1H), 6.77-6.68 (m, 4H), 3.38-3.61 (m, 1H), 3.35-3.33 (m, 2H), 3.28-3.27 (m 1H), 3.09-3.06 (m, 1H), 2.36 (s, 3H), 2.36-2.35 (m, 1H), 1.85-1.83 (m, 1H)

Example 15: Preparation of 3,5-difluoro-4-((2-(3-(methylamino)pyrrolidin-1-yl)-4-(trifluoromethoxy)phenyl)amino)-N-(thiazol-4-yl)benzenesulfonamide

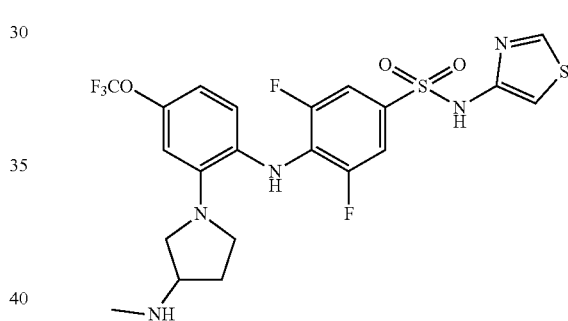

1H NMR (500 MHz, MeOD): 8.62 (s, 1H), 7.41 (d, 2H), 6.87 (s, 1H), 6.76-6.75 (m, 1H), 6.69-6.67 (m, 2H), 3.59 (s, 1H), 3.49-3.47 (m, 2H), 3.25-3.23 (m, 1H), 2.99-2.98 (m, 1H), 2.59 (s, 3H), 2.29-2.27 (m, 1H), 1.99-1.97 (m, 1H)

Example 16: Preparation of 2-fluoro-4-((2-(3-(methylamino)pyrrolidin-1-yl)-4-(trifluoromethoxy)phenyl)amino)-N-(thiazol-4-yl)benzenesulfonamide

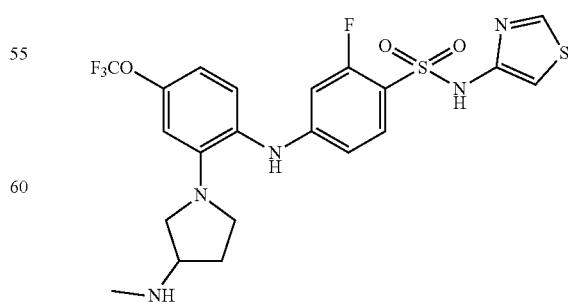

1H NMR (500 MHz, MeOD): 8.68 (s, 1H), 7.58 (t, 1H), 7.16 (d, 1H), 6.84 (s, 1H), 6.84-6.83 (m, 2H), 6.49 (d, 1H), 6.35 (d, 1H), 3.38-3.34 (m, 3H), 3.23-3.21 (m, 1H), 3.12-3.10 (m, 1H), 2.41 (s, 3H), 2.18-2.16 (m, 1H), 1.85-1.83 (m, 1H)

Example 17: Preparation of 5-chloro-2-fluoro-4-((2-(3-(methylamino)pyrrolidin-1-yl)-4-(trifluoromethoxy)phenyl)amino)-N-(thiazol-4-yl)benzenesulfonamide

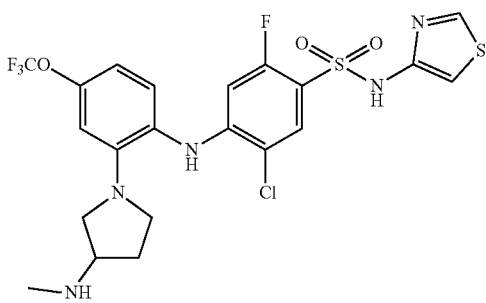 [SMILES: CNC1CCN(c2cc(OC(F)(F)F)ccc2Nc2cc(F)c(S(=O)(=O)Nc3cscn3)cc2Cl)C1]

1H NMR (500 MHz, MeOD): 8.68 (s, 1H), 7.74 (d, 1H), 7.15 (d, 1H), 6.85 (s, 1H), 6.75-6.74 (m, 2H), 6.04 (d, 1H), 3.45-3.38 (m, 3H), 3.19-3.17 (m, 2H), 2.40 (s, 3H), 2.13-2.12 (m, 1H), 1.80-1.79 (m, 1H)

Example 18: Preparation of 5-chloro-4-((5-chloro-3-(3-(methylamino)pyrrolidin-1-yl)pyridin-2-yl)amino)-2-fluoro-N-(thiazol-4-yl)benzenesulfonamide

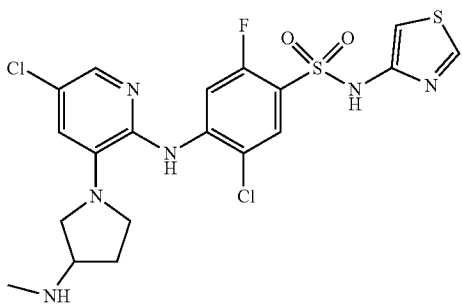 [SMILES: CNC1CCN(c2cc(Cl)cnc2Nc2cc(F)c(S(=O)(=O)Nc3cscn3)cc2Cl)C1]

1H NMR (500 MHz, MeOD): 8.68 (d, 1H), 8.30 (d, 1H), 7.96 (d, 1H), 7.84 (d, 1H), 7.53 (d, 1H), 6.87 (d, 1H), 3.44 (m, 3H), 3.10 (m, 2H), 2.50 (s, 3H), 2.36 (m, 1H), 1.95 (m, 1H)

Example 19: Preparation of 5-chloro-4-((6-chloro-2-(3-(methylamino)pyrrolidin-1-yl)pyridin-3-yl)amino)-2-fluoro-N-(thiazol-4-yl)benzenesulfonamide

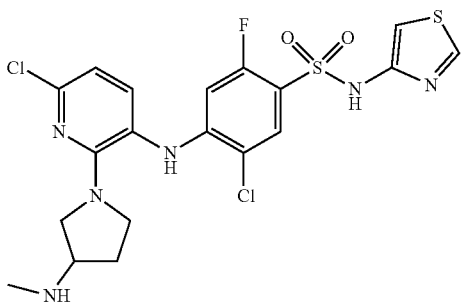 [SMILES: CNC1CCN(c2nc(Cl)ccc2Nc2cc(F)c(S(=O)(=O)Nc3cscn3)cc2Cl)C1]

1H NMR (500 MHz, MeOD): 8.69 (s, 1H), 7.76 (s, 1H), 7.34 (s, 1H), 6.90 (m, 2H), 6.70 (s, 1H), 6.01 (d, 1H), 3.45 (m, 3H), 2.99 (m, 2H), 2.49 (s, 3H), 2.11 (m, 2H)

Example 20: Preparation of 5-chloro-2-fluoro-4-((2-(3-(methylamino)pyrrolidin-1-yl)-4-(trifluoromethyl)phenyl)amino)-N-(thiazol-4-yl)benzenesulfonamide

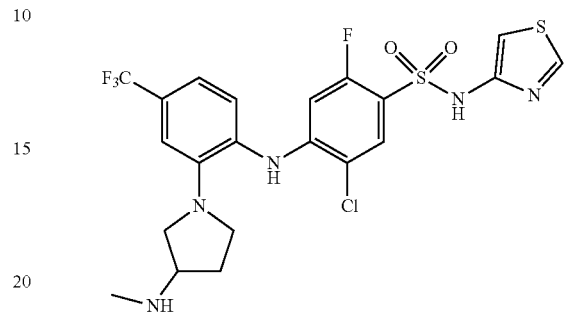

1H NMR (500 MHz, MeOD): 8.67 (d, 1H), 7.78 (d, 1H), 7.26 (d, 1H), 7.16 (m, 2H), 6.81 (d, 1H), 6.21 (d, 1H), 3.39 (m, 3H), 3.17 (m, 2H), 2.43 (s, 3H), 2.13 (m, 1H), 1.94 (m, 1H)

Example 21: Preparation of 5-chloro-4-((4-(difluoromethoxy)-2-(3-(methylamino)pyrrolidin-1-yl)phenyl)amino)-2-fluoro-N-(thiazol-4-yl)benzenesulfonamide

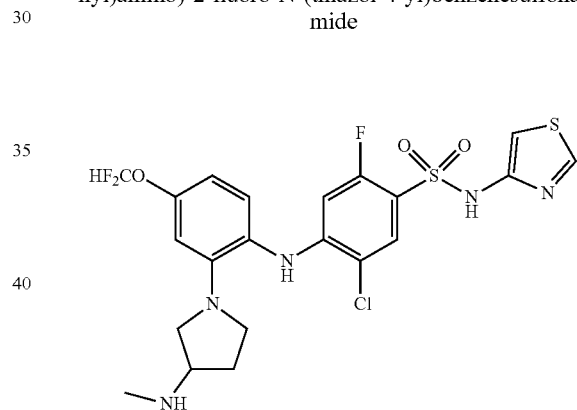

1H NMR (500 MHz, MeOD): 8.63 (d, 1H), 7.73 (d, 1H), 7.07 (d, 1H), 6.70 (t, 2H), 6.62 (t, 2H), 6.03 (d, 1H), 3.40 (m, 3H), 3.23 (m, 2H), 2.42 (s, 3H), 2.11 (m, 1H), 1.83 (m, 1H)

Example 22: Preparation of (R)-4-((4-fluoro-2-(3-(methylamino)piperidin-1-yl)phenyl)amino)-N-(thiazol-4-yl)benzenesulfonamide

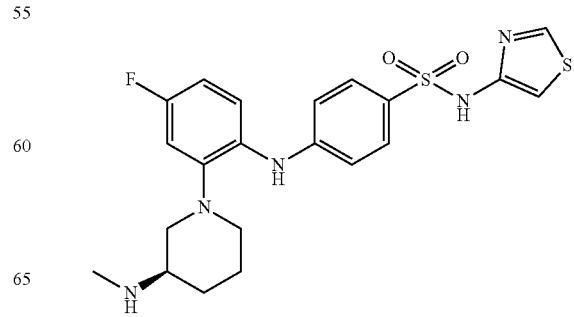

1H NMR (500 MHz, MeOD): 8.68 (s, 1H), 7.61 (d, 2H), 7.17 (t, 1H), 6.89 (s, 1H), 6.77-6.75 (m, 3H), 6.74-6.73 (m, 1H), 3.34-3.30 (m, 1H), 2.88-2.59 (m, 4H), 2.32 (s, 3H), 1.82-1.70 (m, 2H), 1.45-1.44 (m, 2H)

Example 23: Preparation of (R)-2-fluoro-4-((4-fluoro-2-(3-(methylamino)piperidin-1-yl)phenyl)amino)-N-(thiazol-4-yl)benzenesulfonamide

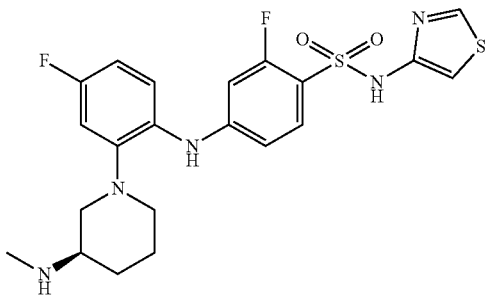 [SMILES: CN[C@@H]1CCCN(c2cc(F)ccc2Nc2ccc(S(=O)(=O)Nc3cscn3)c(F)c2)C1]

1H NMR (500 MHz, MeOD): 8.68 (s, 1H), 7.61 (t, 1H), 7.20 (t, 1H), 6.87 (d, 1H), 6.85-6.81 (m, 2H), 6.78 (d, 1H), 6.67 (d, 1H), 3.34 (s, 1H), 2.92-2.79 (m, 4H), 2.48 (s, 3H), 1.89-1.87 (m, 2H), 1.79-1.78 (m, 1H), 1.47-1.46 (m, 1H)

Example 24: Preparation of (R)-3-chloro-4-((4-fluoro-2-(3-(methylamino)piperidin-1-yl)phenyl)amino)-N-(thiazol-4-yl)benzenesulfonamide

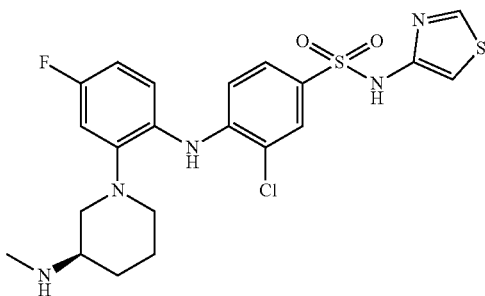 [SMILES: CN[C@@H]1CCCN(c2cc(F)ccc2Nc2ccc(S(=O)(=O)Nc3cscn3)cc2Cl)C1]

1H NMR (500 MHz, MeOD): 8.69 (s, 1H), 7.80 (s, 1H), 7.54 (s, 1H), 7.24-7.21 (m, 1H), 6.89-6.77 (m, 4H), 3.01-2.97 (m, 1H), 2.68-2.41 (m, 3H), 2.30 (s, 3H), 1.86-1.84 (m, 1H), 1.68-1.66 (m, 1H), 1.40-1.35 (m, 2H)

Example 25: Preparation of (R)-3,5-difluoro-4-((4-fluoro-2-(3-(methylamino)piperidin-1-yl)phenyl)amino)-N-(thiazol-4-yl)benzenesulfonamide

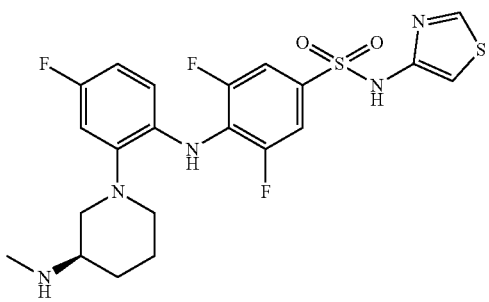 [SMILES: CN[C@@H]1CCCN(c2cc(F)ccc2Nc2c(F)cc(S(=O)(=O)Nc3cscn3)cc2F)C1]

1H NMR (500 MHz, MeOD): 8.64 (s, 1H), 7.41 (d, 2H), 6.85 (d, 1H), 6.75-6.66 (m, 3H), 3.26-3.24 (m, 1H), 2.88-2.78 (m, 4H), 2.55 (s, 3H), 1.87-1.86 (m, 1H) 1.85-1.83 (m, 1H), 1.74-1.72 (m, 1H), 1.37-1.35 (m, 1H)

Example 26: Preparation of (R)-5-chloro-2-fluoro-4-((4-fluoro-2-(3-(methylamino)piperidin-1-yl)phenyl)amino)-N-(thiazol-4-yl)benzenesulfonamide

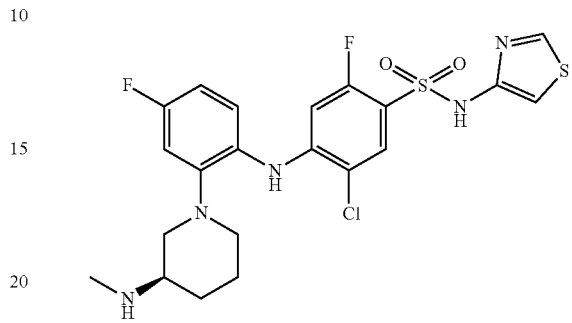

1H NMR (500 MHz, MeOD): 8.66 (s, 1H), 7.77 (d, 1H), 7.22 (t, 1H), 6.89-6.84 (m, 2H), 6.81 (s, 1H), 6.35 (d, 1H), 3.38-3.36 (m, 1H), 3.03-3.01 (m, 1H), 2.63-2.61 (m, 1H), 2.48-2.44 (m, 2H), 2.37 (s, 3H), 1.89-1.87 (m, 1H), 1.68-1.66 (m, 1H), 1.32-1.32 (m, 2H)

Example 27: Preparation of (R)-4-((4-fluoro-2-(3-(methylamino)pyrrolidin-1-yl)phenyl)amino)-N-(thiazol-4-yl)benzenesulfonamide

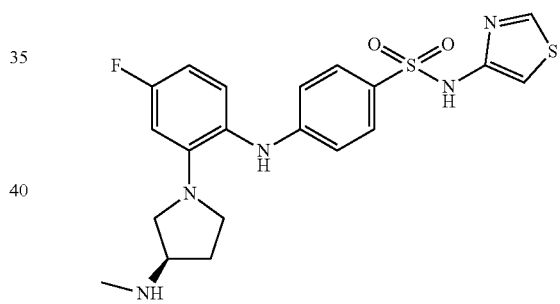

1H NMR (500 MHz, MeOD): 8.68 (s, 1H), 7.56 (d, 2H), 7.04 (t, 1H), 6.92 (s, 1H), 6.63-6.53 (m, 4H), 3.24-3.21 (m, 3H), 3.14-3.10 (m, 2H), 2.31 (s, 3H), 2.11-2.08 (m, 1H), 1.73-1.70 (m, 1H)

Example 28: Preparation of (R)-2-fluoro-4-((4-fluoro-2-(3-(methylamino)pyrrolidin-1-yl)phenyl)amino)-N-(thiazol-4-yl)benzenesulfonamide

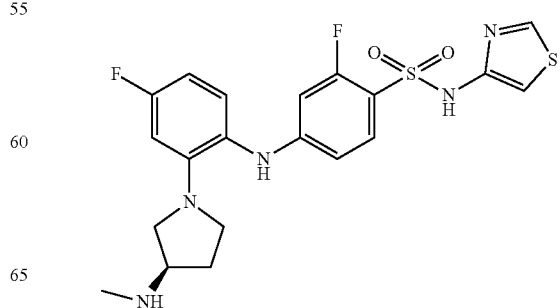

1H NMR (500 MHz, MeOD): 8.68 (s, 1H), 7.57-7.53 (m, 1H), 7.05-7.03 (m, 1H), 6.83 (s, 1H), 6.62 (d, 1H), 6.55-6.53 (m, 1H), 6.40 (d, 1H), 6.23 (d, 1H), 3.34-3.30 (m, 2H), 3.28-3.27 (m, 1H), 3.18-3.15 (m, 2H), 2.36 (s, 3H), 2.13-2.10 (m, 1H), 1.76-1.74 (m, 1H)

Example 29: Preparation of (R)-3-chloro-4-((4-fluoro-2-(3-(methylamino)pyrrolidin-1-yl)phenyl)amino)-N-(thiazol-4-yl)benzenesulfonamide

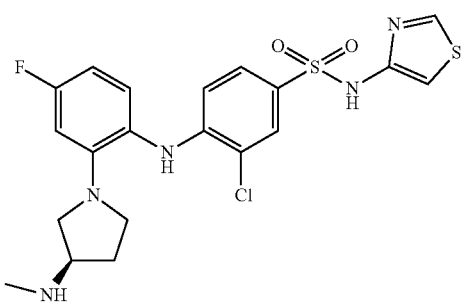 [SMILES: CN[C@@H]1CCN(c2cc(F)ccc2Nc2ccc(S(=O)(=O)Nc3cscn3)cc2Cl)C1]

1H NMR (500 MHz, MeOD): 8.68 (s, 1H), 7.75 (s, 1H), 7.47-7.45 (m, 1H), 7.06-7.04 (m, 1H), 6.92 (s, 1H), 6.62 (d, 1H), 6.54 (d, 1H), 6.32 (d, 1H), 3.40-3.37 (m, 2H), 3.17-3.11 (m, 3H), 2.33 (s, 3H), 2.08-2.05 (m, 1H), 1.72-1.69 (m, 1H)

Example 30: Preparation of (R)-3,5-difluoro-4-((4-fluoro-2-(3-(methylamino)pyrrolidin-1-yl)phenyl)amino)-N-(thiazol-4-yl)benzenesulfonamide

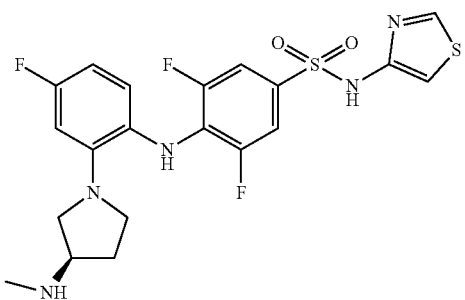 [SMILES: CN[C@@H]1CCN(c2cc(F)ccc2Nc2c(F)cc(S(=O)(=O)Nc3cscn3)cc2F)C1]

1H NMR (500 MHz, MeOD): 8.65 (s, 1H), 7.37 (d, 2H), 6.77-6.74 (m, 2H), 6.69 (d, 1H), 6.56-6.52 (m, 1H), 3.41-3.26 (m, 3H), 3.26-3.24 (m, 1H), 3.05-3.02 (m, 1H), 2.48 (s, 3H), 2.20-2.18 (m, 1H), 1.83-1.81 (m, 1H)

Example 31: Preparation of (R)-5-chloro-2-fluoro-4-((4-fluoro-2-(3-(methylamino)pyrrolidin-1-yl)phenyl)amino)-N-(thiazol-4-yl)benzenesulfonamide

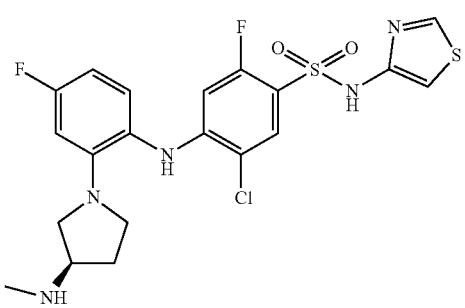 [SMILES: CN[C@@H]1CCN(c2cc(F)ccc2Nc2cc(F)c(S(=O)(=O)Nc3cscn3)cc2Cl)C1]

1H NMR (500 MHz, MeOD): 8.67 (s, 1H), 7.72 (d, 1H), 7.04 (t, 1H), 6.81 (d, 1H), 6.62 (t, 1H), 5.98 (d, 1H), 5.48 (s, 1H), 3.43-3.36 (m, 2H), 3.39-3.36 (m, 1H), 3.30-3.26 (m, 2H), 2.36 (s, 3H), 2.36-2.10 (m, 1H), 1.77-1.73 (m, 1H)

Example 32: Preparation of 5-chloro-2-fluoro-4-((4-fluoro-2-(3-(methylamino)pyrrolidin-1-yl)phenyl)amino)-N-(thiazol-4-yl)benzenesulfonamide

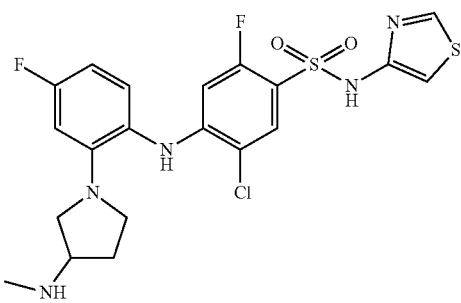 [SMILES: CNC1CCN(c2cc(F)ccc2Nc2cc(F)c(S(=O)(=O)Nc3cscn3)cc2Cl)C1]

1H NMR (500 MHz, MeOD): 8.68 (s, 1H), 7.73 (d, 1H), 7.06 (t, 1H), 6.83 (s, 1H), 6.64 (d, 1H), 6.57 (t, 1H), 6.01 (d, 1H), 3.50-3.40 (m, 3H), 3.28-3.23 (m, 2H), 2.48 (s, 3H), 2.20-2.19 (m, 1H), 1.95-1.93 (m, 1H)

Example 33: Preparation of 4-((2-(3-aminopyrrolidin-1-yl)-4-fluorophenyl)amino)-2-fluoro-N-(thiazol-4-yl)benzenesulfonamide

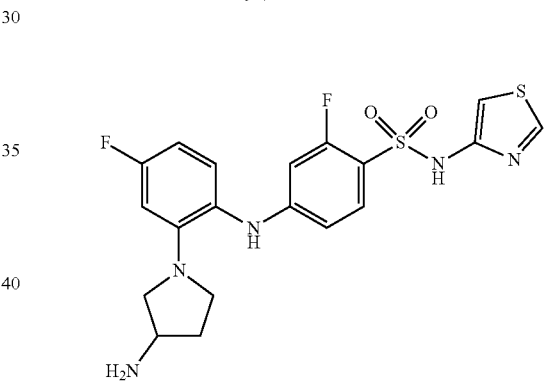

1H NMR (500 MHz, MeOD): 8.72 (s, 1H), 7.58 (t, 1H), 7.10 (t, 1H), 6.93 (m, 1H), 6.68 (d, 1H), 6.62 (d, 1H), 6.45 (d, 1H), 6.33 (d, 1H), 3.79 (m, 1H), 3.50 (m, 2H), 3.30 (m, 1H), 3.20 (m, 1H), 2.29 (m, 1H), 1.95 (m, 1H)

Example 34: Preparation of 4-((2-(3-aminopyrrolidin-1-yl)-4-fluorophenyl)amino)-3-chloro-N-(thiazol-4-yl)benzenesulfonamide

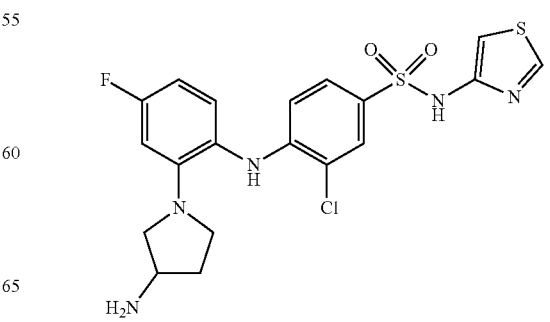

1H NMR (500 MHz, MeOD): 8.70 (d, 1H), 7.75 (s, 1H), 7.47 (d, 1H), 7.07 (t, 1H), 7.07 (t, 1H), 6.64 (d, 1H), 6.58 (t, 1H), 6.37 (d, 1H), 3.71 (m, 1H), 3.59 (m, 2H), 3.25 (m, 1H), 3.13 (m, 1H), 2.13 (m, 1H), 1.77 (m, 1H)

Example 35: Preparation of 4-((2-(3-aminopyrrolidin-1-yl)-4-fluorophenyl)amino)-5-chloro-2-fluoro-N-(thiazol-4-yl)benzenesulfonamide

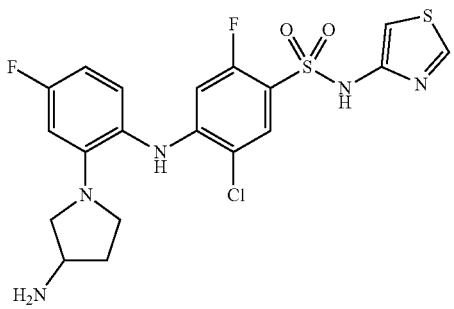 [SMILES: NC1CCN(c2cc(F)ccc2Nc2cc(F)c(S(=O)(=O)Nc3cscn3)cc2Cl)C1]

1H NMR (500 MHz, MeOD): 8.72 (s, 1H), 7.74 (d, 1H), 7.10 (t, 1H), 6.98 (d, 1H), 6.68 (d, 1H), 6.63 (t, 1H), 6.06 (d, 1H), 3.73 (m, 1H), 3.53 (m, 2H), 3.24 (m, 2H), 2.23 (m, 1H), 1.87 (m, 1H)

Example 36: Preparation of 4-((2-(3-(methylamino)pyrrolidin-1-yl)phenyl)amino)-N-(thiazol-4-yl)benzenesulfonamide

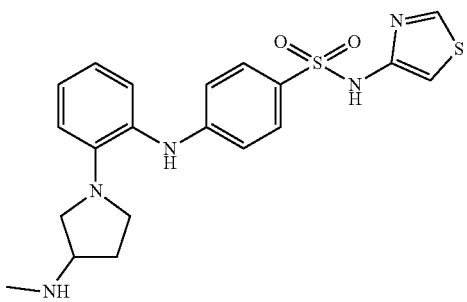 [SMILES: CNC1CCN(c2ccccc2Nc2ccc(S(=O)(=O)Nc3cscn3)cc2)C1]

1H NMR (500 MHz, MeOD): 8.68 (s, 1H), 7.58 (d, 2H), 7.14 (d, 1H), 7.05 (t, 1H), 6.96 (d, 1H), 6.91-6.87 (m, 2H), 6.75 (d, 2H), 3.34-3.30 (m, 2H), 3.18-3.15 (m, 2H), 3.00-2.97 (m, 1H), 2.35 (s, 3H), 2.15-2.12 (m, 1H), 1.75-1.71 (m, 1H)

Example 37: Preparation of 2-fluoro-4-((2-(3-(methylamino)pyrrolidin-1-yl)-4-(trifluoromethyl)phenyl)amino)-N-(thiazol-4-yl)benzenesulfonamide

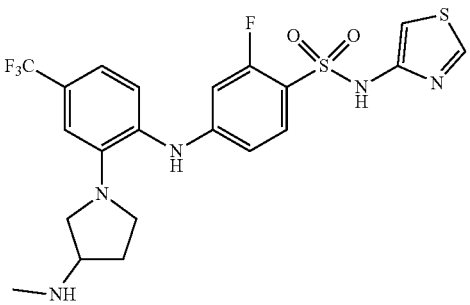 [SMILES: CNC1CCN(c2cc(C(F)(F)F)ccc2Nc2ccc(S(=O)(=O)Nc3cscn3)c(F)c2)C1]

1H NMR (500 MHz, MeOD): 8.69 (d, 1H), 7.65 (t, 1H), 7.35 (d, 1H), 7.20 (m, 2H), 6.87 (d, 1H), 6.74 (d, 1H), 6.66 (d, 1H), 3.65 (m, 1H), 3.47 (m, 1H), 3.37 (m, 2H), 3.03 (m, 1H), 2.60 (s, 3H), 2.30 (m, 1H), 2.02 (m, 1H)

Example 38: Preparation of 3-chloro-4-((2-(3-(methylamino)pyrrolidin-1-yl)-4-(trifluoromethyl)phenyl)amino)-N-(thiazol-4-yl)benzenesulfonamide

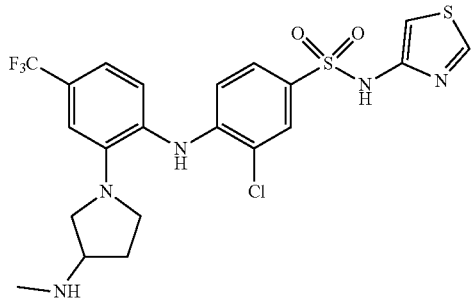 [SMILES: CNC1CCN(c2cc(C(F)(F)F)ccc2Nc2ccc(S(=O)(=O)Nc3cscn3)cc2Cl)C1]

1H NMR (500 MHz, MeOD): 8.67 (d, 1H), 7.80 (d, 1H), 7.53 (d, 1H), 7.25 (d, 1H), 7.17 (s, 1H), 7.13 (d, 1H), 6.89 (d, 1H), 6.59 (d, 1H), 3.35 (m, 2H), 3.28 (m, 1H), 3.12 (m, 2H), 2.37 (s, 3H), 2.11 (m, 1H), 1.75 (m, 1H)

Example 39: Preparation of 4-((4-(difluoromethoxy)-2-(3-(methylamino)pyrrolidin-1-yl)phenyl)amino)-2-fluoro-N-(thiazol-4-yl)benzenesulfonamide

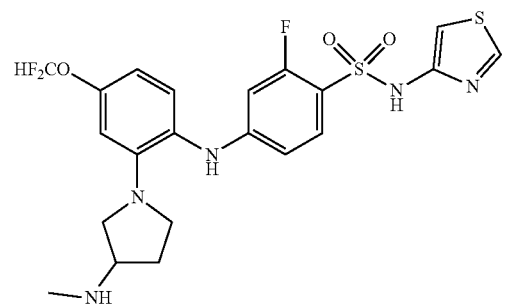

1H NMR (500 MHz, MeOD): 8.69 (s, 1H), 7.58 (t, 1H), 7.12 (d, 1H), 6.70 (t, 1H), 6.66 (m, 2H), 6.50 (d, 1H), 6.38 (d, 1H), 3.59 (m, 1H), 3.41 (m, 2H), 3.32 (m, 1H), 3.12 (m, 1H), 2.54 (s, 3H), 2.24 (m, 1H), 1.93 (m, 1H)

Example 40: Preparation of 3-chloro-4-((4-(difluoromethoxy)-2-(3-(methylamino)pyrrolidin-1-yl)phenyl)amino)-N-(thiazol-4-yl)benzenesulfonamide

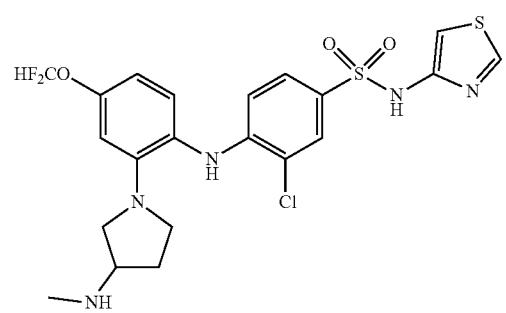

1H NMR (500 MHz, MeOD): 8.69 (s, 1H), 7.76 (s, 1H), 7.47 (d, 1H), 7.09 (d, 1H), 6.81 (t, 2H), 6.65 (m, 2H), 6.39 (d, 1H), 3.40 (m, 3H), 3.18 (m, 2H), 2.44 (s, 3H), 2.15 (m, 1H), 1.81 (m, 1H)

Example 41: Preparation of (R)-4-((4-fluoro-2-(3-fluoropyrrolidin-1-yl)phenyl)amino)-N-(thiazol-4-yl)benzenesulfonamide

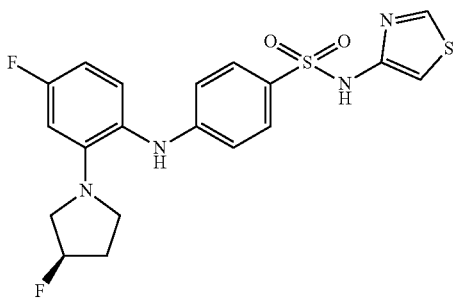 [SMILES: O=S(=O)(Nc1cscn1)c1ccc(Nc2ccc(F)cc2N2CC[C@@H](F)C2)cc1]

1H NMR (500 MHz, MeOD): 8.68 (s, 1H), 7.54 (d, 2H), 7.02 (t, 1H), 6.92 (s, 1H), 6.60 (d, 1H), 6.52-6.49 (m, 3H), 3.57-3.53 (m, 1H), 3.49-3.46 (m, 1H), 3.26-3.21 (m, 3H), 2.10-2.06 (m, 1H), 2.00-1.94 (m, 1H)

Example 42: Preparation of (R)-2-fluoro-4-((4-fluoro-2-(3-fluoropyrrolidin-1-yl)phenyl)amino)-N-(thiazol-4-yl)benzenesulfonamide

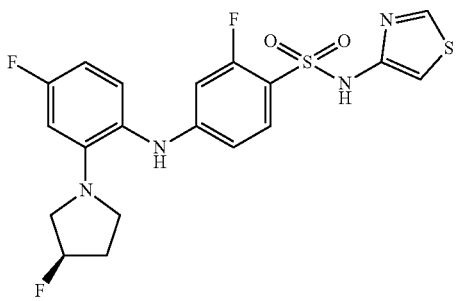 [SMILES: O=S(=O)(Nc1cscn1)c1ccc(Nc2ccc(F)cc2N2CC[C@@H](F)C2)cc1F]

1H NMR (500 MHz, MeOD): 8.69 (s, 1H), 7.54 (t, 1H), 7.01 (t, 1H), 6.90 (d, 1H), 6.59 (t, 1H), 6.50 (d, 1H), 6.32 (d, 1H), 6.17 (d, 1H), 3.43-3.41 (m, 2H), 3.26-3.21 (m, 2H), 2.21-1.94 (m, 3H)

Example 43: Preparation of (R)-3-chloro-4-((4-fluoro-2-(3-fluoropyrrolidin-1-yl)phenyl)amino)-N-(thiazol-4-yl)benzenesulfonamide

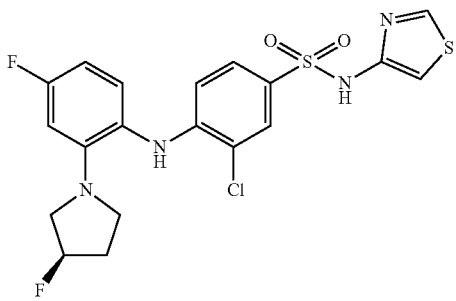

1H NMR (500 MHz, MeOD): 8.69 (s, 1H), 7.73 (s, 1H), 7.44 (d, 1H), 7.04 (t, 1H), 6.92 (s, 1H), 6.61 (d, 1H), 6.53 (t, 1H), 6.28 (d, 1H), 3.47-3.41 (m, 3H), 3.26-3.24 (m, 2H), 2.12-1.97 (m, 2H)

Example 44: Preparation of (R)-3,5-difluoro-4-((4-fluoro-2-(3-fluoropyrrolidin-1-yl)phenyl)amino)-N-(thiazol-4-yl)benzenesulfonamide

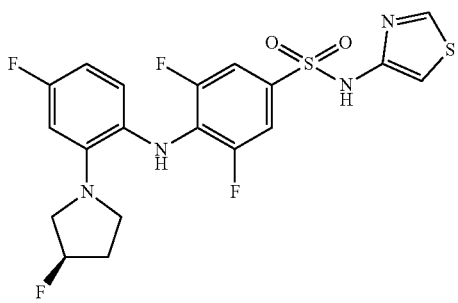 [SMILES: O=S(=O)(Nc1cscn1)c1cc(F)c(Nc2ccc(F)cc2N2CC[C@@H](F)C2)c(F)c1]

1H NMR (500 MHz, MeOD): 8.73 (s, 1H), 7.34 (d, 2H), 7.04 (s, 1H), 6.92 (t, 1H), 6.57 (d, 1H), 6.47 (t, 1H), 3.56-3.25 (m, 4H), 3.13-3.11 (m, 1H), 2.04-1.99 (m, 2H)

Example 45: Preparation of (R)-5-chloro-2-fluoro-4-((4-fluoro-2-(3-fluoropyrrolidin-1-yl)phenyl)amino)-N-(thiazol-4-yl)benzenesulfonamide

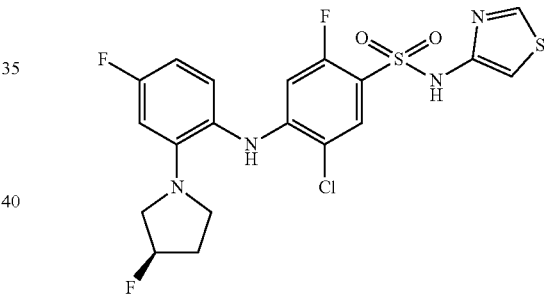

1H NMR (500 MHz, MeOD): 8.70 (s, 1H), 7.70 (d, 1H), 7.04 (t, 1H), 6.96 (d, 1H), 6.65 (d, 1H), 6.55 (t, 1H), 5.92 (d, 1H), 3.46-3.40 (m, 3H), 3.37-3.33 (m, 2H), 2.15-1.96 (m, 2H)

Example 46: Preparation of 2-fluoro-4-((3-fluoro-2-(3-(methylamino)pyrrolidin-1-yl)phenyl)amino)-N-(thiazol-4-yl)benzenesulfonamide

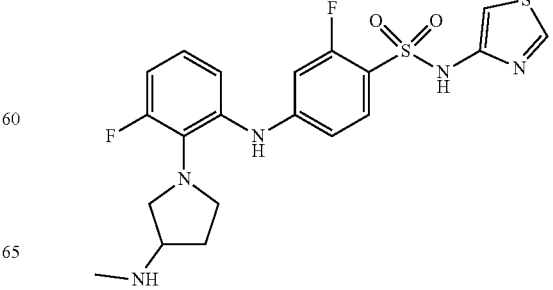

1H NMR (500 MHz, MeOD): 8.69 (d, 1H), 7.65 (t, 1H), 7.08 (lm, 2H), 6.88 (m, 3H), 6.74 (m, 1H), 3.56 (m, 1H), 3.37 (m, 2H), 3.34 (m, 1H), 3.17 (m, 1H), 3.16 (s, 3H), 2.35 (m, 1H), 2.05 (m, 1H)

Example 47: Preparation of 3-chloro-4-((3-fluoro-2-(3-(methylamino)pyrrolidin-1-yl)phenyl)amino)-N-(thiazol-4-yl)benzenesulfonamide

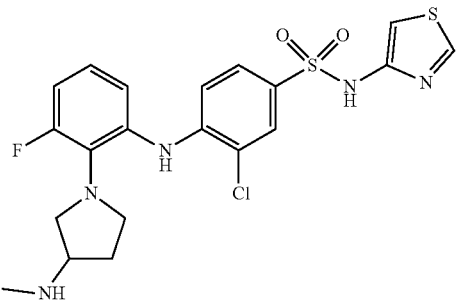 [SMILES: CNC1CCN(c2c(F)cccc2Nc2ccc(S(=O)(=O)Nc3cscn3)cc2Cl)C1]

1H NMR (500 MHz, MeOD): 8.67 (d, 1H), 7.84 (d, 1H), 7.63 (d, 1H), 7.19 (d, 1H), 7.05 (m, 2H), 6.87 (s, 1H), 6.79 (m, 1H), 3.60 (m, 1H), 3.52 (m, 1H), 3.33 (m, 1H), 3.26 (m, 1H), 3.20 (m, 1H), 2.56 (s, 3H), 2.27 (m, 1H), 1.90 (m, 1H)

Example 48: Preparation of 5-chloro-2-fluoro-4-((3-fluoro-2-(3-(methylamino)pyrrolidin-1-yl)phenyl)amino)-N-(thiazol-4-yl)benzenesulfonamide

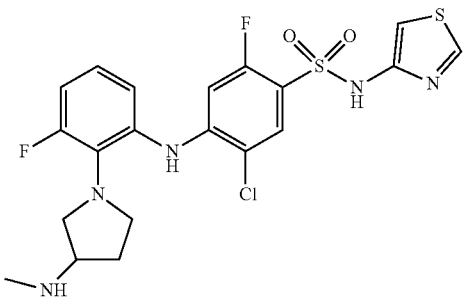 [SMILES: CNC1CCN(c2c(F)cccc2Nc2cc(F)c(S(=O)(=O)Nc3cscn3)cc2Cl)C1]

1H NMR (500 MHz, MeOD): 8.65 (s, 1H), 7.81 (d, 1H), 7.10 (m, 1H), 7.05 (m, 1H), 6.84 (m, 3H), 3.53 (m, 3H), 3.25 (m, 2H), 2.56 (s, 3H), 2.26 (m, 1H), 1.91 (m, 1H)

Example 49: Preparation of 2-fluoro-4-((2-(3-(methylamino)pyrrolidin-1-yl)phenyl)amino)-N-(thiazol-4-yl)benzenesulfonamide

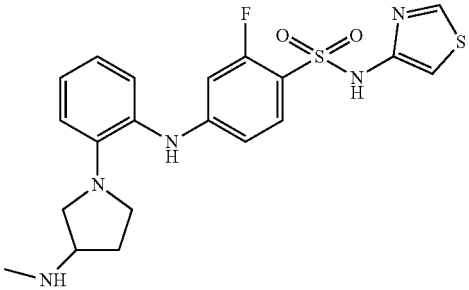 [SMILES: CNC1CCN(c2ccccc2Nc2ccc(S(=O)(=O)Nc3cscn3)c(F)c2)C1]

1H NMR (500 MHz, MeOD): 8.68 (s, 1H), 7.57 (t, 1H), 7.14-7.09 (m, 2H), 6.97 (d, 1H), 6.92-6.90 (m, 1H), 6.84 (s, 1H), 6.55 (d, 1H), 6.40 (d, 1H), 3.42-3.41 (m, 1H), 3.34-3.30 (m, 1H), 3.26-3.21 (m, 2H), 3.04-3.02 (m, 1H), 2.42 (s, 3H), 2.20-2.17 (m, 1H), 1.85-1.81 (m, 1H)

Example 50: Preparation of 3-chloro-4-((2-(3-(methylamino)pyrrolidin-1-yl)phenyl)amino)-N-(thiazol-4-yl)benzenesulfonamide

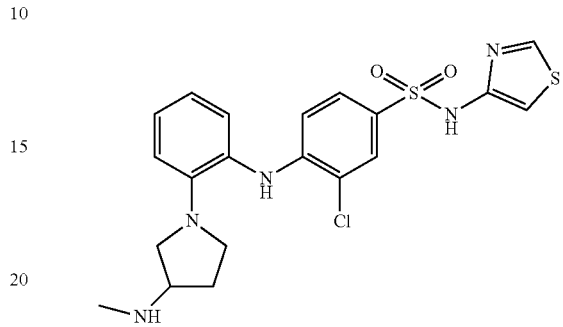

1H NMR (500 MHz, MeOD): 8.66 (s, 1H), 7.76 (s, 1H), 7.48 (d, 1H), 7.15-7.10 (m, 2H), 6.96 (d, 1H), 6.89-6.86 (m, 1H), 6.83 (s, 1H), 6.52 (d 1H), 3.30-3.25 (m, 3H), 3.11-3.07 (m, 2H), 2.34 (s, 3H), 2.10-2.07 (m, 1H), 1.73-1.69 (m, 1H)

Example 51: Preparation of 3,5-difluoro-4-((2-(3-(methylamino)pyrrolidin-1-yl)phenyl)amino)-N-(thiazol-4-yl)benzenesulfonamide

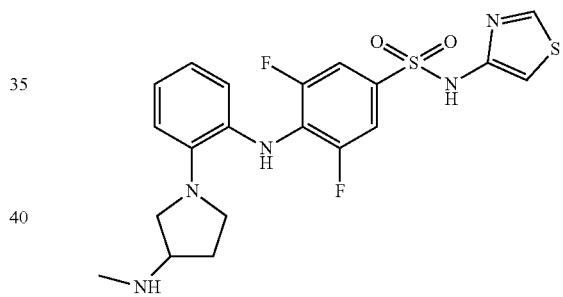

1H NMR (500 MHz, MeOD): 8.65 (s, 1H), 7.43 (d, 2H), 7.04 (d, 1H), 6.93-6.87 (m, 2H), 6.75 (s, 1H), 6.64 (d, 1H), 3.63-3.60 (m, 1H), 3.45-3.43 (m, 2H), 3.19-3.17 (m, 1H), 2.96-2.92 (m, 1H), 2.61 (s, 3H), 2.32-2.28 (m, 1H), 1.98-1.95 (m, 1H)

Example 52: Preparation of 5-chloro-2-fluoro-4-((2-(3-(methylamino)pyrrolidin-1-yl)phenyl)amino)-N-(thiazol-4-yl)benzenesulfonamide

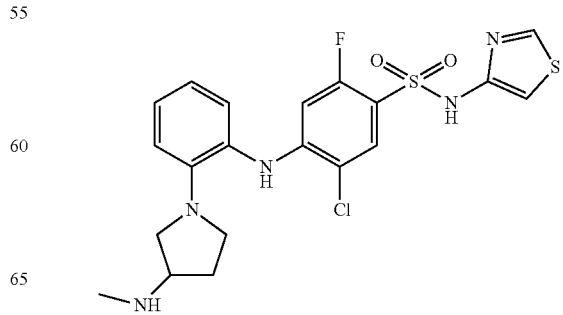

1H NMR (500 MHz, MeOD): 8.66 (s, 1H), 7.74 (d, 1H), 7.20 (t, 1H), 7.12 (d, 1H), 6.96 (d, 1H), 6.92-6.89 (m, 1H), 6.79 (s, 1H), 6.12 (d, 1H), 3.30 (s, 3H), 3.16-3.11 (m, 2H), 2.40 (s, 3H), 2.15-2.12 (m, 1H), 1.79-1.78 (m, 1H)

Example 53: Preparation of 2-fluoro-4-((4-methoxy-2-(3-(methylamino)pyrrolidin-1-yl)phenyl)amino)-N-(thiazol-4-yl)benzenesulfonamide

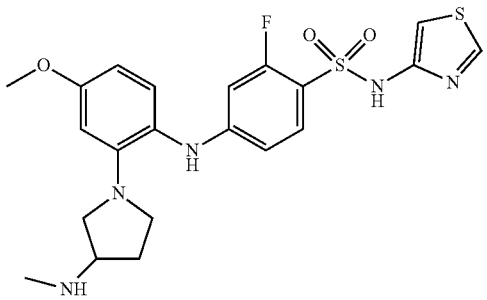 [SMILES: CNC1CCN(c2cc(OC)ccc2Nc2ccc(S(=O)(=O)Nc3cscn3)c(F)c2)C1]

1H NMR (500 MHz, MeOD): 8.71 (s, 1H), 7.55 (t, 1H), 7.02 (d, 1H), 6.89 (s, 1H), 6.49 (m, 3H), 6.33 (d, 1H), 3.78 (s, 3H), 3.67 (m, 1H), 3.42 (m, 1H), 3.38 (m, 2H), 3.10 (m, 1H), 2.58 (s, 3H), 2.27 (m, 1H), 1.99 (m, 1H)

Example 54: Preparation of 3-chloro-4-((4-methoxy-2-(3-(methylamino)pyrrolidin-1-yl)phenyl)amino)-N-(thiazol-4-yl)benzenesulfonamide

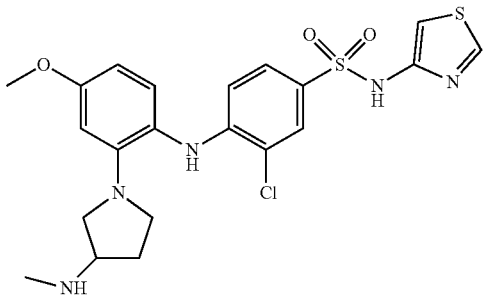 [SMILES: CNC1CCN(c2cc(OC)ccc2Nc2ccc(S(=O)(=O)Nc3cscn3)cc2Cl)C1]

1H NMR (500 MHz, MeOD): 8.70 (d, 1H), 7.74 (d, 1H), 7.45 (d, 1H), 7.00 (d, 1H), 6.94 (d, 1H), 6.49 (m, 2H), 6.37 (d, 1H), 3.78 (s, 3H), 3.47 (m, 1H), 3.38 (m, 2H), 3.27 (m, 1H), 3.16 (m, 1H), 2.46 (s, 3H), 2.17 (m, 1H), 1.83 (m, 1H)

Example 55: Preparation of 5-chloro-2-fluoro-4-((4-methoxy-2-(3-(methylamino)pyrrolidin-1-yl)phenyl)amino)-N-(thiazol-4-yl)benzenesulfonamide

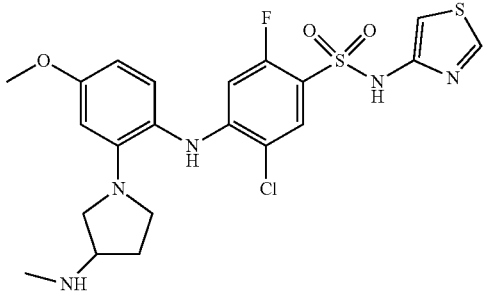 [SMILES: CNC1CCN(c2cc(OC)ccc2Nc2cc(F)c(S(=O)(=O)Nc3cscn3)cc2Cl)C1]

1H NMR (500 MHz, MeOD): 8.71 (d, 1H), 7.72 (d, 1H), 7.01 (d, 1H), 6.89 (d, 1H), 6.51 (m, 2H), 6.48 (d, 1H), 3.81 (s, 3H), 3.67 (m, 1H), 3.45 (m, 3H), 3.20 (m, 1H), 2.59 (s, 3H), 2.27 (m, 1H), 1.96 (m, 1H)

Example 56: Preparation of (R)-4-((4-methoxy-2-(3-(methylamino)piperidin-1-yl)phenyl)amino)-N-(thiazol-4-yl)benzenesulfonamide

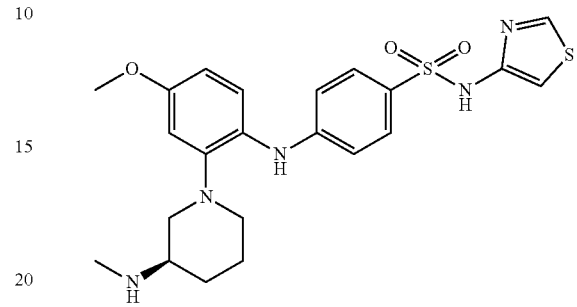

1H NMR (500 MHz, MeOD): 8.68 (s, 1H), 7.59 (d, 2H), 7.13 (d, 1H), 6.93 (s, 1H), 6.78 (d, 2H), 6.62 (d, 2H), 3.77 (s, 3H), 3.25 (m, 1H), 2.87-2.65 (m, 4H), 2.39 (s, 3H), 1.85 (m, 1H), 1.70 (m, 1H), 1.54 (m, 2H)

Example 57: Preparation of (R)-2-fluoro-4-((4-methoxy-2-(3-(methylamino)piperidin-1-yl)phenyl)amino)-N-(thiazol-4-yl)benzenesulfonamide

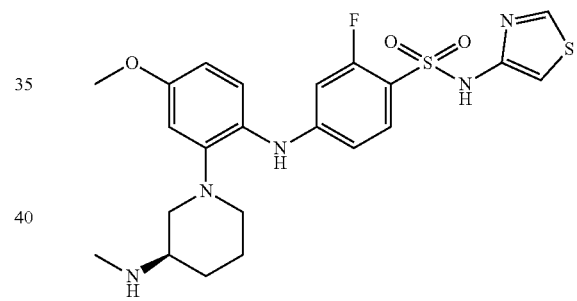

1H NMR (500 MHz, MeOD): 8.70 (s, 1H), 7.58 (t, 1H), 7.12 (d, 1H), 6.88 (s, 1H), 6.65-6.58 (m, 3H), 6.49 (d, 1H), 3.78 (s, 3H), 3.25 (m, 1H), 2.89-2.77 (m, 4H), 2.47 (s, 3H), 1.88 (m, 2H), 1.46 (m, 2H)

Example 58: Preparation of (R)-3-chloro-4-((4-methoxy-2-(3-(methylamino)piperidin-1-yl)phenyl)amino)-N-(thiazol-4-yl)benzenesulfonamide

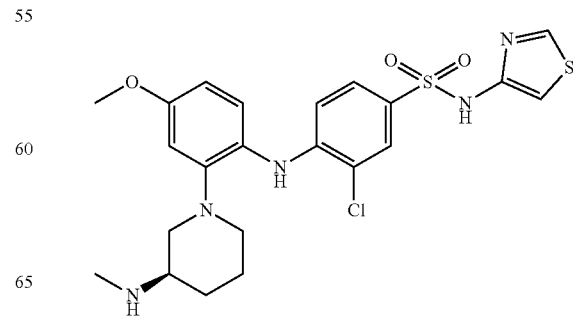

1H NMR (500 MHz, MeOD): 8.68 (s, 1H), 7.77 (s, 1H), 7.51 (d, 1H), 7.17 (d, 1H), 6.90 (s, 1H), 6.72 (d, 1H), 6.67 (d, 2H), 3.78 (s, 3H), 2.96-2.94 (m, 1H), 2.70-2.45 (m, 3H), 2.33 (s, 3H), 1.88 (m, 1H), 1.68 (m, 1H), 1.44-1.37 (m, 3H)

Example 59: Preparation of (R)-3,5-difluoro-4-((4-methoxy-2-(3-(methylamino)piperidin-1-yl)phenyl)amino)-N-(thiazol-4-yl)benzenesulfonamide

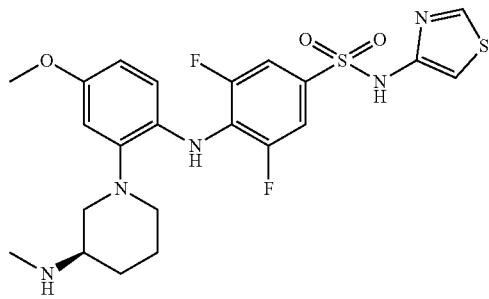 [SMILES: CN[C@@H]1CCCN(c2cc(OC)ccc2Nc2c(F)cc(S(=O)(=O)Nc3cscn3)cc2F)C1]

1H NMR (500 MHz, MeOD): 8.68 (s, 1H), 7.40 (d, 2H), 6.80 (t, 2H), 6.63 (s, 1H), 6.56 (d, 1H), 3.74 (s, 3H), 2.90-2.70 (m, 4H), 2.53 (s, 3H), 1.86-1.28 (m, 5H)

Example 60: Preparation of (R)-5-chloro-2-fluoro-4-((4-methoxy-2-(3-(methylamino)piperidin-1-yl)phenyl)amino)-N-(thiazol-4-yl)benzenesulfonamide

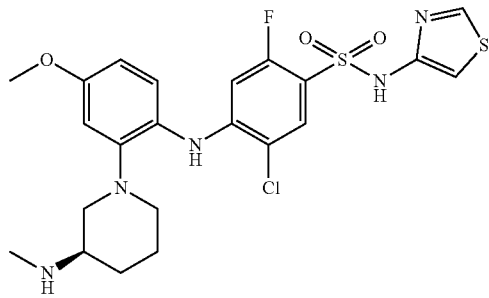 [SMILES: CN[C@@H]1CCCN(c2cc(OC)ccc2Nc2cc(F)c(S(=O)(=O)Nc3cscn3)cc2Cl)C1]

1H NMR (500 MHz, MeOD): 8.68 (s, 1H), 7.74 (d, 1H), 7.15 (d, 1H), 6.81 (s, 1H), 6.69 (d, 2H), 6.31 (d, 1H), 3.79 (s, 3H), 2.99 (m, 1H), 2.67-2.49 (m, 3H), 2.39 (s, 3H), 1.88 (m, 1H), 1.68 (m, 1H), 1.35-1.28 (m, 3H)

Example 61: Preparation of 3-chloro-4-((4-fluoro-2-(4-methylpiperazin-1-yl)phenyl)amino)-N-(thiazol-4-yl)benzenesulfonamide

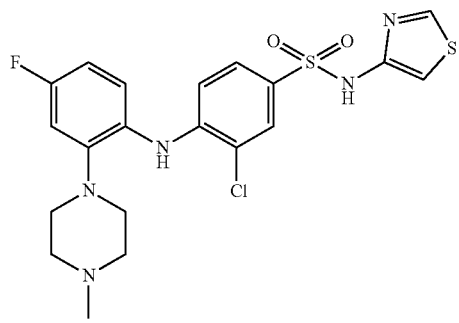

1H NMR (500 MHz, MeOD): 8.70 (s, 1H), 7.81 (s, 1H), 7.54 (d, 1H), 7.24 (d, 1H), 7.00 (s, 1H), 6.89-6.79 (m, 3H), 2.98-2.92 (m, 4H), 2.37 (m, 4H), 2.20 (s, 3H)

Example 62: Preparation of 5-chloro-2-fluoro-4-((4-fluoro-2-(4-methylpiperazin-1-yl)phenyl)amino)-N-(thiazol-4-yl)benzenesulfonamide

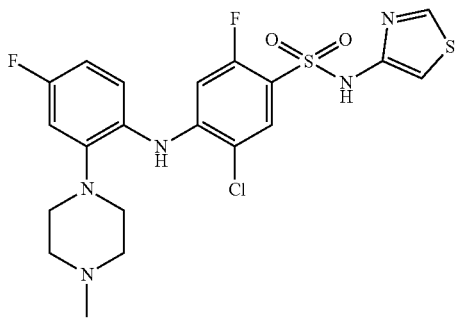 [SMILES: CN1CCN(c2cc(F)ccc2Nc2cc(F)c(S(=O)(=O)Nc3cscn3)cc2Cl)CC1]

1H NMR (500 MHz, MeOD): 8.71 (s, 1H), 7.77 (d, 1H), 7.24 (t, 1H), 6.98 (s, 1H), 6.91-6.82 (m, 2H), 6.40 (d, 1H), 2.96 (m, 4H), 2.36 (m, 4H), 2.15 (s, 3H)

Example 63: Preparation of (S)-5-chloro-4-((2-(3-(dimethylamino)pyrrolidin-1-yl)-4-fluorophenyl)amino)-2-fluoro-N-(thiazol-4-yl)benzenesulfonamide

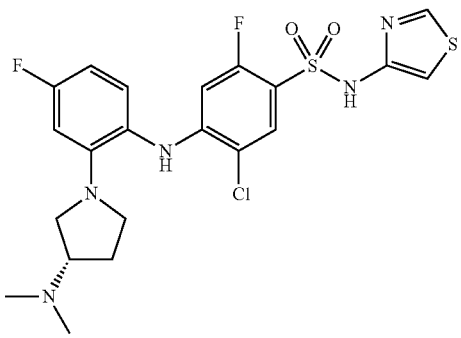 [SMILES: CN(C)[C@H]1CCN(c2cc(F)ccc2Nc2cc(F)c(S(=O)(=O)Nc3cscn3)cc2Cl)C1]

1H NMR (500 MHz, CDCl₃): 8.62 (d, 1H), 7.79 (d, 1H), 6.98 (m, 2H), 6.52 (m, 2H), 6.23 (m, 2H), 3.22 (m, 3H), 3.14 (m, 1H), 2.70 (m, 1H), 2.23 (s, 6H), 1.78 (m, 2H)

Example 64: Preparation of (S)-5-chloro-4-((2-(3-(dimethylamino)pyrrolidin-1-yl)-4-(trifluoromethyl)phenyl)amino)-2-fluoro-N-(thiazol-4-yl)benzenesulfonamide

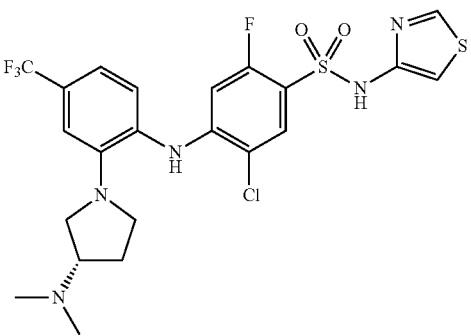 [SMILES: CN(C)[C@H]1CCN(c2cc(C(F)(F)F)ccc2Nc2cc(F)c(S(=O)(=O)Nc3cscn3)cc2Cl)C1]

1H NMR (500 MHz, CDCl₃): 8.63 (s, 1H), 7.83 (d, 1H), 7.17 (m, 3H), 6.99 (s, 1H), 6.64 (s, 1H), 6.56 (d, 1H), 3.25 (m, 4H), 2.81 (m, 1H), 2.24 (s, 6H), 1.85 (m, 2H)

Example 65: Preparation of 5-chloro-2-fluoro-4-((2-(4-methylpiperazin-1-yl)-4-(trifluoromethyl)phenyl)amino)-N-(thiazol-4-yl)benzenesulfonamide

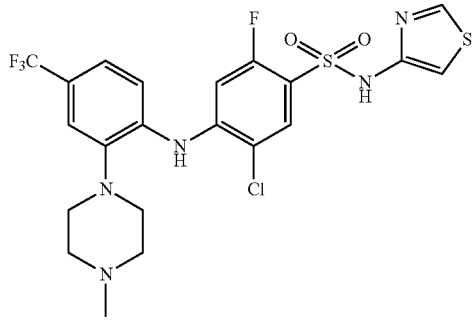 [SMILES: CN1CCN(c2cc(C(F)(F)F)ccc2Nc2cc(F)c(S(=O)(=O)Nc3cscn3)cc2Cl)CC1]

1H NMR (500 MHz, MeOD): 8.71 (s, 1H), 7.72 (d, 1H), 7.28 (m, 3H), 6.06 (s, 1H), 6.06 (d, 1H), 3.37 (m, 4H), 2.66 (m, 4H), 2.37 (s, 3H)

Example 66: Preparation of 5-chloro-4-((4-(difluoromethoxy)-2-(4-methylpiperazin-1-yl)phenyl)amino)-2-fluoro-N-(thiazol-4-yl)benzenesulfonamide

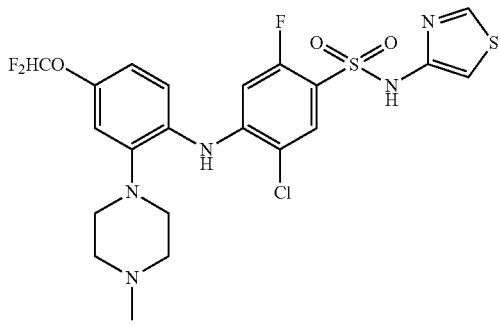 [SMILES: CN1CCN(c2cc(OC(F)F)ccc2Nc2cc(F)c(S(=O)(=O)Nc3cscn3)cc2Cl)CC1]

1H NMR (500 MHz, MeOD): 8.72 (s, 1H), 7.78 (s, 1H), 7.28 (d, 1H), 6.98-6.82 (m, 4H), 6.49 (d, 1H), 3.39-3.30 (m, 4H), 2.97 (m, 4H), 2.25 (s, 3H)

Example 67: Preparation of 5-chloro-2-fluoro-4-((2-(4-methylpiperazin-1-yl)-4-(trifluoromethoxy)phenyl)amino)-N-(thiazol-4-yl)benzenesulfonamide

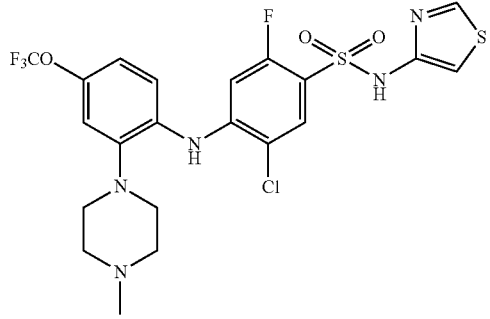 [SMILES: CN1CCN(c2cc(OC(F)(F)F)ccc2Nc2cc(F)c(S(=O)(=O)Nc3cscn3)cc2Cl)CC1]

1H NMR (500 MHz, MeOD): 8.71 (s, 1H), 7.81 (d, 1H), 7.35 (d, 1H), 7.03-6.98 (m, 3H), 6.59 (d, 1H), 4.09 (d, 1H), 2.97 (m, 4H), 2.42 (m, 4H), 2.22 (s, 3H)

Example 68: Preparation of (S)-3-chloro-4-((2-(3-(dimethylamino)pyrrolidin-1-yl)-4-(trifluoromethyl)phenyl)amino)-N-(thiazol-4-yl)benzenesulfonamide

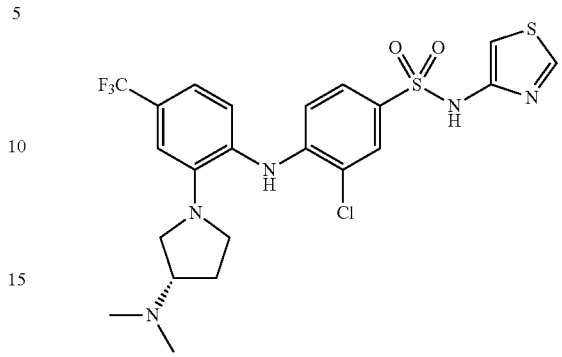

1H NMR (500 MHz, CDCl$_3$): 8.66 (d, 1H), 7.80 (d, 1H), 7.52 (dd, 1H), 7.28 (s, 1H), 7.14 (m, 2H), 7.05 (d, 1H), 6.89 (d, 1H), 6.64 (s, 1H), 3.22 (m, 2H), 3.16 (m, 2H), 2.79 (m, 1H), 2.23 (s, 6H), 2.10 (m, 1H), 2.06 (m, 1H)

Example 69: Preparation of (S)-2-fluoro-4-((4-fluoro-2-(3-(methylamino)pyrrolidin-1-yl)phenyl)amino)-N-(thiazol-4-yl)benzenesulfonamide

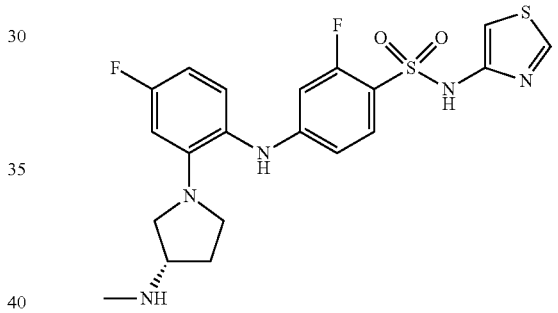

1H NMR (500 MHz, MeOD): 8.70 (d, 1H), 7.56 (t, 1H), 7.06 (t, 1H), 6.90 (d, 1H), 6.65 (d, 1H), 6.57 (t, 1H), 6.43 (d, 1H), 6.30 (d, 1H), 3.37 (m, 3H), I 3.24 (m, 1H), 3.13 (m, 1H), 2.44 (S, 3H), 2.18 (m, 1H), 2.00 (m, 1H)

Example 70: Preparation of (S)-5-chloro-2-fluoro-4-((4-fluoro-2-(3-(methylamino)pyrrolidin-1-yl)phenyl)amino)-N-(thiazol-4-yl)benzenesulfonamide

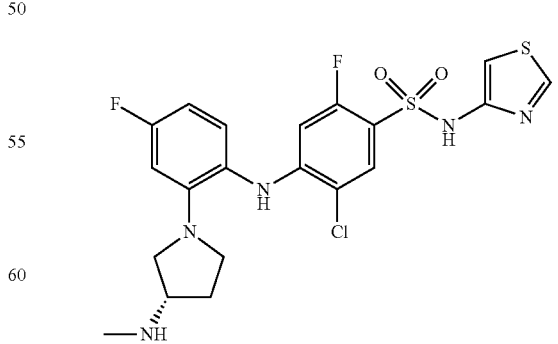

1H NMR (500 MHz, MeOD): 8.71 (s, 1H), 7.73 (d, 1H), 7.07 (t, 1H), 6.92 (s, 1H), 6.67 (d, 1H), 6.59 (t, 1H), 6.01 (d, 1H), 3.45 (m, 3H), 3.23 (m, 2H), 2.46 (s, 3H), 2.17 (m, 1H), 1.83 (m, 1H)

Example 71: Preparation of (S)-5-chloro-4-((2-(3-(dimethylamino)pyrrolidin-1-yl)-4-methoxyphenyl)amino)-2-fluoro-N-(thiazol-4-yl)benzenesulfonamide

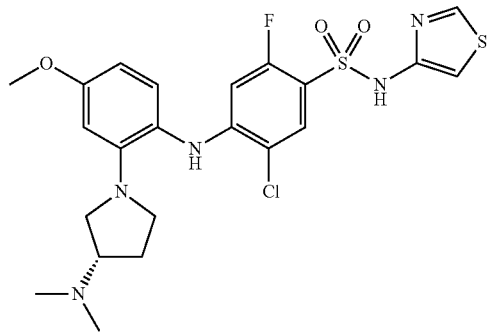 [SMILES: COc1ccc(Nc2cc(F)c(S(=O)(=O)Nc3cscn3)cc2Cl)c(N2CC[C@H](N(C)C)C2)c1]

1H NMR (500 MHz, CDCl₃): 8.58 (d, 1H), 7.76 (d, 1H), 6.99 (m, 2H), 6.37 (m, 2H), 6.26 (m, 2H), 3.80 (s, 3H), 3.25-3.21 (m, 5H), 2.76 (m, 1H), 2.21 (s, 6H), 2.05 (m, 1H)

Example 72: Preparation of (S)-5-chloro-4-((4-(difluoromethoxy)-2-(3-(dimethylamino)pyrrolidin-1-yl)phenyl)amino)-2-fluoro-N-(thiazol-4-yl)benzenesulfonamide

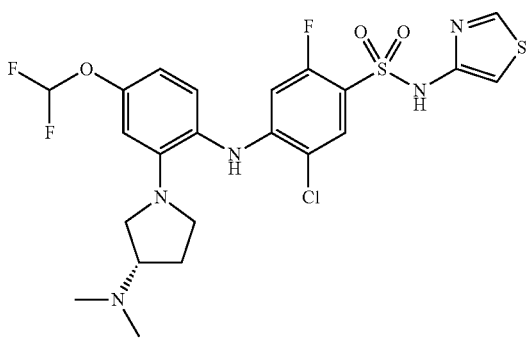 [SMILES: CN(C)[C@H]1CCN(c2cc(OC(F)F)ccc2Nc2cc(F)c(S(=O)(=O)Nc3cscn3)cc2Cl)C1]

1H NMR (500 MHz, CDCl₃): 8.63 (d, 1H), 7.79 (d, 1H), 7.04 (m, 1H), 6.96 (d, 1H), 6.57 (m, 2H), 6.50 (d, 1H), 6.29 (m, 2H), 3.22 (m, 4H), 2.75 (m, 1H), 2.22 (s, 6H), 2.05 (m, 1H), 1.78 (m, 1H)

Example 73: Preparation of (R)-5-chloro-4-((2-(3-(dimethylamino)pyrrolidin-1-yl)-4-fluorophenyl)amino)-2-fluoro-N-(thiazol-4-yl)benzenesulfonamide

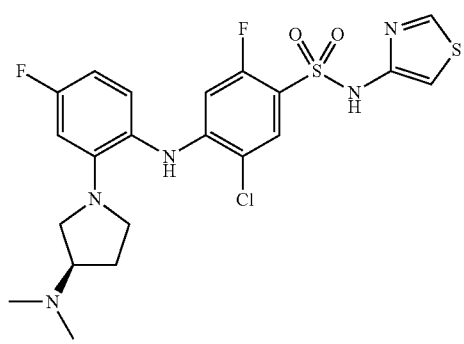 [SMILES: CN(C)[C@@H]1CCN(c2cc(F)ccc2Nc2cc(F)c(S(=O)(=O)Nc3cscn3)cc2Cl)C1]

1H NMR (500 MHz, CDCl₃): 8.64 (s, 1H), 7.79 (d, 1H), 7.01 (t, 1H), 6.98 (s, 1H), 6.51 (m, 2H), 6.23 (m, 2H), 3.24 (m, 5H), 2.71 (m, 1H), 2.20 (s, 6H), 1.77 (m, 1H)

Example 74: Preparation of (R)-5-chloro-4-((2-(3-(dimethylamino)pyrrolidin-1-yl)-4-(trifluoromethyl)phenyl)amino)-2-fluoro-N-(thiazol-4-yl)benzenesulfonamide

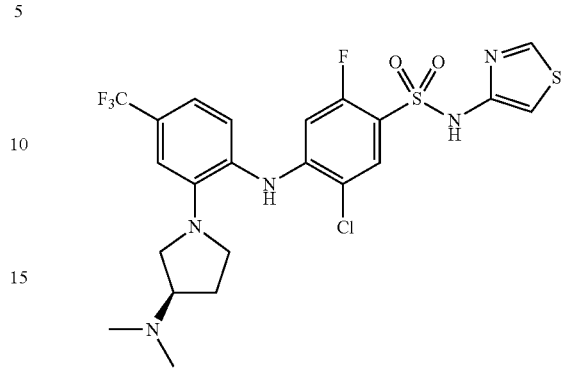

1H NMR (500 MHz, CDCl₃): 8.64 (d, 1H), 7.84 (d, 1H), 7.24 (d, 1H), 7.12 (m, 2H), 6.98 (d, 1H), 6.66 (s, 1H), 6.54 (d, 1H), 3.23 (m, 4H), 2.83 (m, 1H), 2.23 (s, 6H), 1.90 (m, 2H)

Example 75: Preparation of (R)-5-chloro-4-((4-(difluoromethoxy)-2-(3-(dimethylamino)pyrrolidin-1-yl)phenyl)amino)-2-fluoro-N-(thiazol-4-yl)benzenesulfonamide

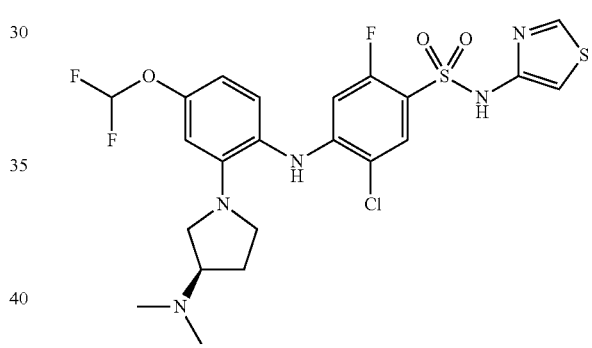

1H NMR (500 MHz, CDCl₃): 8.62 (d, 1H), 7.79 (d, 1H), 7.05 (d, 1H), 6.98 (d, 1H), 6.57 (s, 1H), 6.50 (t, 1H), 6.31 (m, 2H), 3.24 (m, 3H), 3.15 (m, 1H), 2.74 (m, 1H), 2.21 (s, 6H), 1.77 (m, 2H)

Example 76: Preparation of 4-((2-(1,4-diazepan-1-yl)-4-fluorophenyl)amino)-5-chloro-2-fluoro-N-(thiazol-4-yl)benzenesulfonamide

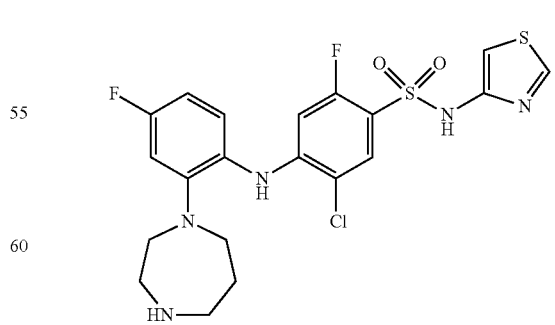

1H NMR (500 MHz, MeOD): 8.69 (s, 1H), 7.76 (d, 1H), 7.20 (m, 1H), 6.97 (d, 1H), 6.92 (s, 1H), 6.82 (t, 1H), 6.22 (d, 1H), 3.30 (m, 2H), 3.20 (t, 2H), 3.10 (m, 4H), 1.95 (m, 2H)

Example 77: Preparation of 5-chloro-4-((4-cyano-2-(3-(methylamino)pyrrolidin-1-yl)phenyl)amino)-2-fluoro-N-(thiazol-4-yl)benzenesulfonamide

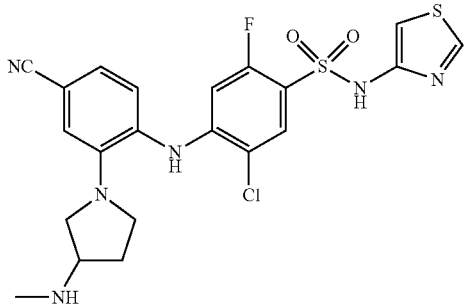 [SMILES: CNC1CCN(c2cc(C#N)ccc2Nc2cc(F)c(S(=O)(=O)Nc3cscn3)cc2Cl)C1]

1H NMR (500 MHz, MeOD): 8.69 (s, 1H), 7.80 (d, 1H), 7.29 (s, 1H), 7.24 (m, 2H), 6.90 (s, 1H), 6.33 (d, 1H), 3.42 (m, 3H), 3.16 (m, 2H), 2.47 (s, 3H), 2.18 (m, 1H), 1.85 (m, 1H)

Example 78: Preparation of (R)—N-(1-(2-((2-chloro-5-fluoro-4-(N-(thiazol-4-yl)sulfamoyl)phenyl)amino)-5-(trifluoromethyl)phenyl)pyrrolidin-3-yl)acetamide

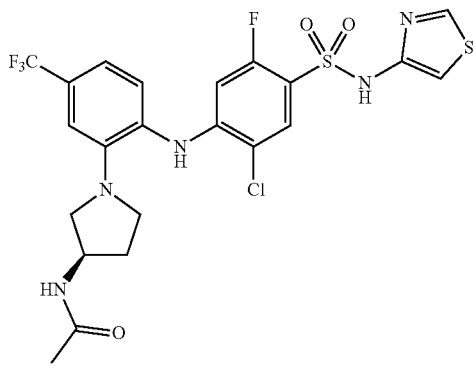 [SMILES: CC(=O)N[C@@H]1CCN(c2cc(C(F)(F)F)ccc2Nc2cc(F)c(S(=O)(=O)Nc3cscn3)cc2Cl)C1]

1H NMR (500 MHz, CDCl₃): 9.25 (broad, 1H), 8.64 (d, 1H), 7.84 (d, 1H), 7.18 (m, 2H), 7.02 (d, 1H), 6.69 (s, 1H), 6.52 (d, 1H), 5.60 (d, 1H), 4.50 (m, 1H), 3.37 (m, 1H), 3.27 (m, 1H), 3.09 (m, 2H), 2.27 (m, 1H), 1.95 (s, 3H), 1.77 (m, 1H)

Example 79: Preparation of (R)—N-(1-(2-((2-chloro-4-(N-(thiazol-4-yl)sulfamoyl)phenyl)amino)-5-(trifluoromethyl)phenyl)pyrrolidin-3-yl)acetamide

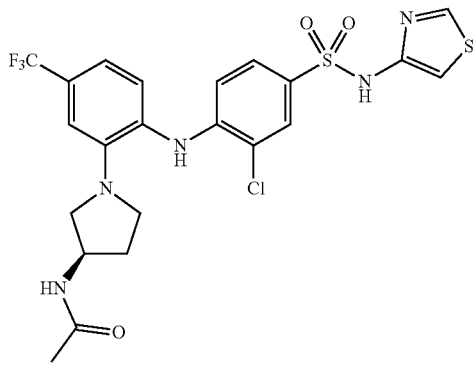 [SMILES: CC(=O)N[C@@H]1CCN(c2cc(C(F)(F)F)ccc2Nc2ccc(S(=O)(=O)Nc3cscn3)cc2Cl)C1]

1H NMR (500 MHz, CDCl₃): 9.34 (s, 1H), 8.69 (d, 1H), 7.79 (d, 1H), 7.52 (d, 1H), 7.28 (d, 1H), 7.18 (m, 2H), 7.07 (s, 1H), 6.86 (d, 1H), 6.69 (s, 1H), 5.59 (d, 1H), 4.51 (m, 1H), 3.49 (s, 3H), 3.33 (m, 1H), 3.26 (m, 1H), 3.06 (m, 2H), 2.27 (m, 1H), 1.94 (s, 3H), 1.75 (m, 1H)

Example 80: Preparation of (S)-3-chloro-4-((2-(3-(methylamino)pyrrolidin-1-yl)-4-(trifluoromethyl)phenyl)amino)-N-(thiazol-4-yl)benzenesulfonamide

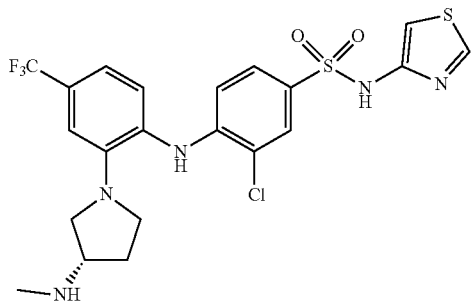 [SMILES: CN[C@H]1CCN(c2cc(C(F)(F)F)ccc2Nc2ccc(S(=O)(=O)Nc3cscn3)cc2Cl)C1]

1H NMR (500 MHz, MeOD): 8.70 (s, 1H), 7.82 (s, 1H), 7.55 (d, 1H), 7.23 (m, 3H), 6.95 (s, 1H), 6.69 (d, 1H), 3.60 (m, 1H), 3.44 (m, 2H), 3.30 (m, 1H), 3.15 (m, 1H), 2.57 (s, 3H), 2.24 (m, 1H), 1.94 (m, 1H

Example 81: Preparation of (S)-5-chloro-2-fluoro-4-((2-(3-(methylamino)pyrrolidin-1-yl)-4-(trifluoromethyl)phenyl)amino)-N-(thiazol-4-yl)benzenesulfonamide

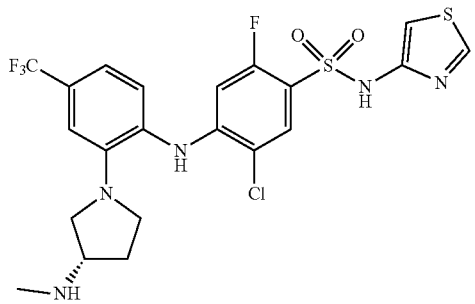

1H NMR (500 MHz, MeOD): 8.65 (s, 1H), 7.77 (d, 1H), 7.24 (d, 1H), 7.19 (s, 1H), 7.16 (d, 1H), 6.74s, 1H), 6.24 (d, 1H), 3.57 (m, 1H), 3.45 (m, 2H), 3.30 (m, 1H), 3.17 (m, 1H), 2.54 (s, 3H), 2.22 (m, 1H), 1.93 (m, 1H)

Example 82: Preparation of 5-chloro-2-fluoro-4-((4-fluoro-2-(3-(methylamino)azetidin-1-yl)phenyl)amino)-N-(thiazol-4-yl)benzenesulfonamide

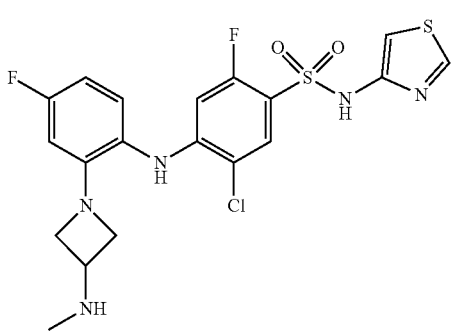 [SMILES: CNC1CN(c2cc(F)ccc2Nc2cc(F)c(S(=O)(=O)Nc3cscn3)cc2Cl)C1]

1H NMR (500 MHz, MeOD): 8.86 (s, 1H), 8.17 (s, 1H), 7.07 (d, 1H), 6.84 (d, 1H), 6.79 (d, 1H), 6.40 (m, 1H), 6.33 (s, 1H), 3.93-3.70 (m, 4H), 3.35 (m, 1H), 3.23 (s, 3H)

Example 83: Preparation of 4-((2-(3-aminoazetidin-1-yl)-4-fluorophenyl)amino)-5-chloro-2-fluoro-N-(thiazol-4-yl)benzenesulfonamide

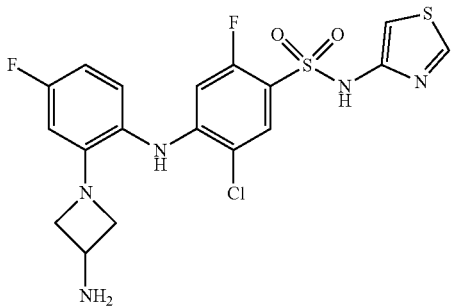 [SMILES: NC1CN(c2cc(F)ccc2Nc2cc(F)c(S(=O)(=O)Nc3cscn3)cc2Cl)C1]

1H NMR (500 MHz, MeOD): 8.84 (s, 1H), 8.07 (s, 1H), 7.11 (d, 1H), 6.85 (d, 1H), 6.81 (d, 1H), 6.40 (m, 1H), 6.33 (s, 1H), 4.03-3.82 (m, 4H), 3.42 (m, 1H)

Example 84: Preparation of 5-chloro-4-((2-(3-(dimethylamino)azetidin-1-yl)-4-fluorophenyl)amino)-2-fluoro-N-(thiazol-4-yl)benzenesulfonamide

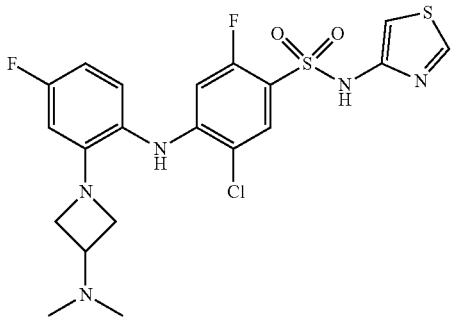 [SMILES: CN(C)C1CN(c2cc(F)ccc2Nc2cc(F)c(S(=O)(=O)Nc3cscn3)cc2Cl)C1]

1H NMR (500 MHz, MeOD): 8.76 (s, 1H), 8.10 (s, 1H), 7.07 (d, 1H), 6.84 (d, 1H), 6.79 (d, 1H), 6.40 (m, 1H), 6.33 (s, 1H), 3.99-3.65 (m, 4H), 3.33 (m, 1H), 3.12 (s, 6H)

Example 85: Preparation of N-(1-(2-((2-chloro-5-fluoro-4-(N-(thiazol-4-yl)sulfamoyl)phenyl)amino)-5-fluorophenyl)azetidin-3-yl)acetamide

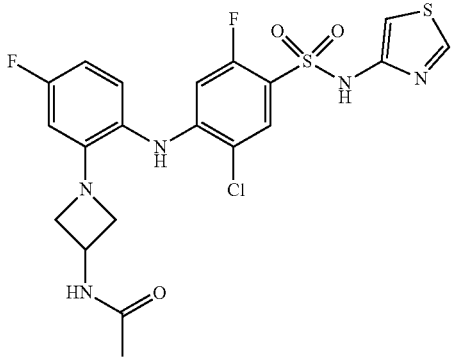 [SMILES: CC(=O)NC1CN(c2cc(F)ccc2Nc2cc(F)c(S(=O)(=O)Nc3cscn3)cc2Cl)C1]

1H NMR (500 MHz, MeOD): 8.56 (s, 1H), 8.00 (s, 1H), 7.00 (d, 1H), 6.77 (d, 1H), 6.71 (d, 1H), 6.30 (m, 1H), 6.29 (s, 1H), 3.91-3.55 (m, 4H), 3.35 (m, 1H), 2.13 (s, 3H)

Example 86: Preparation of 5-chloro-2-fluoro-4-((4-fluoro-2-(3-methoxypyrrolidin-1-yl)phenyl)amino)-N-(thiazol-4-yl)benzenesulfonamide

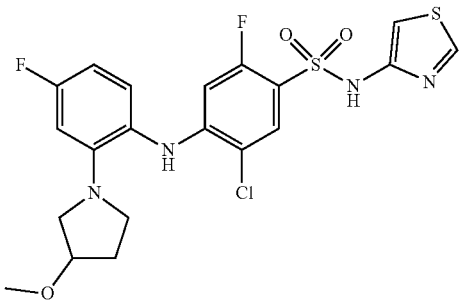 [SMILES: COC1CCN(c2cc(F)ccc2Nc2cc(F)c(S(=O)(=O)Nc3cscn3)cc2Cl)C1]

1H NMR (500 MHz, CDCl$_3$): 10.93 (s, 1H), 8.74 (d, 1H), 7.81 (d, 1H), 6.99 (t, 1H), 6.50 (m, 2H), 6.24 (m, 2H), 3.92 (t, 1H), 3.32 (m, 2H), 3.26 (s, 3H), 3.11 (m, 2H), 2.01 (m, 1H), 1.92 (m, 1H), 1.69 (m, 1H)

Example 87: Preparation of 5-chloro-2-fluoro-4-((2-(3-methoxypyrrolidin-1-yl)-4-(trifluoromethyl)phenyl)amino)-N-(thiazol-4-yl)benzenesulfonamide

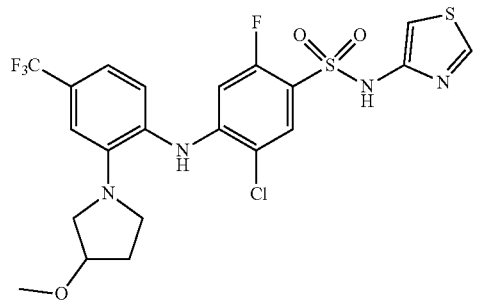 [SMILES: COC1CCN(c2cc(C(F)(F)F)ccc2Nc2cc(F)c(S(=O)(=O)Nc3cscn3)cc2Cl)C1]

1H NMR (500 MHz, CDCl$_3$): 10.79 (s, 1H), 8.74 (d, 1H), 7.85 (d, 1H), 7.25 (m, 2H), 7.15 (s, 1H), 7.11 (d, 1H), 6.94 (d, 1H), 6.66 (s, 1H), 6.56 (d, 1H), 3.97 (t, 1H), 3.31 (m, 2H), 3.30 (s, 3H), 3.12 (m, 2H), 2.04 (m, 2H)

Example 88: Preparation of (R)—N-(1-(2-((2-chloro-5-fluoro-4-(N-(thiazol-4-yl)sulfamoyl)phenyl)amino)-5-fluorophenyl)pyrrolidin-3-yl)acetamide

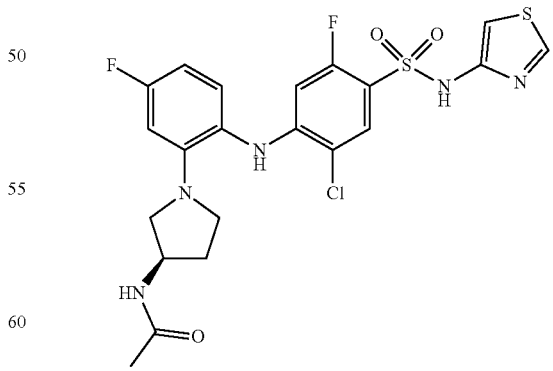

1H NMR (500 MHz, CDCl$_3$): 10.63 (s, 1H), 8.70 (d, 1H), 7.78 (d, 1H), 7.01 (m, 1H), 6.94 (d, 1H), 6.51 (m, 2H), 6.30 (s, 1H), 6.17 (d, 1H), 5.78 (d, 1H), 4.44 (m, 1H), 3.38 (m, 1H), 3.27 (m, 1H), 3.10 (m, 1H), 3.03 (m, 1H), 2.15 (m, 1H), 1.90 (s, 3H), 1.75 (m, 1H)

Example 89: Preparation of 3-chloro-4-((4-fluoro-2-(3-methoxypyrrolidin-1-yl)phenyl)amino)-N-(thiazol-4-yl)benzenesulfonamide

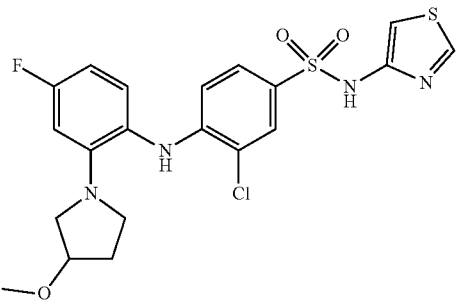 [SMILES: COC1CCN(c2cc(F)ccc2Nc2ccc(S(=O)(=O)Nc3cscn3)cc2Cl)C1]

1H NMR (500 MHz, CDCl$_3$): 10.74 (s, 1H), 8.77 (s, 1H), 7.72 (s, 1H), 7.42 (d, 1H), 7.01 (m, 2H), 6.53 (m, 3H), 6.18 (s, 1H), 3.90 (s, 1H), 3.34 (m, 2H), 3.25 (s, 3H), 3.12 (m, 2H), 1.99 (m, 1H), 1.89 (m, 1H)

Example 90: Preparation of 3-chloro-4-((2-(3-methoxypyrrolidin-1-yl)-4-(trifluoromethyl)phenyl)amino)-N-(thiazol-4-yl)benzenesulfonamide

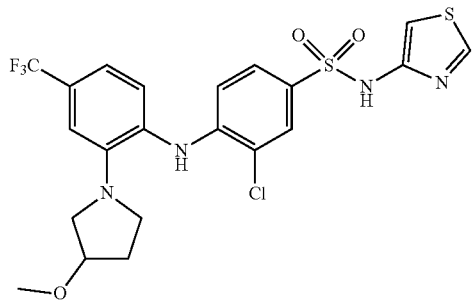 [SMILES: COC1CCN(c2cc(C(F)(F)F)ccc2Nc2ccc(S(=O)(=O)Nc3cscn3)cc2Cl)C1]

1H NMR (500 MHz, CDCl$_3$): 10.38 (s, 1H), 8.76 (s, 1H), 7.78 (s, 1H), 7.50 (d, 1H), 7.26 (d, 1H), 7.14 (m, 2H), 7.02 (s, 1H), 6.91 (d, 1H), 6.65 (s, 1H), 3.97 (s, 1H), 3.33 (m, 5H), 3.12 (m, 2H), 2.03 (m, 2H)

Example 91: Preparation of (R)—N-(1-(2-((2-chloro-4-(N-(thiazol-4-yl)sulfamoyl)phenyl)amino)-5-fluorophenyl)pyrrolidin-3-yl)acetamide

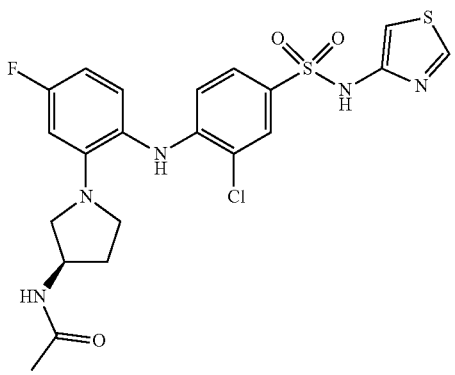 [SMILES: CC(=O)N[C@@H]1CCN(c2cc(F)ccc2Nc2ccc(S(=O)(=O)Nc3cscn3)cc2Cl)C1]

1H NMR (500 MHz, CDCl$_3$): 10.43 (broad, 1H), 8.76 (s, 1H), 7.71 (s 1H), 7.41 (s, 1H), 7.03 (s, 2H), 6.54 (m, 3H), 6.25 (s, 1H), 5.90 (s, 1H), 4.40 (s, 1H), 3.28 (m, 2H), 2.98 (m, 3H), 2.15 (m, 1H), 2.03-1.74 (m, 3H)

Example 92: Preparation of 5-chloro-2-fluoro-4-((4-fluoro-2-(methyl(2-(methylamino)ethyl)amino)phenyl)amino)-N-(thiazol-4-yl)benzenesulfonamide hydrochloride

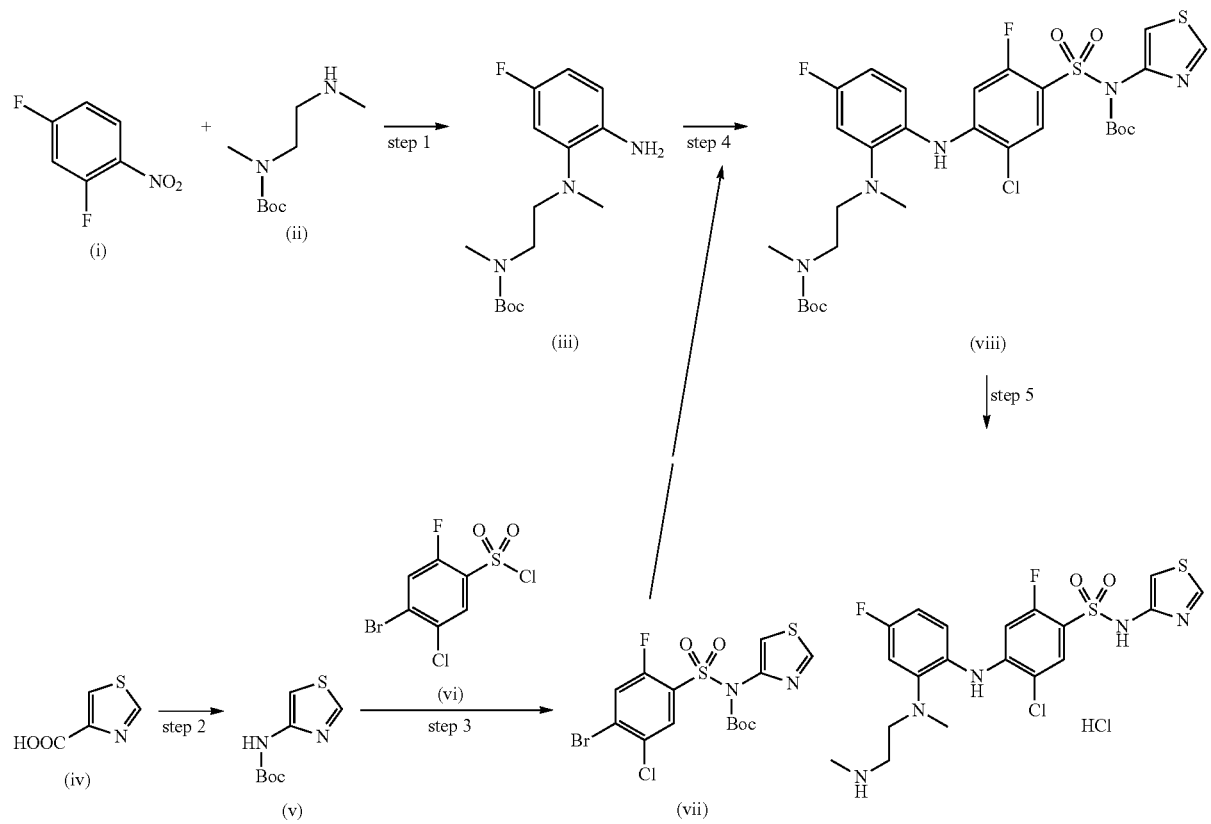

Step 1) Preparation of tert-butyl(2-((2-amino-5-fluorophenyl)(methyl)amino)ethyl)(methyl)carbamate (iii)

2,4-difluoro-1-nitrobenzene (i, 2.0 g, 12.6 mmol) and tert-butylmethyl(2-(methylamino)ethyl)carbamate (ii, 2.4 g, 1.0 eq.) were dissolved in DMF (20 mL), and then $K_2CO_3$ (2.6 g, 1.5 eq.) was added thereto. While maintaining the internal temperature at 60 to 70° C., the reaction mixture was stirred for 2 hours. When the reaction solution became dark yellow, the completion of the reaction was confirmed by TLC. After cooling to room temperature, $EA/H_2O$ was added and stirred, and then the layers were separated. $MgSO_4$ was added to the separated organic layer, which was stirred, filtered and then dried. The filtrate was concentrated under reduced pressure, and the residue was dissolved in MeOH (0.13 g, 0.1 eq.) and then Pd/C (0.13 g, 0.1 eq.) was added. The inside was replaced with hydrogen gas, and the reaction mixture was stirred at room temperature for 6 hours. When the yellow color of the reaction solution faded and became almost colorless, the completion of the reaction was confirmed by TLC. The metal catalyst was filtered through Celite. The filtrate was concentrated under reduced pressure, and the obtained residue was separated by column chromatography (Hx/EA=3/1) to obtain the target compound (iii, 2.5 g, 66.9%).

1H NMR (500 MHz, $CDCl_3$): 6.76 (d, 1H), 6.64 (m, 2H), 3.36 (m, 2H), 2.94 (m, 2H), 2.86 (m, 3H), 2.68 (s, 3H), 1.45 (s, 9H)

Step 2) Preparation of tert-butyl thiazol-4-yl carbamate (v)

Thiazol-4-carboxylic acid (iv, 5.0 g, 38.8 mmol) was dissolved in t-BuOH (100 mL), and then TEA (8.1 mL, 1.5 eq.) and DPPA (7.1 mL, 1.5 eq.) were added thereto. While maintaining the internal temperature at 90 to 100° C., the reaction mixture was stirred for 3 days, and then the completion of the reaction was confirmed by TLC. The reaction was concentrated under reduced pressure, to which $H_2O$ (50 mL) was added and extracted twice with ethyl acetate (EA, 100 mL). $MgSO_4$ was added to the organic layer, which was stirred, filtered and dried. The filtrate was concentrated under reduced pressure, and the residue was added to a small amount of EA and slurried. The resulting solid was filtered to obtain a white title compound (v, 4.0 g, 51.5%).

1H NMR (500 MHz, MeOD): 8.73 (s, 1H), 7.24 (s, 1H), 1.52 (s, 9H)

Step 3) Preparation of tert-butyl((4-bromo-5-chloro-2-fluorophenyl)sulfonyl)(thiazol-4-yl)carbamate (vii)

Tert-butyl thiazol-4-yl carbamate (v, 4.0 g, 20.0 mmol) was added to a reaction vessel and the inside of the vessel was replaced with nitrogen gas. After dissolving in THF (32 mL), the solution was cooled to −78° C. using dry ice-acetone. After cooling, LiHMDS (22.4 mL, 1.5 eq.) was slowly added and the reaction mixture was stirred for 30 minutes. Then, 4-bromo-5-chloro-2-fluorobenzenesulfonyl chloride (vi, 6.0 g, 1.0 eq.) was dissolved in THF (10 mL) and then slowly added to the reaction solution. The reaction mixture was stirred overnight and the completion of the reaction was confirmed by TLC. $H_2O$ (50 mL) was added and extracted twice with ethyl acetate (EA, 100 mL). $MgSO_4$ was added to the organic layer, which was stirred, filtered and dried. The filtrate was concentrated under reduced pressure, and the residue was crystallized with THF/n-hexane to obtain the title compound (vii, 4.4 g, 59.0%).

1H NMR (500 MHz, MeOD): 9.00 (s, 1H), 8.22 (d, 1H), 7.90 (d, 1H), 7.78 (s, 1H), 1.35 (s, 9H)

Step 4) Preparation of tert-butyl(2-((2-((4-(N-(tert-butoxycarbonyl)-N-(thiazol-4-yl)sulfamoyl)-2-chloro-5-fluorophenyl)amino)-5-fluorophenyl)(methyl)amino)ethyl(methyl)carbamate (viii)

Tert-butyl (2-((2-amino-5-fluorophenyl)(methyl)amino) ethyl(methyl)carbamate (iii, 10.0 g, 33.7 mmol) and tert-butyl ((4-bromo-5-chloro-2-fluorophenyl)sulfonyl)(thiazol-4-yl)carbamate (vii, 13.0 g, 1.0 eq.) were dissolved in 1,4-dioxane (200 mL). $Pd(OAc)_2$ (0.7 g, 0.1 eq), rac-BINAP (4.11 g, 0.2 eq.), and $Cs_2CO_3$ (21.2 g, 2.0 eq.) were added to the reaction solution. While maintaining the internal temperature at 90 to 100° C., the reaction mixture was stirred for 5 hours, and then the completion of the reaction was confirmed by TLC. $H_2O$ (100 mL) was added and extracted twice with ethyl acetate (EA, 1000 mL). $MgSO_4$ was added to the organic layer, which was stirred, filtered and then dried. The filtrate was concentrated under reduced pressure, and the residue was separated by column chromatography using a mobile phase of EA/Hex=1/4 to obtain the title compound (16.0 g, 69.1%).

1H NMR (500 MHz, MeOD): 8.95 (d, 1H), 7.96 (d, 1H), 7.68 (s, 1H), 7.26 (s, 1H), 6.95 (t, 1H), 6.8 (s, 1H), 6.39 (s, 1H), 3.27 (s, 2H), 3.14 (s, 2H), 2.79 (s, 3H), 2.70 (d, 3H), 1.40 (s, 9H), 1.37 (s, 9H)

Step 5) Preparation of 5-chloro-2-fluoro-4-((4-fluoro-2-(methyl(2-(methylamino)ethyl)amino)phenyl)amino)-N-(thiazol-4-yl)benzenesulfonamide hydrochloride To tert-butyl (2-((2-((4-(N-(tert-butoxycarbonyl)-N-(thiazol-4-yl)sulfamoyl)-2-chloro-5-fluorophenyl)amino)-5-fluorophenyl)(methyl)amino)ethyl(methyl)carbamate (vii, 14.0 g, 20.3 mmol) was added 1 M HCl in ethyl acetate (200 mL). After stirring the mixture stirred overnight while heating to 50 to 60° C., the completion of the reaction was confirmed by TLC. The reaction solution was filtered, and MC (200 mL) was added to the obtained residue and stirred for 1 hour. The resulting solid was filtered to obtain the target compound (9.1 g, 85.3%).

1H NMR (500 MHz, MeOD): 8.73 (d, 1H), 7.79 (d, 1H), 7.26 (dd, 1H), 7.03 (m, 2H), 6.90 (td, 1H), 6.43 (d, 1H), 3.26 (t, 2H), 3.09 (t, 2H), 2.70 (s, 3H), 2.65 (s, 3H)

Example 93: Preparation of 3-chloro-4-((2-((2-(dimethylamino)ethyl)(methyl)amino)-4-fluorophenyl)amino)-N-(thiazol-4-yl)benzenesulfonamide

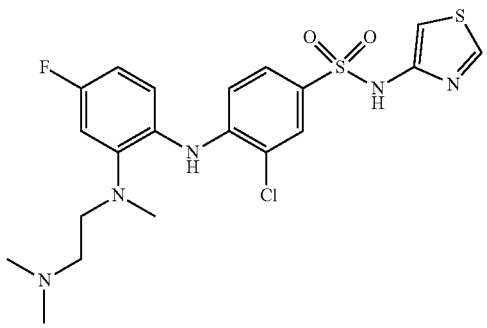 [SMILES: CN(C)CCN(C)c1cc(F)ccc1Nc1ccc(S(=O)(=O)Nc2cscn2)cc1Cl]

An intermediate was prepared in the same manner as described in Example 92, except that N,N,N'-trimethyl-ethane-1,2-diamine was used instead of tert-butyl methyl(2-(methylamino)ethyl)carbamate (ii) and 4-bromo-5-chlorobenzene sulfonyl chloride was used instead of 4-bromo-5-chloro-2-fluorobenzenesulfonnyl chloride (vi). To the obtained intermediate tert-butyl ((3-chloro-4-((2-((-(dimethylamino)ethyl)(methyl)amino)-4-fluorophenyl)amino)phenyl)sulfonyl)(thiazol-4-yl)carbamate (0.05 g, 0.09 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 48.0%).

1H NMR (500 MHz, MeOD): 8.73 (s, 1H), 7.81 (s, 1H), 7.54 (d, 1H), 7.21 (dd, 1H), 7.00 (m, 2H), 6.82 (dd, 1H), 6.75 (d, 1H), 3.20 (t, 2H), 2.93 (t, 2H), 2.70 (s, 3H), 2.55 (s, 3H)

Example 94: Preparation of 5-chloro-4-((2-((2-(dimethylamino)ethyl)(methyl)amino)-4-fluorophenyl) amino)-2-fluoro-N-(thiazol-4-yl)benzenesulfonamide

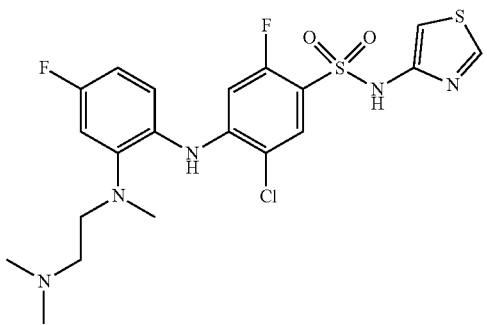

An intermediate was prepared in the same manner as described in Example 92, except that N,N,N'-trimethyl-ethane-1,2-diamine was used instead of tert-butyl methyl(2-(methylamino)ethyl)carbamate (ii). To the obtained intermediate tert-butyl ((5-chloro-4-((2-(dimethylamino)ethyl)(methyl)amino)-4-fluorophenyl)amino)-2-fluorophenyl)sulfonyl)(thiazol-4-yl)carbamate (0.05 g, 0.08 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 49.8%).

1H NMR (500 MHz, MeOD): 8.72 (s, 1H), 7.76 (d, 1H), 7.2 (t, 1H), 6.95 (m, 2H), 6.80 (t, 1H), 6.38 (d, 1H), 3.01 (t, 2H), 2.68 (s, 3H), 2.40 (t, 2H), 2.15 (s, 3H)

Example 95: Preparation of 5-chloro-2-fluoro-4-((2-(methyl(2-(methylamino)ethyl)amino)-4-(trifluoromethyl)phenyl)amino)-N-(thiazol-4-yl)benzenesulfonamide hydrochloride

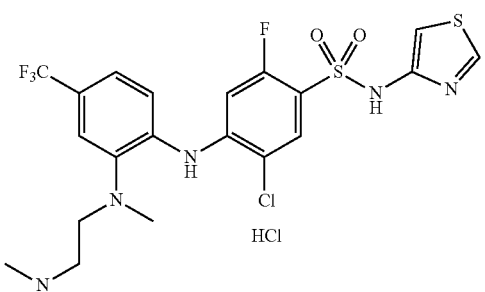

An intermediate was prepared in the same manner as described in Example 92, except that 2-fluoro-1-nitro-4-(trifluoromethyl)benzene was used instead of 2,4-difluoro-1-nitrobenzene (i). To the obtained intermediate tert-butyl (2-((2-((4-(N-(tert-butoxycarbonyl)-N-(thiazol-4-yl)sulfamoyl)-2-chloro-5-fluorophenyl)amino)-5-(trifluoromethyl) phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 55.5%).

1H NMR (500 MHz, MeOD): 8.74 (s, 1H), 7.88 (d, 1H), 7.54 (s, 1H), 7.42 (m, 2H), 7.06 (s, 1H), 7.02 (d, 1H), 3.35 (t, 2H), 3.16 (t, 2H), 2.73 (s, 3H), 2.70 (s, 3H)

Example 96: Preparation of 5-chloro-2-fluoro-4-((4-fluoro-2-(methyl(2-(methylamino)ethyl)amino)phenyl)amino)-N-(5-fluoropyrimidin-2-yl)benzenesulfonamide hydrochloride

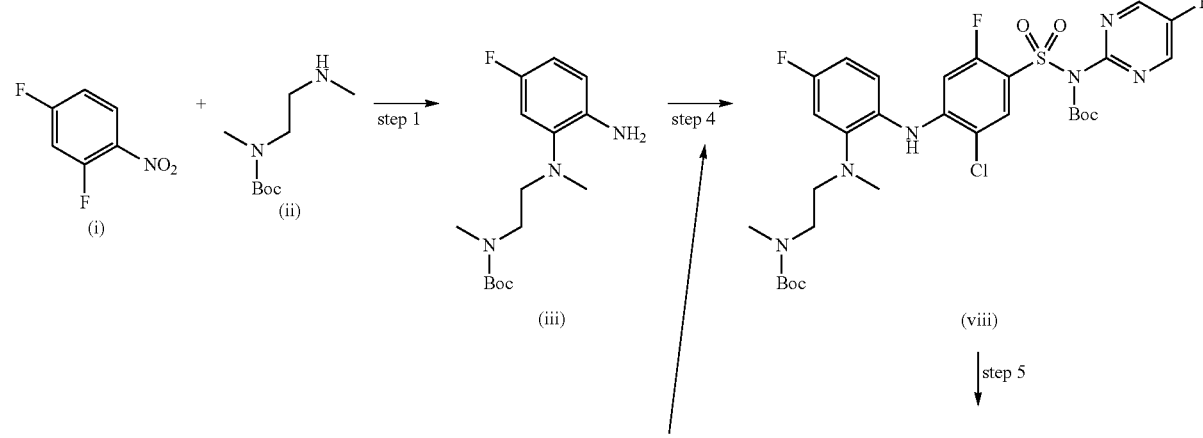

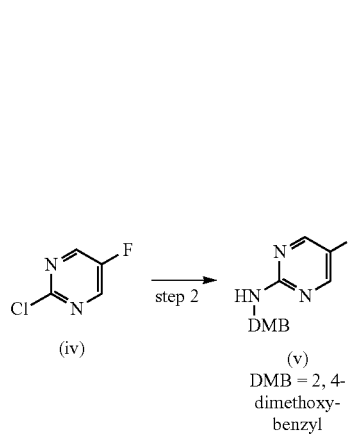 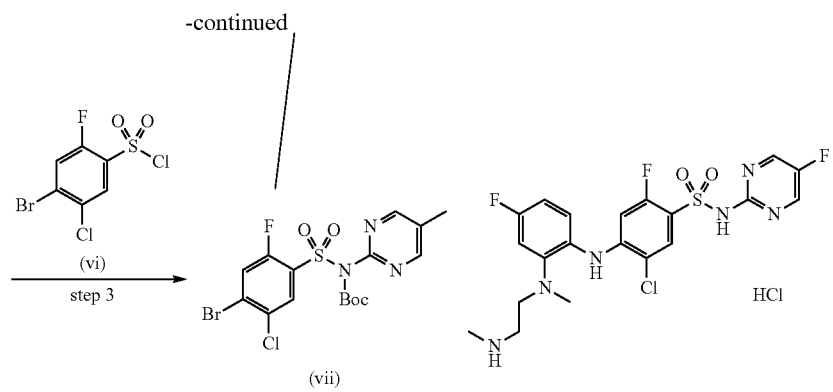

N-(2,4-dimethoxybenzyl)-5-fluoropyrimidin-2-amine (v) was prepared instead of the step 2 of Example 92. Specifically, 2-chloro-5-fluoropyrimidine (iv, 0.48 g, 3.62 mmol), (2,4-dimethoxyphenyl)methaneamine (0.60 g, 1.0 eq.) and trimethylamine (0.76 mL, 1.5 eq.) were dissolved in EtOH (10 mL). After stirring the mixture stirred overnight while heating to 70 to 80° C., the completion of the reaction was confirmed by TLC. The solution was concentrated under reduced pressure, and the obtained residue was separated by column chromatography using a mobile phase of EA/Hex=1/2 to obtain 0.32 g (yield 34%) of the target compound (v).

1H NMR (500 MHz, MeOD): 8.20 (s, 2H), 7.13 (d, 1H), 6.51 (s, 1H), 6.41 (d, 1H), 4.44 (s, 2H), 3.82 (s, 3H), 3.76 (s, 3H)

The target compound was prepared in the same manner as described in steps 1, 3, 4 and 5 of Example 92, except that N-(2,4-dimethoxybenzyl)-5-fluoropyrimidin-2-amine prepared above was used instead of tert-butylthiazol-4-ylcarbamate (v) in Example 92.

1H NMR (500 MHz, MeOD): 8.43 (m, 2H), 7.99 (t, 1H), 7.27 (dd, 1H), 7.03 (d, 1H), 6.88 (t, 1H), 6.45 (d, 1H), 3.20 (t, 2H), 3.10 (t, 2H), 2.71 (s, 3H), 2.67 (s, 3H)

Example 97: Preparation of 5-chloro-2-fluoro-N-(5-fluoropyrimidin-2-yl)-4-((2-(methyl(2-(methylamino)ethyl)amino)-4-(trifluoromethyl)phenyl)amino)benzenesulfonamide hydrochloride

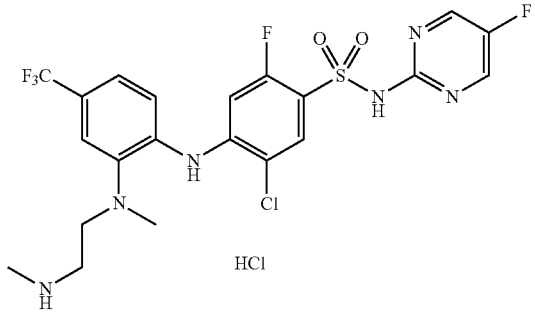 [SMILES: CNCCN(C)c1cc(C(F)(F)F)ccc1Nc1cc(F)c(S(=O)(=O)Nc2ncc(F)cn2)cc1Cl ; Cl]

An intermediate was prepared in the same manner as described in Example 96, except that 2-fluoro-1-nitro-4-(trifluoromethyl)benzene was used instead of 2,4-difluoro-1-nitrobenzene (i). To the obtained intermediate tert-butyl (2-((2-((2-chloro-4-(N-(2,4-dimethoxybenzyl)-N-(5-fluoropyrimidin-2-yl)sulfamoyl)-5-fluorophenyl)amino)-5-(trifluoromethyl)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.3%).

1H NMR (500 MHz, MeOD): 8.47 (s, 1H), 8.29 (s, 1H), 8.05 (m, 1H), 7.53 (d, 1H), 7.41 (m, 2H), 7.01 (t, 1h), 3.45 (t, 2H), 3.16 (t, 2H), 2.74 (s, 3H), 2.69 (s, 3H)

Example 98: Preparation of 5-chloro-4-((4-(difluoromethoxy)-2-(methyl(2-(methylamino)ethyl)amino)phenyl)amino)-2-fluoro-N-(thiazol-4-yl)benzenesulfonamide hydrochloride

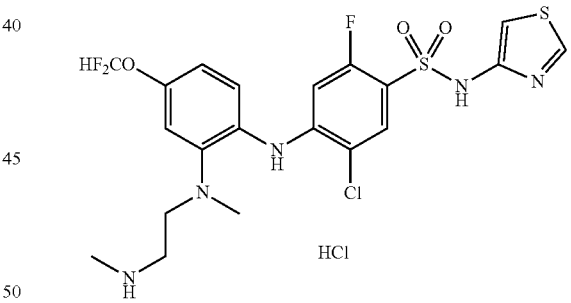

An intermediate was prepared in the same manner as described in Example 92, except that 4-(difluoromethoxy)-2-fluoro-1-nitrobenzene was used instead of 2,4-difluoro-1-nitrobenzene (i). To the obtained intermediate tert-butyl (2-((2-((4-(N-(tert-butoxycarbonyl)-N-(thiazol-4-yl)sulfamoyl)-2-chloro-5-fluorophenyl)amino)-5-(difluoromethoxy)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 55.7%).

1H NMR (500 MHz, MeOD): 8.73 (s, 1H), 7.80 (d, 1H), 7.29 (d, 1H), 7.02 (s, 2H), 6.94 (d, 1H), 6.85 (t, 1H), 6.55 (d, 1H), 3.25 (t, 2H), 3.10 (t, 2H), 2.70 (s, 3H), 2.66 (s, 3H)

Example 99: Preparation of 5-chloro-4-((4-cyano-2-(methyl(2-(methylamino)ethyl)amino)phenyl)amino)-2-fluoro-N-(thiazol-4-yl)benzenesulfonamide hydrochloride

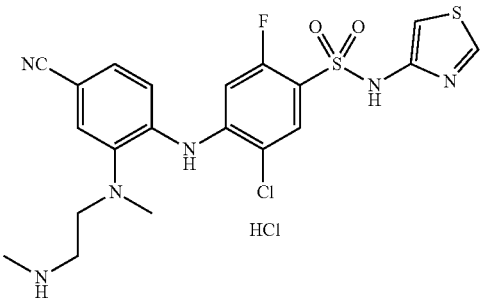 [SMILES: CNCCN(C)c1cc(C#N)ccc1Nc1cc(F)c(S(=O)(=O)Nc2cscn2)cc1Cl ; Cl]

An intermediate was prepared in the same manner as described in Example 92, except that 3-fluoro-4-nitrobenzonitrile was used instead of 2,4-difluoro-1-nitrobenzene (i). To the obtained intermediate tert-butyl (2-((2-((4-(N-(tert-butoxycarbonyl)-N-(thiazol-4-yl)sulfamoyl)-2-chloro-5-fluorophenyl)amino)-5-cyanophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.1%).

1H NMR (500 MHz, MeOD): 8.75 (s, 1H), 7.91 (d, 1H), 7.62 (d, 1H), 7.47 (t, 1H), 7.32 (d, 1H), 7.17 (d, 1H), 7.07 (d, 1H), 3.28 (t, 2H), 3.17 (t, 2H), 2.71 (s, 3H), 2.70 (s, 3H)

Example 100: Preparation of 5-chloro-4-((4-cyano-2-(methyl(2-(methylamino)ethyl)amino)phenyl)amino)-2-fluoro-N-(5-fluoropyrimidin-2-yl)benzenesulfonamide hydrochloride

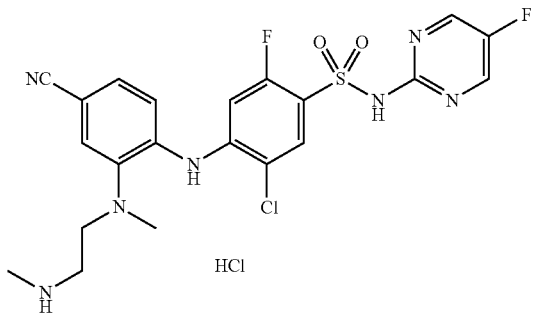

An intermediate was prepared in the same manner as described in Example 96, except that 3-fluoro-4-nitrobenzonitrile was used instead of 2,4-difluoro-1-nitrobenzene (i). To the obtained intermediate tert-butyl (2-((2-((2-chloro-4-(N-(2,4-dimethoxybenzyl)-N-(5-fluoropyrimidin-2-yl)sulfamoyl)-5-fluorophenyl)amino)-5-cyanophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.7%).

1H NMR (500 MHz, MeOD): 8.43 (s, 2H), 8.10 (d, 1H), 7.63 (s, 1H), 7.48 (d, 1H), 7.36 (d, 1H), 7.17 (d, 1H), 3.34-3.32 (m, 2H), 3.19-3.16 (m, 2H), 2.72 (s, 3H), 2.71 (s, 3H)

Example 101: Preparation of 5-chloro-4-((4-(difluoromethoxy)-2-(methyl(2-(methylamino)ethyl)amino)phenyl)amino)-2-fluoro-N-(5-fluoropyrimidin-2-yl)benzenesulfonamide hydrochloride

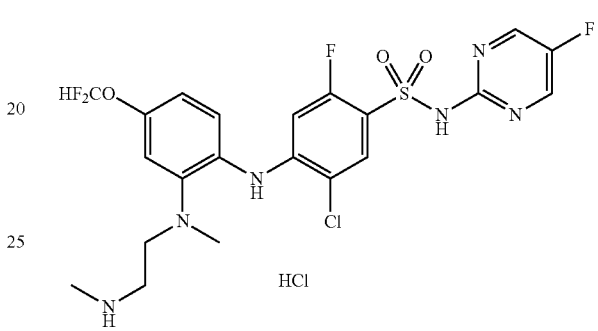

An intermediate was prepared in the same manner as described in Example 96, except that 4-(difluoromethoxy)-2-fluoro-1-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluoropyrimidin-2-yl)sulfamoyl)-5-fluorophenyl)amino)-5-(difluoromethoxy)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.2%).

1H NMR (500 MHz, MeOD): 8.42 (s, 2H), 8.01 (d, 1H), 7.33-7.17 (m, 3H), 6.71 (d, 1H), 3.35-3.32 (m, 2H), 3.13-3.10 (m, 2H), 2.68 (s, 3H), 2.67 (s, 3H)

Example 102: Preparation of 5-chloro-2-fluoro-N-(5-fluoropyrimidin-2-yl)-4-((2-(methyl(2-(methylamino)ethyl)amino)phenyl)amino)benzenesulfonamide hydrochloride

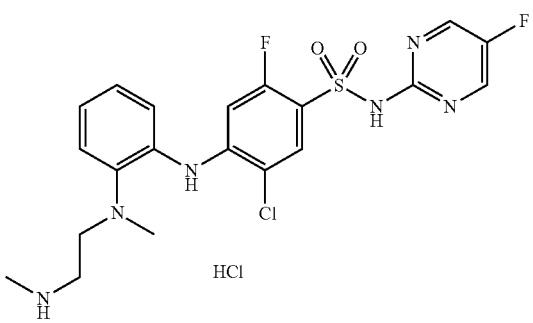 [SMILES: CNCCN(C)c1ccccc1Nc1cc(F)c(S(=O)(=O)Nc2ncc(F)cn2)cc1Cl ; Cl]

An intermediate was prepared in the same manner as described in Example 96, except that 1-fluoro-2-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluoropyrimidin-2-yl)sulfamoyl)-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 60.7%).

1H NMR (500 MHz, MeOD): 8.42 (s, 2H), 8.00 (d, 1H), 7.30 (d, 1H), 7.03 (d, 1H), 6.94 (d, 1H), 6.69 (s, 1H), 6.52 (d, 1H), 3.34-3.32 (m, 2H), 3.12-3.10 (m, 2H), 2.70 (s, 3H), 2.67 (s, 3H)

Example 103: Preparation of 5-chloro-2-fluoro-4-((4-fluoro-2-(methyl(2-(methylamino)ethyl)amino)phenyl)amino)-N-(5-fluoropyridin-2-yl)benzenesulfonamide hydrochloride N-(2,4-dimethoxybenzyl)-5-fluoropyridin-2-amine (v) was prepared instead of the step 2 of Example 92. Specifically, 5-fluoropyridin-2-amine (iv, 0.55 g, 0.01 mmol) and 2,4-dimethoxybenzalhehyde (0.45 g, 0.9 eq.) were dissolved in DCM (10 mL). After stirring at room temperature for 1 hour, sodium triacetoxyborohydride (1.0 g, 1 eq.) was added three times at 15 minute intervals. After stirring the mixture stirred overnight, the completion of the reaction was confirmed by TLC. H$_2$O (10 mL) was added and extracted twice with dichloromethane (10 mL). MgSO$_4$ was added to the organic layer, which was stirred, filtered and dried. The filtrate was concentrated under reduced pressure, and then the resulting residue was separated by column chromatography using a mobile phase of EA/Hex=1/4 to obtain 0.65 g (yield 51%) of N-(2,4-dimethoxybenzyl)-5-fluoropyridin-2-amine (v).

1H NMR (500 MHz, CDCl$_3$): 7.90 (d, 1H), 7.16 (m, 2H), 6.46 (d, 1H), 6.41 (d, 1H), 6.34 (m, 1H), 4.36 (s, 2H), 3.81 (s, 3H), 3.77 (s, 3H)

The target compound was prepared in the same manner as described in steps 1, 3, 4 and 5 of Example 92, except that N-(2,4-dimethoxybenzyl)-5-fluoropyridin-2-amine prepared above was used instead of tert-butylthiazol-4-ylcarbamate (v) in Example 92.

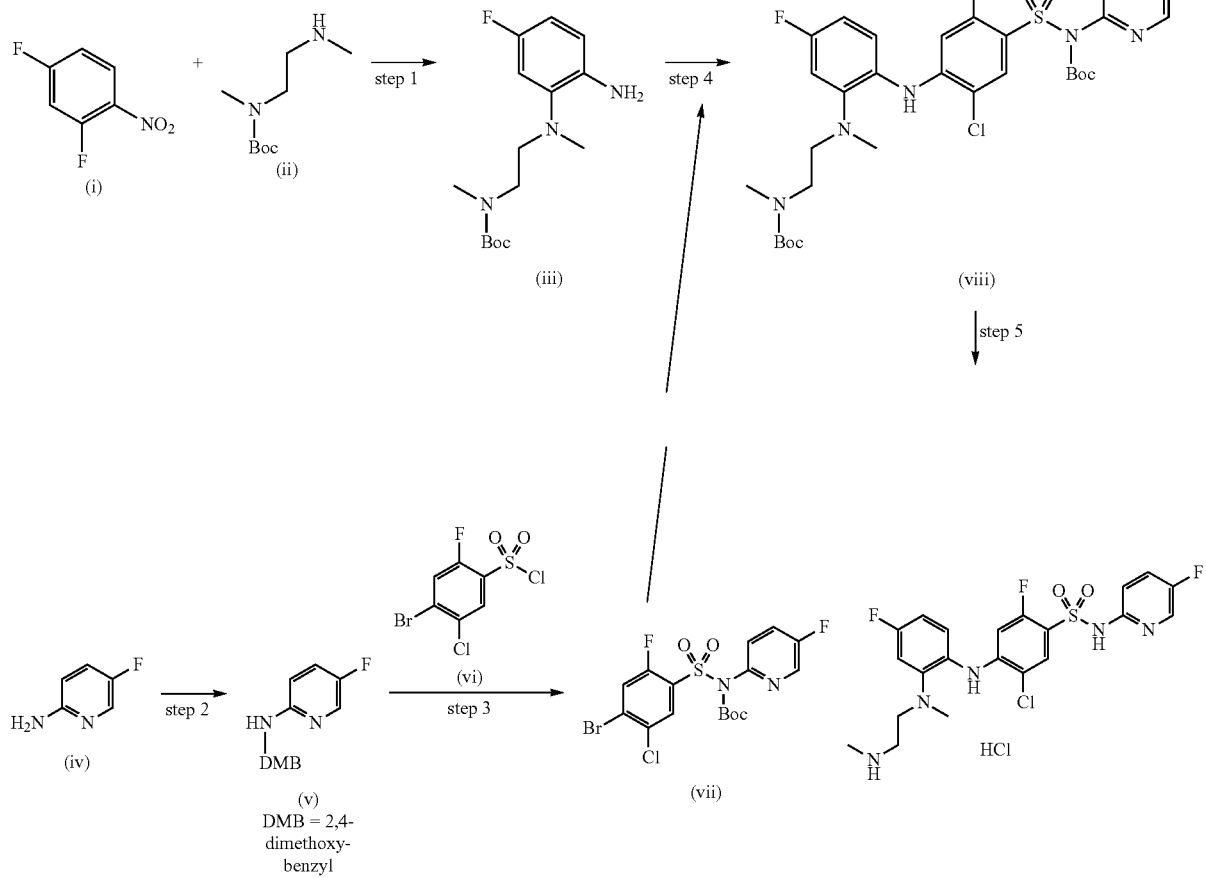

1H NMR (500 MHz, MeOD): 8.05 (d, 1H), 7.89 (d, 1H), 7.51 (d, 1H), 7.26-6.87 (m, 4H), 6.42 (d, 1H), 3.38-3.25 (m, 2H), 3.10-3.09 (m, 2H), 2.69 (s, 3H), 2.65 (s, 3H)

Example 104: Preparation of 5-chloro-2-fluoro-4-((4-fluoro-2-(methyl(2-(methylamino)ethyl)amino)phenyl)amino)-N-(pyridin-2-yl)benzenesulfonamide hydrochloride

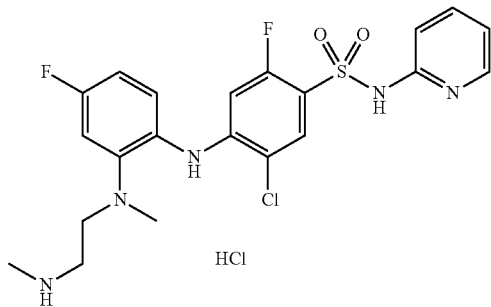 [SMILES: CNCCN(C)c1cc(F)ccc1Nc1cc(F)c(S(=O)(=O)Nc2ccccn2)cc1Cl ; Cl]

An intermediate was prepared in the same manner as described in Example 103, except that pyridine-2-amine was used instead of 5-fluoropyridin-2-amine (iv). To the obtained intermediate tert-butyl (2-((5-chloro-2-((2-chloro-4-(N-(2,4-dimethoxybenzyl)-N-(pyridin-2-yl)sulfamoyl)-5-fluorophenyl)amino)phenyl)(methyl)amino)ethyl)(methyl) carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 60.0%).

1H NMR (500 MHz, MeOD): 8.01-7.92 (m, 2H), 7.29-7.24 (m, 3H), 7.03 (d, 2H), 6.87 (d, 1H), 6.46 (d, 1H), 3.42-3.40 (m, 2H), 3.11-3.08 (m, 2H), 2.70 (s, 3H), 2.66 (s, 3H)

Example 105: Preparation of 5-chloro-2-fluoro-4-((4-fluoro-2-(methyl(2-(methylamino)ethyl)amino)phenyl)amino)-N-(thiazol-2-yl)benzenesulfonamide hydrochloride

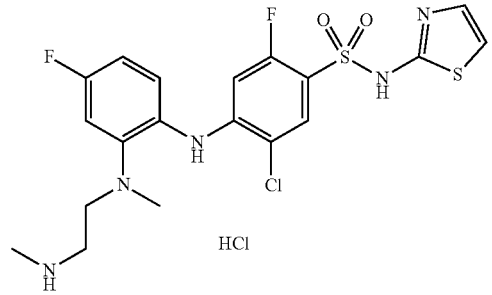 [SMILES: CNCCN(C)c1cc(C#N)ccc1Nc1cc(F)c(S(=O)(=O)Nc2nccs2)cc1Cl ; Cl]

An intermediate was prepared in the same manner as described in Example 103, except that thiazole-2-amine was used instead of 5-fluoropyridin-2-amine (iv). To the obtained intermediate tert-butyl (2-((5-chloro-2-((2-chloro-4-(N-(2,4-dimethoxybenzyl)-N-(thiazol-2-yl)sulfamoyl)-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.8%).

1H NMR (500 MHz, MeOD): 7.84 (d, 2H), 7.28-7.04 (m, 3H), 6.89 (d, 1H), 6.74 (d, 1H), 6.46 (d, 1H), 3.26-3.24 (m, 2H), 3.11-3.08 (m, 2H), 2.71 (s, 3H), 2.66 (s, 3H)

Example 106: Preparation of 5-chloro-4-((4-cyano-2-(methyl(2-(methylamino)ethyl)amino)phenyl)amino)-2-fluoro-N-(5-fluoropyridin-2-yl)benzenesulfonamide hydrochloride

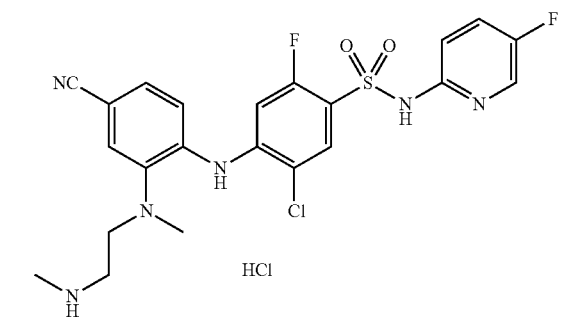 [SMILES: CNCCN(C)c1cc(C(F)(F)F)ccc1Nc1cc(F)c(S(=O)(=O)Nc2ccc(F)cn2)cc1Cl ; Cl]

An intermediate was prepared in the same manner as described in Example 103, except that 3-fluoro-4-nitrobenzonitrile was used instead of 2,4-difluoro-1-nitrobenzene (i). To the obtained intermediate tert-butyl (2-((2-((2-chloro-4-(N-(2,4-dimethoxybenzyl)-N-(5-fluoropyridin-2-yl)sulfamoyl)-5-fluorophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.0%).

1H NMR (500 MHz, MeOD): 8.05-8.01 (m, 2H), 7.62 (s, 1H), 7.55-7.46 (m, 2H), 7.33 (d, 1H), 7.14 (d, 1H), 3.34-3.32 (m, 2H), 3.18-3.17 (m, 2H), 2.72 (s, 3H), 2.71 (s, 3H)

Example 107: Preparation of 5-chloro-4-((4-cyano-2-(methyl(2-(methylamino)ethyl)amino)phenyl)amino)-2-fluoro-N-(pyridin-2-yl)benzenesulfonamide hydrochloride

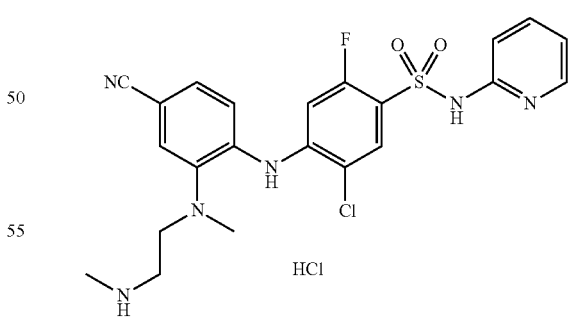

An intermediate was prepared in the same manner as described in Example 103, except that 3-fluoro-4-nitrobenzonitrile was used instead of 2,4-difluoro-1-nitrobenzene (i), and pyridine-2-amine was used instead of 5-fluoropyridin-2-amine (iv). To the obtained intermediate tert-butyl (2-((2-((2-chloro-4-(N-(2,4-dimethoxybenzyl)-N-(pyridin-2-yl)sulfamoyl)-5-fluorophenyl)amino)-5-cyanophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 57.2%).

1H NMR (500 MHz, MeOD): 8.05 (d, 1H), 7.97-7.86 (s, 2H), 7.62 (s, 1H), 7.46 (d, 1H), 7.33-7.19 (m, 3H), 7.01-6.97 (m, 1H), 3.32-3.31 (m, 2H), 3.19-3.16 (m, 2H), 2.72 (s, 3H), 2.71 (s, 3H)

Example 108: Preparation of 5-chloro-4-((4-cyano-2-(methyl(2-(methylamino)ethyl)amino)phenyl)amino)-2-fluoro-N-(thiazol-2-yl)benzenesulfonamide hydrochloride

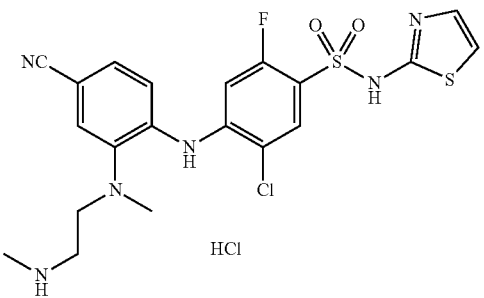

An intermediate was prepared in the same manner as described in Example 103, except that 3-fluoro-4-nitrobenzonitrile was used instead of 2,4-difluoro-1-nitrobenzene (i), and thiazole-2-amine was used instead of 5-fluoropyridin-2-amine (iv). To the obtained intermediate tert-butyl (2-((2-((2-chloro-4-(N-(2,4-dimethoxybenzyl)-N-(thiazol-2-yl)sulfamoyl)-5-fluorophenyl)amino)-5-cyanophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 60.2%).

1H NMR (500 MHz, MeOD): 7.96 (d, 1H), 7.62 (s, 1H), 7.46 (d, 1H), 7.28-7.14 (m, 3H), 6.77 (d, 1H), 3.32-3.30 (m, 2H), 3.20-3.17 (m, 2H), 2.72 (s, 3H), 2.71 (s, 3H)

Example 109: Preparation of 5-chloro-2-fluoro-N-(5-fluoropyridin-2-yl)-4-((2-(methyl(2-(methylamino)ethyl)amino)-4-(trifluoromethyl)phenyl)amino)benzenesulfonamide hydrochloride

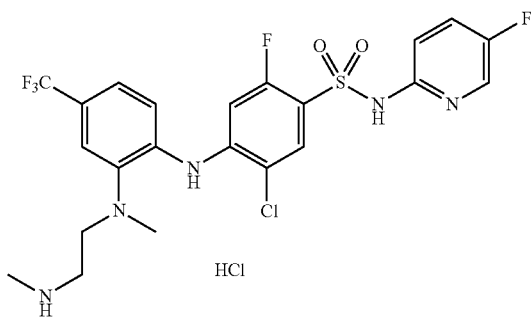

An intermediate was prepared in the same manner as described in Example 103, except that 2-fluoro-1-nitro-4-(trifluoromethyl)benzene was used instead of 2,4-difluoro-1-nitrobenzene (i). To the obtained intermediate tert-butyl (2-((2-((2-chloro-4-(N-(2,4-dimethoxybenzyl)-N-(5-fluoropyridin-2-yl)sulfamoyl)-5-fluorophenyl)amino)-5-(trifluoromethyl)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.2%).

1H NMR (500 MHz, MeOD): 8.05 (d, 1H), 7.99 (d, 1H), 7.53 (m, 2H), 7.43 (s, 2H), 7.17 (m, 1H), 7.02 (d, 1H), 3.47 (t, 2H), 3.17 (t, 2H), 2.74 (s, 3H), 2.70 (s, 3H)

Example 110: Preparation of 5-chloro-2-fluoro-4-((2-(methyl(2-(methylamino)ethyl)amino)-4-(trifluoromethyl)phenyl)amino)-N-(pyridin-2-yl)benzenesulfonamide hydrochloride

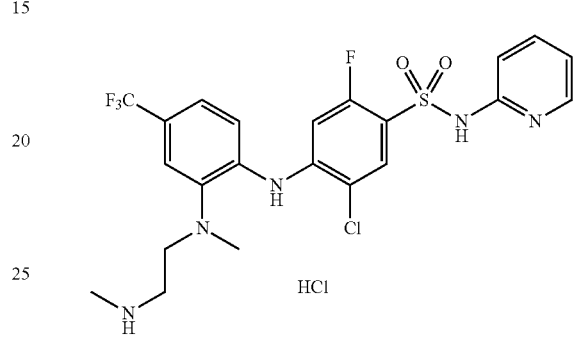

An intermediate was prepared in the same manner as described in Example 103, except that 2-fluoro-1-nitro-4-(trifluoromethyl)benzene was used instead of 2,4-difluoro-1-nitrobenzene (i) and pyridin-2-amine was used instead of 5-fluoropyridin-2-amine (iv). To the obtained intermediate tert-butyl (2-((2-((2-chloro-4-(N-(2,4-dimethoxybenzyl)-N-(pyridin-2-yl)sulfamoyl)-5-fluorophenyl)amino)-5-(trifluoromethyl)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.8%).

1H NMR (500 MHz, MeOD): 8.02 (d, 1H), 7.98 (t, 1H), 7.86 (t 1H), 7.53 (s, 1H), 7.40 (m, 2H), 7.31 (d, 1H), 7.05 (d, 1H), 6.99 (m, 1H), 3.34 (t, 2H), 3.17 (t, 2H), 2.74 (s, 3H), 2.71 (s, 3H)

Example 111: Preparation of 5-chloro-2-fluoro-4-((2-(methyl(2-(methylamino)ethyl)amino)-4-(trifluoromethyl)phenyl)amino)-N-(thiazol-2-yl)benzenesulfonamide hydrochloride

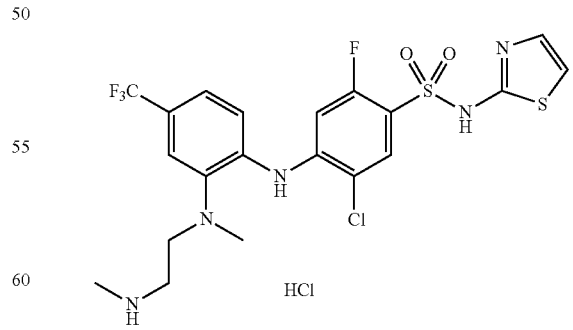

An intermediate was prepared in the same manner as described in Example 103, except that 2-fluoro-1-nitro-4-(trifluoromethyl)benzene was used instead of 2,4-difluoro-1-nitrobenzene (i) and thiazol-2-amine was used instead of 5-fluoropyridin-2-amine (iv). To the obtained intermediate tert-butyl (2-((2-((2-chloro-4-(N-(2,4-dimethoxybenzyl)-N-(thiazol-2-yl)sulfamoyl)-5-fluorophenyl)amino)-5-(trifluoromethyl)phenyl)(methyl)amino) ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.6%).

1H NMR (500 MHz, MeOD): 7.93 (d, 1H), 7.53 (s, 1H), 7.41 (m, 2H), 7.13 (d, 1H), 7.07 (d, 1H), 6.77 (d, 1H), 3.34 (t, 2H), 3.18 (t, 2H), 2.75 (s, 3H), 2.71 (s, 3H)

Example 112: Preparation of 5-chloro-2-fluoro-N-(5-fluoropyridin-2-yl)-4-((2-(methyl(2-(methylamino)ethyl)amino)phenyl)amino)benzenesulfonamide hydrochloride

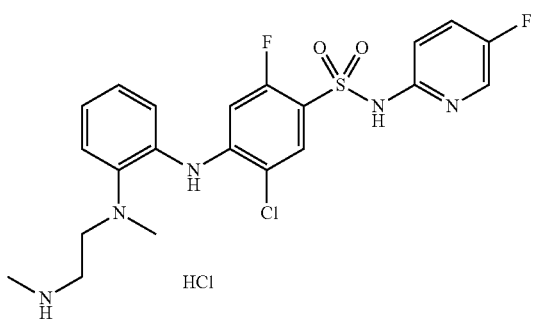 [SMILES: CNCCN(C)c1ccccc1Nc1cc(F)c(S(=O)(=O)Nc2ccc(F)cn2)cc1Cl ; Cl]

An intermediate was prepared in the same manner as described in Example 103, except that 1-fluoro-2-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluoropyridin-2-yl)sulfamoyl)-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 61.3%).

1H NMR (500 MHz, MeOD): 8.06 (d, 1H), 7.91 (d, 1H), 7.51 (m, 1H), 7.30 (m, 2H), 7.22 (t, 1H), 7.15 (m, 2H), 6.70 (d, 1H), 3.26 (t, 2H), 3.11 (t, 2H), 2.67 (s, 6H)

Example 113: Preparation of 5-chloro-2-fluoro-4-((2-(methyl(2-(methylamino)ethyl)amino)phenyl)amino)-N-(pyridin-2-yl)benzenesulfonamide hydrochloride

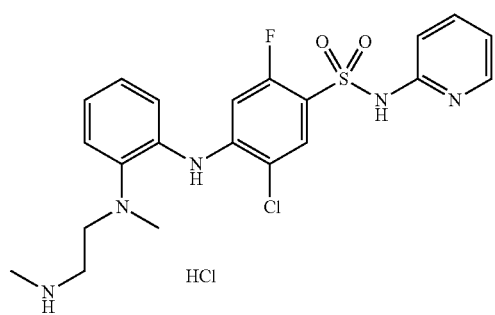 [SMILES: CNCCN(C)c1ccccc1Nc1cc(F)c(S(=O)(=O)Nc2ccccn2)cc1Cl ; Cl]

An intermediate was prepared in the same manner as described in Example 103, except that 1-fluoro-2-nitrobenzene was used instead of 2,4-difluoro-1-nitrobenzene (i) and pyridine-2-amine was used instead of 5-fluoropyridin-2-amine (iv). To the obtained intermediate tert-butyl (2-((2-((2-chloro-4-(N-(2,4-dimethoxybenzyl)-N-(pyridin-2-yl) sulfamoyl)-5-fluorophenyl)amino)phenyl)(methyl)amino) ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 61.6%).

1H NMR (500 MHz, MeOD): 8.03 (d, 1H), 7.96 (d, 1H), 7.90 (d, 1H), 7.30 (t, 3H), 7.23 (t, 1H), 7.17 (t, 1H), 7.04 (m, 1H), 6.73 (d, 1H), 3.26 (t, 2H), 3.12 (t, 2H), 2.68 (s, 3H), 2.67 (s, 3H)

Example 114: Preparation of 5-chloro-2-fluoro-4-((2-(methyl(2-(methylamino)ethyl)amino)phenyl)amino)-N-(thiazol-2-yl)benzenesulfonamide hydrochloride

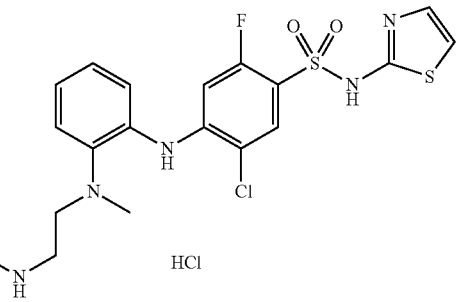

An intermediate was prepared in the same manner as described in Example 103, except that 1-fluoro-2-nitrobenzene was used instead of 2,4-difluoro-1-nitrobenzene (i) and thiazol-2-amine was used instead of 5-fluoropyridin-2-amine (iv). To the obtained intermediate tert-butyl (2-((2-((2-chloro-4-(N-(2,4-dimethoxybenzyl)-N-(thiazol-2-yl) sulfamoyl)-5-fluorophenyl)amino)phenyl)(methyl)amino) ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 61.3%).

1H NMR (500 MHz, MeOD): 7.86 (d, 1H), 7.30 (m, 2H), 7.20 (m, 2H), 7.12 (d, 1H), 6.75 (m, 2H), 3.26 (t, 2H), 3.12 (t, 2H), 2.70 (s, 3H), 2.68 (s, 3H)

Example 115: Preparation of 5-chloro-4-((4-(difluoromethoxy)-2-(methyl(2-(methylamino)ethyl)amino) phenyl)amino)-2-fluoro-N-(5-fluoropyridin-2-yl) benzenesulfonamide hydrochloride

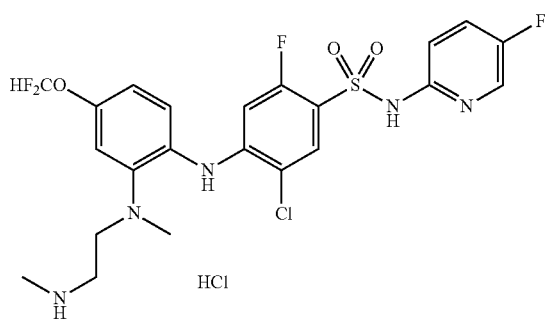

An intermediate was prepared in the same manner as described in Example 103, except that 4-(difluoromethoxy)-2-fluoro-1-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluoropyridin-2-yl)sulfamoyl)-5-fluorophenyl)amino)-5-(difluoromethyl)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.2%).

1H NMR (500 MHz, MeOD): 8.06 (d, 1H), 7.90 (d, 1H), 7.52 (m, 1H), 7.29 (d, 1H), 7.16 (m, 1H), 7.02 (d, 1H), 6.94 (m, 1H), 6.84 (t, 1H), 6.53 (d, 1H), 3.26 (t, 2H), 3.10 (t, 2H), 2.70 (s, 3H), 2.66 (s, 3H)

Example 116: Preparation of 5-chloro-4-((4-(difluoromethoxy)-2-(methyl(2-(methylamino)ethyl)amino)phenyl)amino)-2-fluoro-N-(thiazol-2-yl)benzenesulfonamide hydrochloride

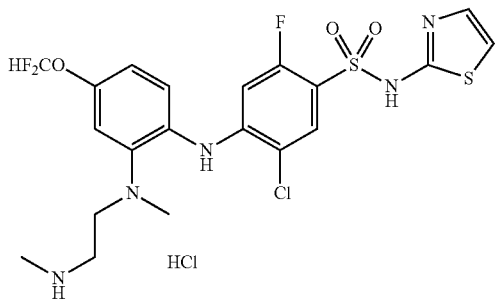

An intermediate was prepared in the same manner as described in Example 103, except that 4-(difluoromethoxy)-2-fluoro-1-nitrobenzene was used instead of 2,4-difluoro-1-nitrobenzene (i) and thiazol-2-amine was used instead of 5-fluoropyridin-2-amine (iv). To the obtained intermediate tert-butyl (2-((2-((2-chloro-4-(N-(2,4-dimethoxybenzyl)-N-(thiazol-2-yl)sulfamoyl)-5-fluorophenyl)amino)-5-(difluoromethoxy)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.7%).

1H NMR (500 MHz, MeOD): 7.85 (d, 1H), 7.29 (d, 1H), 7.11 (d, 1H), 7.03 (d, 1H), 6.94 (d, 1H), 6.85 (t, 1H), 6.75 (d, 1H), 6.58 (d, 1H), 3.23 (t, 2H), 3.12 (t, 2H), 2.72 (s, 3H), 2.67 (s, 3H)

Example 117: Preparation of 5-chloro-4-((4-(difluoromethoxy)-2-(methyl(2-(methylamino)ethyl)amino)phenyl)amino)-2-fluoro-N-(pyridin-2-yl)benzenesulfonamide hydrochloride

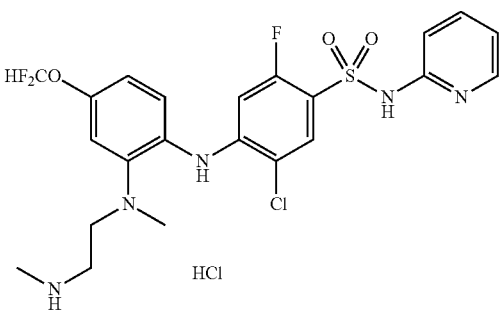

An intermediate was prepared in the same manner as described in Example 103, except that 4-(difluoromethoxy)-2-fluoro-1-nitrobenzene was used instead of 2,4-difluoro-1-nitrobenzene (i) and pyridine-2-amine was used instead of 5-fluoropyridin-2-amine (iv). To the obtained intermediate tert-butyl (2-((2-((2-chloro-4-(N-(2,4-dimethoxybenzyl)-N-(pyridine-2-yl)sulfamoyl)-5-fluorophenyl)amino)-5-(difluoromethoxy)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.3%).

1H NMR (500 MHz, MeOD): 8.04 (d, 1H), 7.95 (d, 1H), 7.90 (t, 1H), 7.30 (m, 2H), 7.06 (m, 2H), 6.93 (d, 1H), 6.84 (t, 1H), 6.56 (d, 1H), 3.26 (t, 2H), 3.11 (t, 2H), 2.70 (s, 3H), 2.67 (s, 3H)

Example 118: Preparation of 5-chloro-2-fluoro-N-(5-fluoropyridin-2-yl)-4-((4-methoxy-2-(methyl(2-(methylamino)ethyl)amino)phenyl)amino)benzenesulfonamide hydrochloride

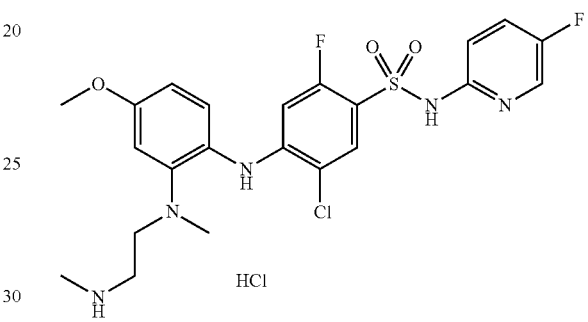

An intermediate was prepared in the same manner as described in Example 103, except that 2-fluoro-4-methoxy-1-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluoropyridin-2-yl)sulfamoyl)-5-fluorophenyl)amino)-5-(methoxyphenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.5%).

1H NMR (500 MHz, MeOD): 8.05 (d, 1H), 7.86 (d, 1H), 7.53-7.50 (m, 1H), 7.18-7.14 (m, 2H), 6.80-6.73 (m, 2H), 6.35 (d, 1H), 3.82 (s, 3H), 3.25-3.23 (m, 2H), 3.09-3.07 (m, 2H), 2.67 (s, 3H), 2.64 (s, 3H)

Example 119: Preparation of 5-chloro-2-fluoro-4-((4-methoxy-2-(methyl(2-(methylamino)ethyl)amino)phenyl)amino)-N-(thiazol-2-yl)benzenesulfonamide hydrochloride

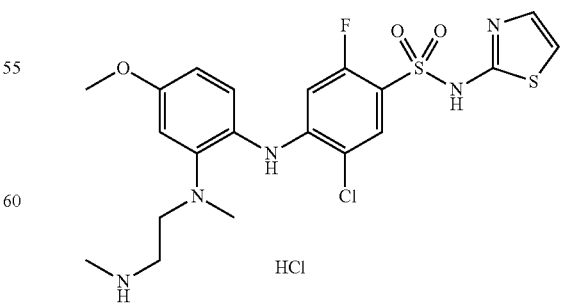

An intermediate was prepared in the same manner as described in Example 103, except that 2-fluoro-4-methoxy-1-nitrobenzene was used instead of 2,4-difluoro-1-nitrobenzene (i) and thiazol-2-amine was used instead of 5-fluoropyridin-2-amine (iv). To the obtained intermediate tert-butyl (2-((2-((2-chloro-4-(N-(2,4-dimethoxybenzyl)-N-(thiazol-2-yl)sulfamoyl)-5-fluorophenyl)amino)-5-methoxyphenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 60.0%).

1H NMR (500 MHz, MeOD): 7.81 (d, 1H), 7.20 (d, 1H), 7.11 (d, 1H), 6.81-6.73 (m, 3H), 6.40 (d, 1H), 3.82 (s, 3H), 3.30-3.28 (m, 2H), 3.25-3.24 (m, 2H), 2.69 (s, 3H), 2.66 (s, 3H)

Example 120: Preparation of 5-chloro-2-fluoro-4-((4-methoxy-2-(methyl(2-(methylamino)ethyl)amino)phenyl)amino)-N-(thiazol-4-yl)benzenesulfonamide hydrochloride

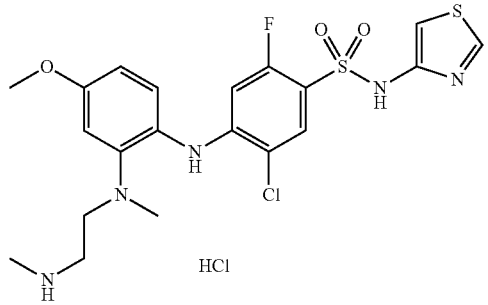 [SMILES: CNCCN(C)c1cc(OC)ccc1Nc1cc(F)c(S(=O)(=O)Nc2cscn2)cc1Cl ; Cl]

An intermediate was prepared in the same manner as described in Example 92, except that 2-fluoro-4-methoxy-1-nitrobenzene was used instead of 2,4-difluoro-1-nitrobenzene (i). To the obtained intermediate tert-butyl (2-((2-((4-(N-(tert-butoxycarbonyl)-N-(thiazol-4-yl)sulfamoyl)-2-chloro-5-fluorophenyl)amino)-5-methoxyphenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 55.5%).

1H NMR (500 MHz, MeOD): 8.73 (d, 1H), 7.76 (d, 1H), 7.18 (d, 1H), 7.02 (d, 1H), 6.82 (d, 1H), 6.75 (d, 1H), 6.36 (d, 1H), 3.85 (s, 3H), 3.26-3.24 (m, 2H), 3.09-3.07 (m, 2H), 2.69 (s, 3H), 2.64 (s, 3H)

Example 121: Preparation of 5-chloro-2-fluoro-4-((2-(methyl(2-(methylamino)ethyl)amino)phenyl)amino)-N-(thiazol-4-yl)benzenesulfonamide hydrochloride

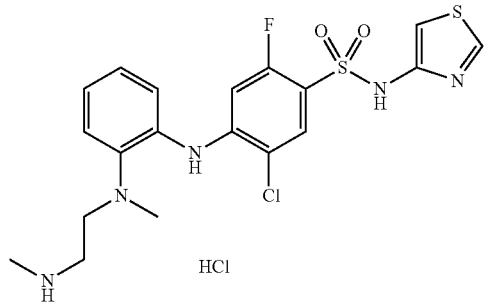 [SMILES: CNCCN(C)c1ccccc1Nc1cc(F)c(S(=O)(=O)Nc2cscn2)cc1Cl ; Cl]

An intermediate was prepared in the same manner as described in Example 92, except that 1-fluoro-2-nitrobenzene was used instead of 2,4-difluoro-1-nitrobenzene (i). To the obtained intermediate tert-butyl (2-((2-((4-(N-(tert-butoxycarbonyl)-N-(thiazol-4-yl)sulfamoyl)-2-chloro-5-fluorophenyl)amino)phenyl(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 57.5%).

1H NMR (500 MHz, MeOD): 8.74 (d, 1H), 7.81 (d, 1H), 7.33-7.18 (m, 4H), 7.04 (d, 1H), 6.70 (d, 1H), 3.26-3.24 (m, 2H), 3.12-3.09 (m, 2H), 2.69 (s, 3H), 2.66 (s, 3H)

Example 122: Preparation of 5-chloro-2-fluoro-N-(5-fluoropyrimidin-2-yl)-4-((4-methoxy-2-(methyl(2-(methylamino)ethyl)amino)phenyl)amino)benzenesulfonamide hydrochloride

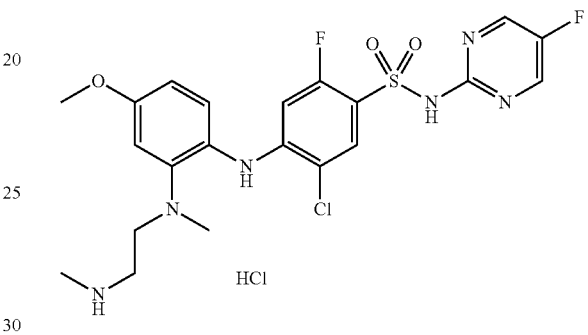

An intermediate was prepared in the same manner as described in Example 96, except that 2-fluoro-4-methoxy-1-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluoropyrimidin-2-yl)sulfamoyl)-5-fluorophenyl)amino)-5-methoxyphenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.5%).

1H NMR (500 MHz, MeOD): 8.42 (s, 2H), 7.96 (d, 1H), 7.18 (d, 1H), 6.82 (d, 1H), 6.76 (d, 1H), 6.36 (d, 1H), 3.81 (s, 3H), 3.27-3.25 (m, 2H), 3.17-3.08 (m, 2H), 2.70 (s, 3H), 2.65 (s, 3H)

Example 123: Preparation of 5-chloro-4-((4-chloro-2-(methyl(2-(methylamino)ethyl)amino)phenyl)amino)-2-fluoro-N-(thiazol-4-yl)benzenesulfonamide hydrochloride

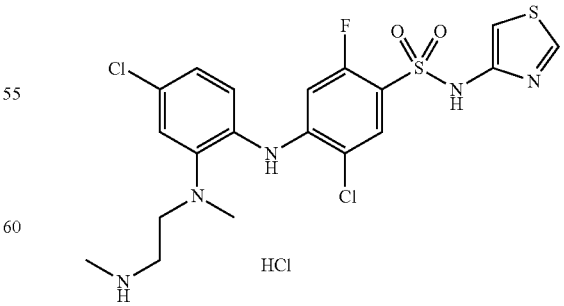

An intermediate was prepared in the same manner as described in Example 92, except that 4-chloro-2-fluoro-1-nitrobenzene was used instead of 2,4-difluoro-1-nitrobenzene (i). To the obtained intermediate tert-butyl (2-((2-((4-

(N-(tert-butoxycarbonyl)-N-(thiazol-4-yl)sulfamoyl)-2-chloro-5-fluorophenyl)amino)-5-chlorophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 55.8%).

1H NMR (500 MHz, MeOD): 8.74 (s, 1H), 7.81 (d, 1H), 7.31-7.14 (m, 3H), 7.04 (d, 1H), 6.64 (d, 1H), 3.26-3.24 (m, 2H), 3.11-3.10 (m, 2H), 2.69 (s, 3H), 2.66 (s, 3H)

Example 124: Preparation of 5-chloro-4-((4-chloro-2-(methyl(2-(methylamino)ethyl)amino)phenyl)amino)-2-fluoro-N-(5-fluoropyrimidin-2-yl)benzenesulfonamide hydrochloride

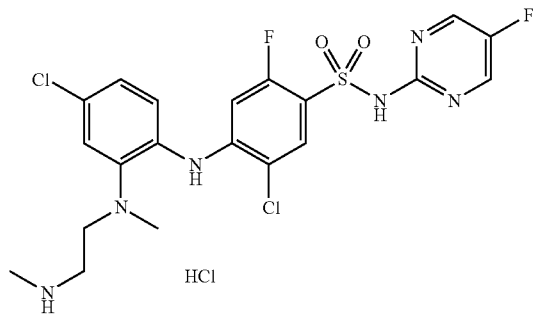 [SMILES: CNCCN(C)c1cc(Cl)ccc1Nc1cc(F)c(S(=O)(=O)Nc2ncc(F)cn2)cc1Cl ; Cl]

An intermediate was prepared in the same manner as described in Example 96, except that 4-chloro-2-fluoro-1-nitrobenzene was used instead of 2,4-difluoro-1-nitrobenzene (i). To the obtained intermediate tert-butyl (2-((5-chloro-2-((2-chloro-4-(N-(2,4-dimethoxybenzyl)-N-(5-fluoropyrimidin-2-yl)sulfamoyl)-5-fluorophenyl)amino)phenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.3%).

1H NMR (500 MHz, MeOD): 8.42 (s, 2H), 8.01 (d, 1H), 7.27 (d, 2H), 7.15-7.13 (m, 1H), 6.64 (d, 1H), 3.27-3.25 (m, 2H), 3.13-3.11 (m, 2H), 2.70 (s, 3H), 2.67 (s, 3H)

Example 125: Preparation of 5-chloro-4-((4-chloro-2-(methyl(2-(methylamino)ethyl)amino)phenyl)amino)-2-fluoro-N-(5-fluoropyridin-2-yl)benzenesulfonamide hydrochloride

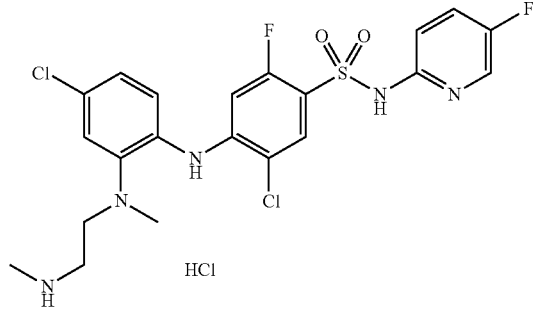 [SMILES: CNCCN(C)c1cc(Cl)ccc1Nc1cc(F)c(S(=O)(=O)Nc2ccc(F)cn2)cc1Cl ; Cl]

An intermediate was prepared in the same manner as described in Example 103, except that 4-chloro-2-fluoro-1-nitrobenzene was used instead of 2,4-difluoro-1-nitrobenzene (i). To the obtained intermediate tert-butyl (2-((5-chloro-2-((2-chloro-4-(N-(2,4-dimethoxybenzyl)-N-(5-fluoropyridin-2-yl)sulfamoyl)-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.3%).

1H NMR (500 MHz, MeOD): 8.06 (d, 1H), 7.91 (d, 1H), 7.54-7.50 (m, 2H), 7.27-7.13 (m, 4H), 6.63 (d, 1H), 3.27-3.25 (m, 2H), 3.11-3.09 (m, 2H), 2.69 (s, 3H), 2.66 (s, 3H)

Example 126: Preparation of 5-chloro-4-((4-chloro-2-(methyl(2-(methylamino)ethyl)amino)phenyl)amino)-2-fluoro-N-(thiazol-2-yl)benzenesulfonamide hydrochloride

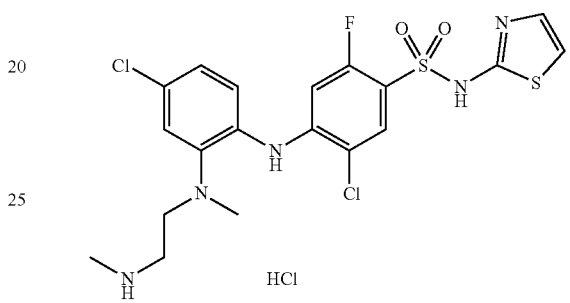

An intermediate was prepared in the same manner as described in Example 103, except that 4-chloro-2-fluoro-1-nitrobenzene was used instead of 2,4-difluoro-1-nitrobenzene (i) and thiazole-2-amine was used instead of 5-fluoropyridin-2-amine (iv). To the obtained intermediate tert-butyl (2-((5-chloro-2-((2-chloro-4-(N-(2,4-dimethoxybenzyl)-N-(thiazol-2-yl)sulfamoyl)-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.8%).

1H NMR (500 MHz, MeOD): 7.87 (d, 1H), 7.27 (d, 2H), 7.15-7.12 (m, 2H), 6.75-6.68 (m, 2H), 3.26-3.25 (m, 2H), 3.13-3.10 (m, 2H), 2.71 (s, 3H), 2.68 (s, 3H)

Example 127: Preparation of 5-chloro-N-(5-chlorothiazol-2-yl)-2-fluoro-4-((4-fluoro-2-(methyl(2-(methylamino)ethyl)amino)phenyl)amino)benzenesulfonamide hydrochloride

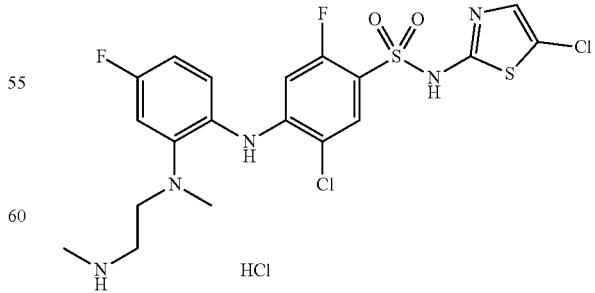

An intermediate was prepared in the same manner as described in Example 103, except that 5-chlorothiazol-2-amine was used instead of 5-fluoropyridin-2-amine (iv). To the obtained intermediate tert-butyl (2-((2-((2-chloro-4-(N-

(5-chlorothiazol-2-yl)-N-(2,4-dimethoxybenzyl)sulfamoyl)-5-fluorophenyl)amino)-5-fluorophenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.2%).

1H NMR (500 MHz, MeOD): 7.82 (d, 1H), 7.29 (d, 1H), 7.27 (s, 1H), 7.05 (d, 1H), 6.90 (t, 1H), 6.48 (d, 1H), 3.27-3.25 (m, 2H), 3.12-3.09 (m, 2H), 2.71 (s, 3H), 2.67 (s, 3H)

Example 128: Preparation of 5-chloro-2-fluoro-4-((4-fluoro-2-(methyl(2-(methylamino)ethyl)amino)phenyl)amino)-N-(5-fluorothiazol-2-yl)benzenesulfonamide hydrochloride

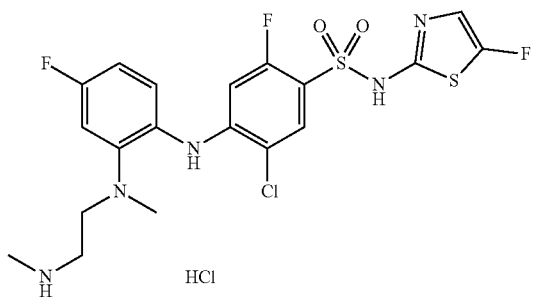 [SMILES: CNCCN(C)c1cc(F)ccc1Nc1cc(F)c(S(=O)(=O)Nc2ncc(F)s2)cc1Cl ; Cl]

An intermediate was prepared in the same manner as described in Example 103, except that 5-fluorothiazol-2-amine was used instead of 5-fluoropyridin-2-amine (iv). To the obtained intermediate tert-butyl (2-((2-((2-chloro-4-(N-(2,4-dimethoxybenzyl)-N-(5-fluorothiazol-2-yl)sulfamoyl)-5-fluorophenyl)amino)-5-fluorophenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.8%).

1H NMR (500 MHz, MeOD): 7.82 (t, 1H), 7.30 (t, 1H), 7.05-6.91 (m, 3H), 6.48 (d, 1H), 3.27-3.25 (m, 2H), 3.12-3.10 (m, 2H), 2.72 (s, 3H), 2.67 (s, 3H)

Example 129: Preparation of 5-chloro-N-(5-chlorothiazol-2-yl)-2-fluoro-4-((2-(methyl(2-(methylamino)ethyl)amino)phenyl)amino)benzenesulfonamide hydrochloride

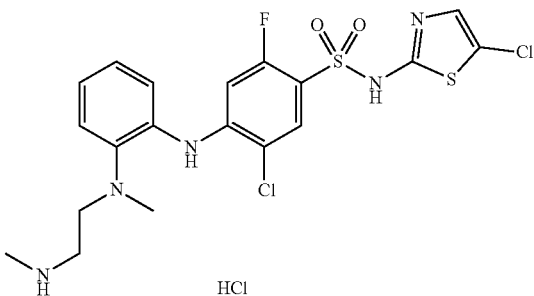 [SMILES: CNCCN(C)c1ccccc1Nc1cc(F)c(S(=O)(=O)Nc2ncc(Cl)s2)cc1Cl ; Cl]

An intermediate was prepared in the same manner as described in Example 103, except that 5-chlorothiazol-2-amine was used instead of 5-fluoropyridin-2-amine (iv) and 1-fluoro-2-nitrobenzene was used instead of 2,4-difluoro-1-nitrobenzene (i). To the obtained intermediate tert-butyl (2-((2-((2-chloro-4-(N-(5-chlorothiazol-2-yl)-N-(2,4-dimethoxybenzyl)sulfamoyl)-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.8%).

1H NMR (500 MHz, MeOD): 7.84 (d, 1H), 7.33 (d, 1H), 7.40 (d, 1H), 7.19 (m, 3H), 6.75 (d, 1H), 3.26 (t, 2H), 3.13 (t, 2H), 2.70 (s, 3H), 2.69 (s, 3H)

Example 130: Preparation of 5-chloro-N-(5-chlorothiazol-2-yl)-2-fluoro-4-((4-methoxy-2-(methyl(2-(methylamino)ethyl)amino)phenyl)amino)benzenesulfonamide hydrochloride

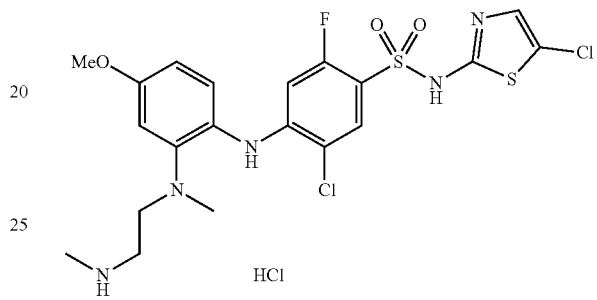

An intermediate was prepared in the same manner as described in Example 103, except that 5-chlorothiazol-2-amine was used instead of 5-fluoropyridin-2-amine (iv) and 2-fluoro-4-methoxy-1-nitrobenzene was used instead of 2,4-difluoro-1-nitrobenzene (i). To the obtained intermediate tert-butyl (2-((2-((2-chloro-4-(N-(5-chlorothiazol-2-yl)-N-(2,4-dimethoxybenzyl)sulfamoyl)-5-fluorophenyl)amino)-5-methoxyphenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 58.7%).

1H NMR (500 MHz, MeOD): 7.79 (d, 1H), 7.20 (d, 1H), 7.19 (s, 1H), 6.80 (d, 1H), 6.75 (dd, 1H), 6.41 (d, 1H), 3.82 (s, 3H), 3.26 (t, 2H), 3.10 (t, 2H), 2.70 (s, 3H), 2.68 (s, 3H)

Example 131: Preparation of 5-chloro-2-fluoro-N-(5-fluorothiazol-2-yl)-4-((2-(methyl(2-(methylamino)ethyl)amino)phenyl)amino)benzenesulfonamide hydrochloride

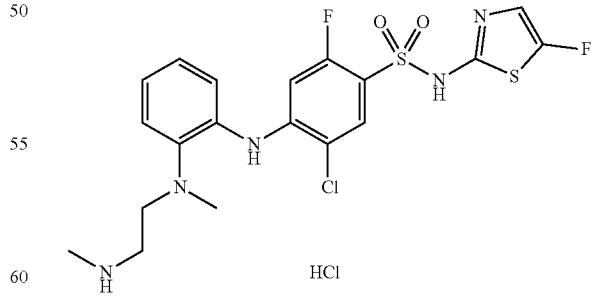

An intermediate was prepared in the same manner as described in Example 103, except that 5-fluorothiazol-2-amine was used instead of 5-fluoropyridin-2-amine (iv) and 1-fluoro-2-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluorothiazol-2-yl)sulfamoyl)-5-fluorophenyl)amino)phenyl)(methyl)amino)ethyl)(methyl) carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 60.5%).

1H NMR (500 MHz, MeOD): 7.84 (d, 1H), 7.31 (m, 2H), 7.22 (m, 2H), 7.00 (s, 1H), 6.76 (d, 1H), 3.27 (t, 2H), 3.13 (t, 2H), 2.70 (s, 3H), 2.69 (s, 3H)

Example 132: Preparation of 5-chloro-2-fluoro-N-(5-fluorothiazol-2-yl)-4-((4-methoxy-2-(methyl(2-(methylamino)ethyl)amino)phenyl)amino)benzenesulfonamide hydrochloride

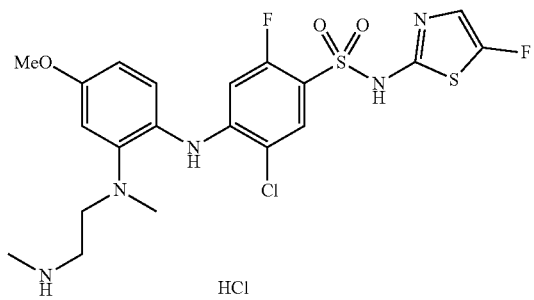 [SMILES: CNCCN(C)c1cc(OC)ccc1Nc1cc(F)c(S(=O)(=O)Nc2ncc(F)s2)cc1Cl ; Cl]

An intermediate was prepared in the same manner as described in Example 103, except that 5-fluorothiazol-2-amine was used instead of 5-fluoropyridin-2-amine (iv) and 2-fluoro-4-methoxy-1-nitrobenzene was used instead of 2,4-difluoro-1-nitrobenzene (i). To the obtained intermediate tert-butyl (2-((2-((2-chloro-4-(N-(2,4-dimethoxybenzyl)-N-(5-fluorothiazol-2-yl)sulfamoyl)-5-fluorophenyl)amino)-5-methoxyphenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.3%).

1H NMR (500 MHz, MeOD): 7.79 (t, 1H), 7.22 (t, 1H), 6.99 (s, 1H), 6.86 (d, 1H), 6.78 (dd, 1H), 6.40 (d, 1H), 3.83 (s, 3H), 3.34 (t, 2H), 3.11 (t, 2H), 2.75 (s, 3H), 2.67 (s, 3H)

Example 133: Preparation of 5-chloro-2-fluoro-4-((4-fluoro-2-(methyl(2-(methylamino)ethyl)amino)phenyl)amino)-N-(5-methylisoxazol-3-yl)benzenesulfonamide hydrochloride

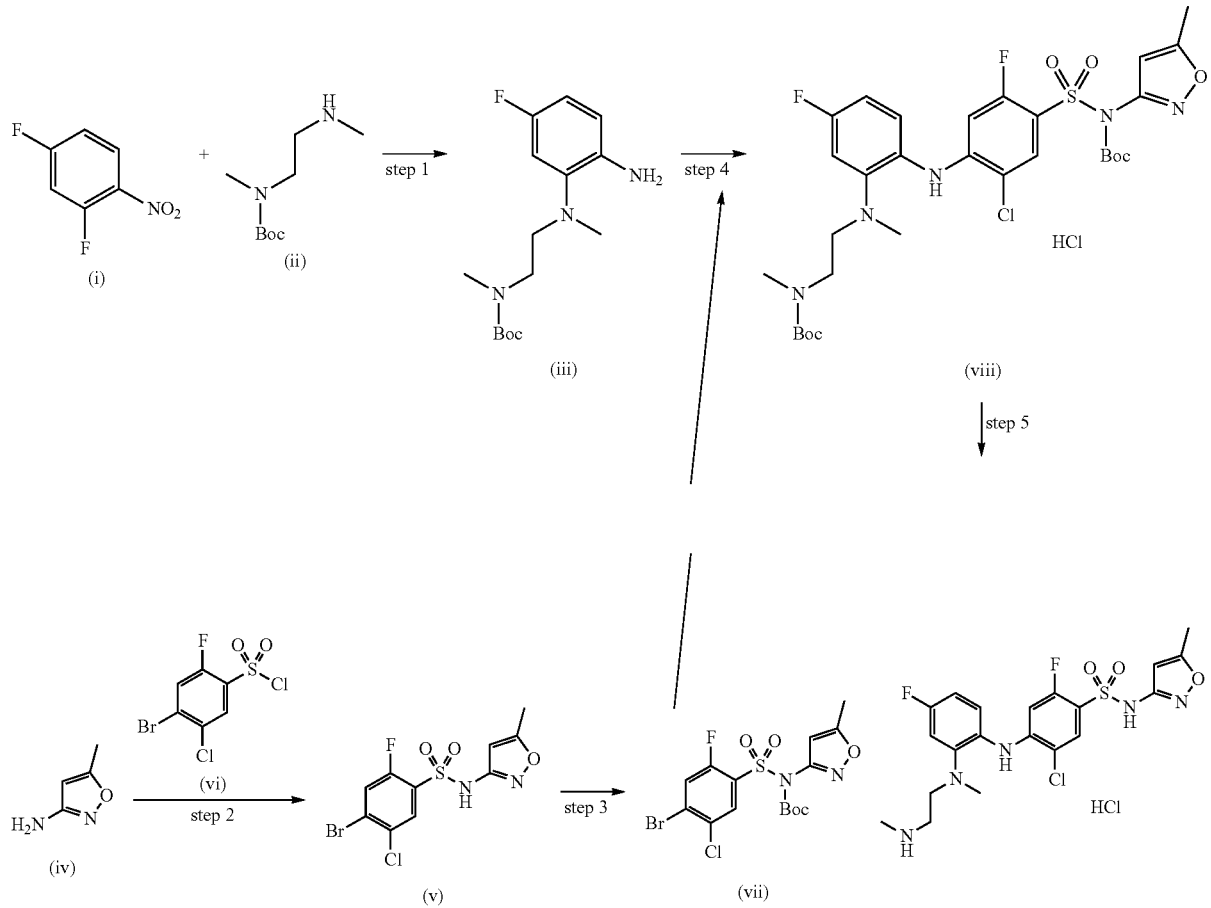

Tert-butyl ((4-bromo-5-chloro-2-fluorophenyl)sulfonyl)(5-methylisoxazol-3-yl)carbamate (vii) was prepared instead of steps 2 and 3 of Example 92. Specifically, 5-methylisoxazol-3-amine (iv, 1.00 g, 10.19 mmol), (4-bromo-5-chloro-2-fluorobenzenesulfonyl chloride (vi, 3.14 g, 1.0 eq.) and pyridine (2.4 mL, 3.0 eq.) were dissolved in DCM (25 mL). After stirring the mixture stirred overnight, the completion of the reaction was confirmed by TLC. H$_2$O (30 mL) was added and extracted twice with dichloromethane (10 mL). MgSO$_4$ was added to the reaction and extracted twice with ethyl acetate. MgSO$_4$, was added to the organic layer, which was stirred, filtered and then dried. The filtrate was concentrated under reduced pressure, and then the resulting residue was separated by column chromatography using a mobile phase of EA/Hex=1/1 to obtain 1.0 g (yield 27%) of the target compound (v).

1H NMR (500 MHz, CDCl$_3$): 8.66 (d, 1H), 7.96 (d, 1H), 7.44 (d, 1H), 5.88 (broad, 1H), 2.33 (s, 3H).

The above-prepared 4-bromo-5-chloro-2-fluoro-N-(5-methylisoxazol-3-yl)benzenesulfonamide (v, 1.00 g, 2.71 mmol), N,N-dimethylaminopyridine (0.06 g, 0.2 eq.) and di-tert-butyl dicarbonate (1.1 mL, 2.0 eq.) were dissolved in tetrahydrofuran (20 mL). After stirring the reaction solution overnight at room temperature, and the completion of the reaction was confirmed by TLC. H$_2$O (30 mL) was added to the reaction product, and the mixture was extracted twice with ethyl acetate. MgSO$_4$ was added to the organic layer, which was stirred, filtrated and then dried. The filtrate was concentrated under reduced pressure, and the obtained residue was separated by column chromatography using a mobile phase of EA/Hex=1/2 to obtain 0.40 g (yield 31%) of the target compound (vii).

1H NMR (500 MHz, MeOD): 8.19 (d, 1H), 7.93 (d, 1H), 6.34 (s, 1H), 2.49 (s, 3H), 1.36 (s, 9H)

The target compounds were prepared in the same manner as described in steps 1, 4 and 5 of Example 1, except that the above-prepared tert-butyl ((4-bromo-5-chloro-2-fluorophenyl)sulfonyl)(5-methylisoxazol-3-yl)carbamate (vii) was used.

1H NMR (500 MHz, MeOD): 7.8 (d, 1H), 7.34-7.31 (m, 2H), 7.25 (t, 1H), 7.21-7.19 (m, 1H), 6.71 (d, 1H), 6.07 (s, 1H), 2.70 (s, 3H), 2.67 (s, 3H), 2.32 (s, 3H)

Example 134: Preparation of 5-chloro-2-fluoro-4-((2-(methyl(2-(methylamino)ethyl)amino)phenyl)amino)-N-(5-methylisoxazol-3-yl)benzenesulfonamide hydrochloride

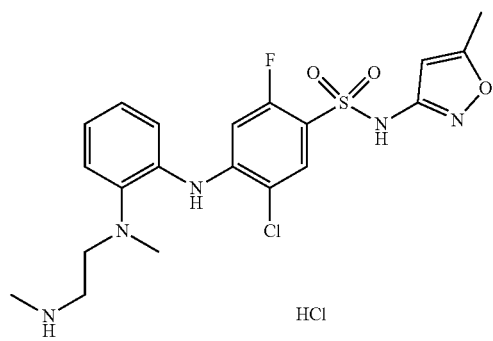 [SMILES: CNCCN(C)c1ccccc1Nc1cc(F)c(S(=O)(=O)Nc2cc(C)on2)cc1Cl ; Cl]

An intermediate was prepared in the same manner as described in Example 133, except that 1-fluoro-2-nitrobenzene was used instead of 2,4-difluoro-1-nitrobenzene (i). To the obtained intermediate tert-butyl (2-((2-((4-(N-(tert-butoxycarbonyl)-N-(5-methylisoxazol-3-yl)sulfamoyl)-2-chloro-5-fluorophenyl)amino)phenyl)(methyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 65.6%).

1H NMR (500 MHz, MeOD): 7.79 (d, 1H), 7.21 (t, 1H), 7.00 (d, 1H), 6.98 (t, 1H), 6.41 (d, 1H), 5.85 (s, 1H), 3.24-3.23 (m, 2H), 3.05-3.03 (m, 2H), 2.69 (s, 3H), 2.58 (s, 3H), 2.22 (s, 3H)

Example 135: Preparation of 5-chloro-2-fluoro-4-((4-fluoro-2-(methyl(2-(methylamino)ethyl)amino)phenyl)amino)-N-(5-methyl-1H-pyrazol-3-yl)benzenesulfonamide hydrochloride

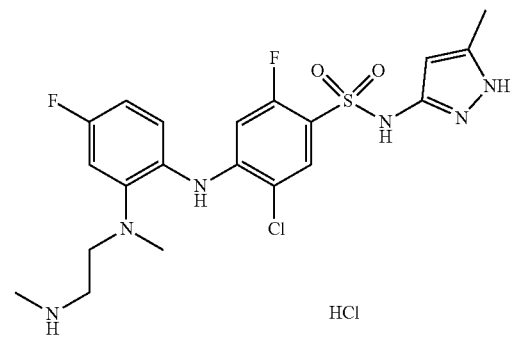 [SMILES: CNCCN(C)c1cc(F)ccc1Nc1cc(F)c(S(=O)(=O)Nc2cc(C)[nH]n2)cc1Cl ; Cl]

An intermediate was prepared in the same manner as described in Example 133, except that tert-butyl 3-amino-5-methyl-1H-pyrazole-1-carboxylate was used instead of 5-methylisoxazol-3-amine (iv). To the obtained intermediate tert-butyl 3-((N-(tert-butoxycarbonyl)-4-(2-(2-((tert-butoxycarbonyl)(methyl)amino)ethyl)(methyl)amino)-4-fluorophenyl)amino)-5-chloro-2-fluorophenyl)sulfonamido)-5-methyl-1H-pyrazole-1-carboxylate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 64.7%).

1H NMR (500 MHz, MeOD): 7.86 (1H), 7.27 (t, 1H), 7.06 (d, 1H), 6.89 (t, 1H), 6.47 (d, 1H), 6.08 (d, 1H), 3.15-3.12 (m, 2H), 2.71 (s, 3H), 2.67 (s, 3H), 2.34 (s, 3H)

Example 136: Preparation of 5-chloro-2-fluoro-4-((2-(methyl(2-(methylamino)ethyl)amino)phenyl)amino)-N-(5-methyl-1H-pyrazol-3-yl)benzenesulfonamide hydrochloride

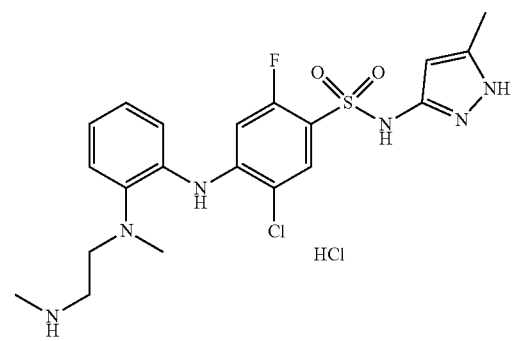 [SMILES: CNCCN(C)c1ccccc1Nc1cc(F)c(S(=O)(=O)Nc2cc(C)[nH]n2)cc1Cl ; Cl]

An intermediate was prepared in the same manner as described in Example 133, except that tert-butyl 3-amino-5-methyl-1H-pyrazole-1-carboxylate was used instead of 5-methylisoxazol-3-amine (iv), and 1-fluoro-2-nitrobenzene was used instead of 2,4-difluoro-1-nitrobenzene (i). To the obtained intermediate tert-butyl 3-((N-(tert-butoxycarbonyl)-4-(2-(2-((tert-butoxycarbonyl)(methyl)amino)ethyl)(methyl)amino)phenyl)amino)-5-chloro-2-fluorophenyl)sulfonamido)-5-methyl-1H-pyrazole-1-carboxylate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 65.7%).

1H NMR (500 MHz, MeOD): 7.88 (d, 1H), 7.35-7.21 (m, 4H), 6.72 (d, 1H), 6.08 (s, 1H), 3.35-3.33 (m, 2H), 3.14-3.11 (m, 2H), 2.72 (s, 3H), 2.68 (s, 3H), 2.34 (s, 3H)

Example 137: Preparation of 5-chloro-4-((2-((2-(dimethylamino)ethyl)(methyl)amino)-4-fluorophenyl)amino)-2-fluoro-N-(5-fluoropyridin-2-yl)benzenesulfonamide hydrochloride An intermediate (viii) was prepared in the same manner as described in Example 103, except that N,N,N'-trimethyl-ethane-1,2-diamine was used instead of tert-butylmethyl(2-(methylamino)ethyl)carbamate (ii). To the obtained intermediate 5-chloro-N-(2,4-dimethoxybenzyl)-4-((2-(dimethylamino)ethyl)(methyl)amino)-4-fluorophenyl)amino)-2-fluoro-N-(5-fluoropyridine-2-yl)benzenesulfonamide (viii, 0.05 g, 0.08 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 48.3%).

1H NMR (500 MHz, MeOD): 8.06 (d, 1H), 7.88 (d, 1H), 7.53 (m, 1H), 7.25 (dd, 1H), 7.16 (dd, 1H), 7.04 (m, 1H), 6.88 (m, 1H), 6.35 (d, 1H), 3.33 (t, 2H), 3.20 (t, 2H), 2.92 (s, 6H), 2.71 (s, 3H)

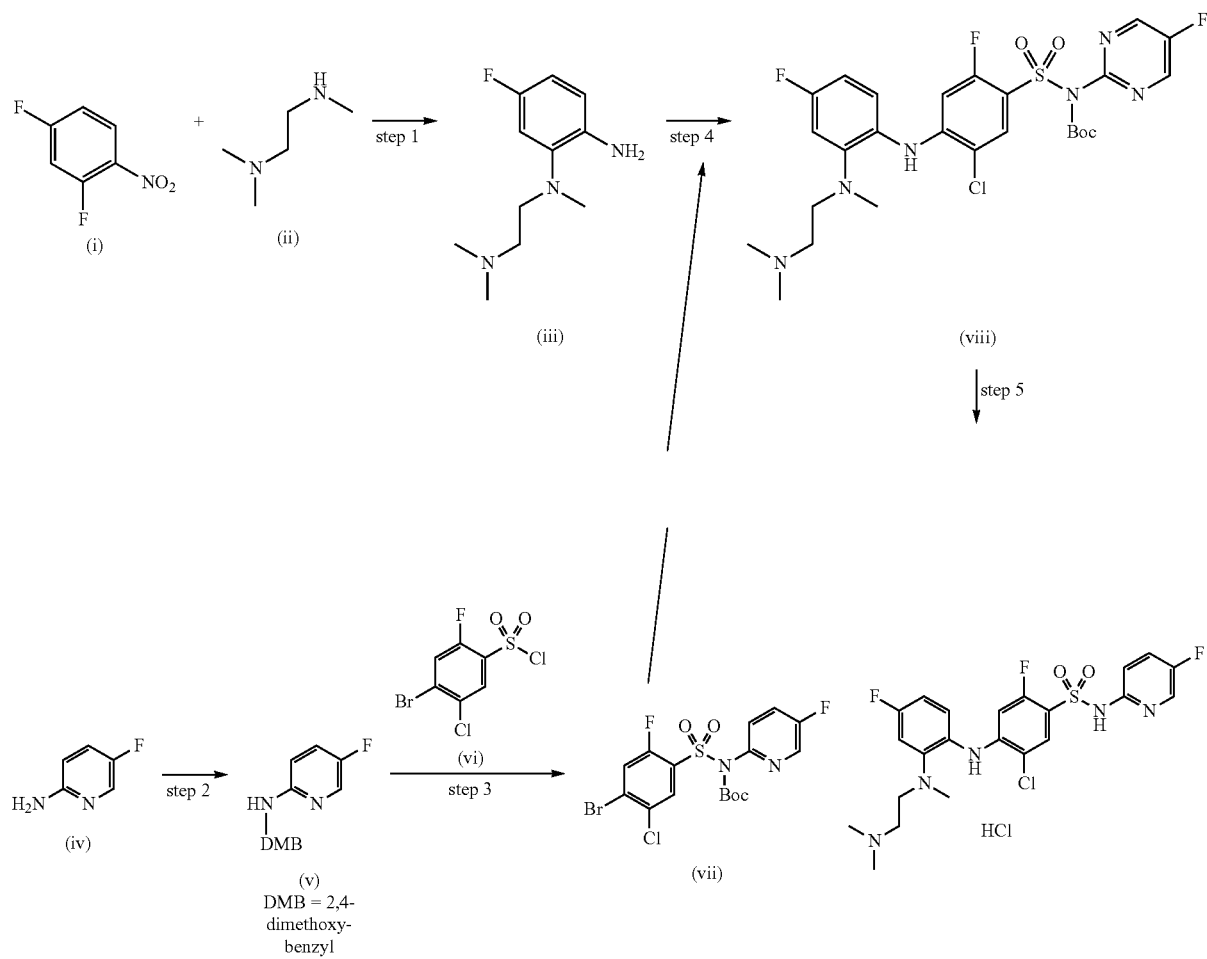

Example 138: Preparation of 5-chloro-4-((2-((2-(dimethylamino)ethyl)(methyl)amino)-4-fluorophenyl)amino)-2-fluoro-N-(thiazol-2-yl)benzenesulfonamide hydrochloride

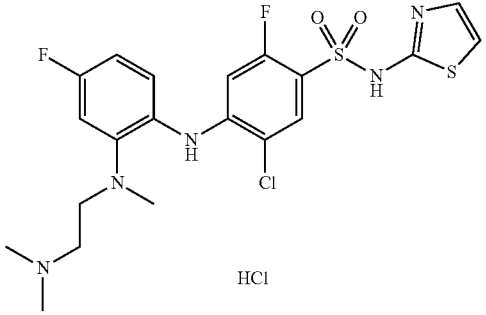 [SMILES: CN(C)CCN(C)c1cc(F)ccc1Nc1cc(F)c(S(=O)(=O)Nc2nccs2)cc1Cl ; Cl]

An intermediate was prepared in the same manner as described in Example 137, except that thiazol-2-amine was used instead of 5-fluoropyridine-2-amine (iv). To the obtained intermediate 5-chloro-N-(2,4-dimethoxybenzyl)-4-((2-((dimethylamino)ethyl)(methyl)amino)-4-fluorophenyl)amino)-2-fluoro-N-(thiazol-2-yl)benzene sulfonamide (0.05 g, 0.08 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 48.4%).

1H NMR (500 MHz, MeOD): 7.83 (d, 1H), 7.27 (m, 1H), 7.12 (t, 1H), 7.04 (m, 1H), 6.90 (t, 1H), 6.75 (d, 1H), 6.40 (d, 1H), 3.34 (t, 2H), 3.22 (t, 2H), 2.83 (s, 6H), 2.73 (s, 3H)

Example 139: Preparation of 5-chloro-N-(5-chlorothiazol-2-yl)-4-((2-((2-(dimethylamino)ethyl)(methyl)amino)-4-fluorophenyl)amino)-2-fluorobenzenesulfonamide hydrochloride

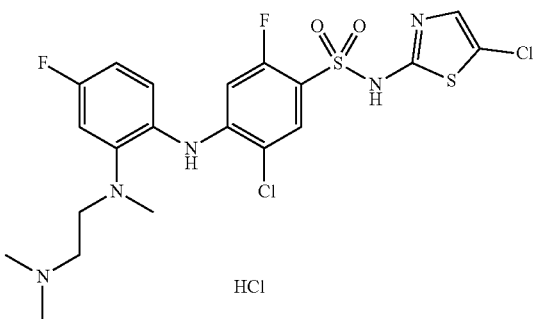 [SMILES: CN(C)CCN(C)c1cc(F)ccc1Nc1cc(F)c(S(=O)(=O)Nc2ncc(Cl)s2)cc1Cl ; Cl]

An intermediate was prepared in the same manner as described in Example 137, except that 5-chlorothiazol-2-amine was used instead of 5-fluoropyridine-2-amine (iv). To the obtained intermediate 5-chloro-N-(5-chlorothiazol-2-yl)-N-(2,4-dimethoxybenzyl)-4-((2-((2-(dimethylamino)ethyl)(methyl)amino)-4-fluorophenyl)amino)-2-fluorobenzene sulfonamide (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 47.9%).

1H NMR (500 MHz, MeOD): 7.82 (d, 1H), 7.28 (t, 1H), 7.19 (d, 1H), 7.05 (d, 1H), 6.89 (t, 1H), 6.41 (d, 1H), 3.30 (t, 2H), 3.23 (t, 2H), 2.84 (s, 6H), 2.74 (s, 3H)

Example 140: Preparation of 5-chloro-N-(5-chlorothiazol-2-yl)-4-((2-((2-(dimethylamino)ethyl)(methyl)amino)phenyl)amino)-2-fluorobenzenesulfonamide hydrochloride

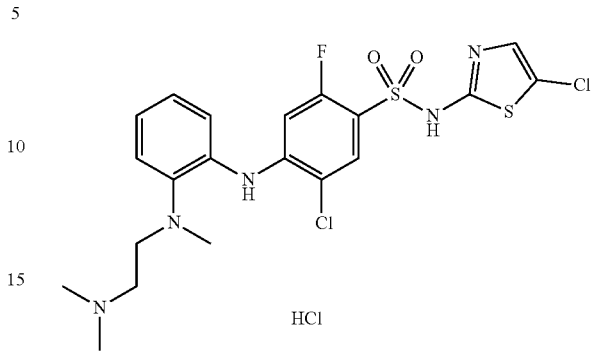

An intermediate was prepared in the same manner as described in Example 137, except that 5-chlorothiazol-2-amine was used instead of 5-fluoropyridine-2-amine (iv) and 2-fluoro-1-nitrobenzene was used instead of 2,4-difluoro-1-nitrobenzene (i). To the obtained intermediate 5-chloro-N-(5-chlorothiazol-2-yl)-N-(2,4-dimethoxybenzyl)-4-((2-((2-(dimethylamino)ethyl)(methyl)amino)phenyl)amino)-2-fluorobenzene sulfonamide (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 48.2%).

1H NMR (500 MHz, MeOD): 7.84 (d, 1H), 7.31 (t, 2H), 7.25 (t, 1H), 7.20 (t, 2H), 6.40 (d, 1H), 3.36 (t, 2H), 3.24 (t, 2H), 2.86 (s, 6H), 2.72 (s, 3H)

Example 141: Preparation of 5-chloro-2-fluoro-4-((4-fluoro-2-(methyl(2-(methylamino)ethyl)amino)phenyl)amino)-N-(5-methylthiazol-2-yl)benzenesulfonamide hydrochloride

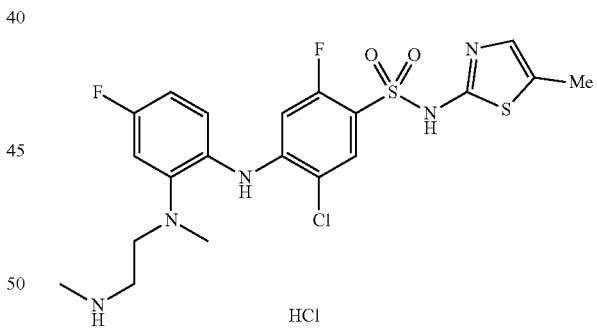

An intermediate was prepared in the same manner as described in Example 103, except that 5-methylthiazol-2-amine was used instead of 5-fluoropyridine-2-amine (iv). To the obtained intermediate tert-butyl 2-((2-((2-chloro-4-(N-(2,4-dimethoxybenzyl)-N-(5-methylthiazol-2-yl)sulfamoyl)-5-fluorophenyl)amino)-5-fluorophenyl)(methyl)amino)ethyl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 53.0%).

1H NMR (500 MHz, MeOD): 7.83 (d, 1H), 7.29 (dd, 1H), 7.05 (dd, 1H), 6.89 (t, 1H), 6.82 (s, 1H), 6.47 (d, 1H), 3.27 (t, 2H), 2.11 (t, 2H), 2.72 (s, 3H), 2.67 (s, 3H), 2.24 (s, 3H)

Example 142: Preparation of 5-chloro-2-fluoro-4-((4-fluoro-2-(methyl(2-(methylamino)ethyl)amino)phenyl)amino)-N-(oxazol-2-yl)benzenesulfonamide hydrochloride

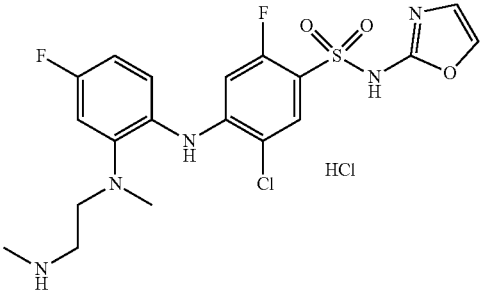 [SMILES: CNCCN(C)c1cc(F)ccc1Nc1cc(F)c(S(=O)(=O)Nc2ncco2)cc1Cl ; Cl]

An intermediate was prepared in the same manner as described in Example 133, except that oxazole-2-amine was used instead of 5-methylisoxazole-3-amine (iv). To the obtained intermediate tert-butyl (2-((2-((4-(N-(tert-butoxycarbonyl)-N-(oxazol-2-yl)sulfamoyl)-2-chloro-5-fluorophenyl)amino)-5-fluorophenyl)(methyl)amino)ethyl)(methyl)carbamate (0.03 g, 0.05 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.01 g, 47.5%).

1H NMR (500 MHz, MeOD): 1H NMR (500 MHz, MeOD): 7.87 (d, 1H), 7.25-7.22 (m, 2H), 7.01 (d, 1H), 6.85-6.84 (m, 1H), 6.42 (d, 1H), 5.48 (s, 1H), 3.25-3.24 (m, 2H), 3.09-3.07 (m, 2H), 2.71 (s, 3H), 2.61 (s, 3H)

Example 143: Preparation of N-(5-(tert-butyl)isoxazol-3-yl)-5-chloro-2-fluoro-4-((4-fluoro-2-(methyl(2-(methylamino)ethyl)amino)phenyl)amino)benzenesulfonamide hydrochloride

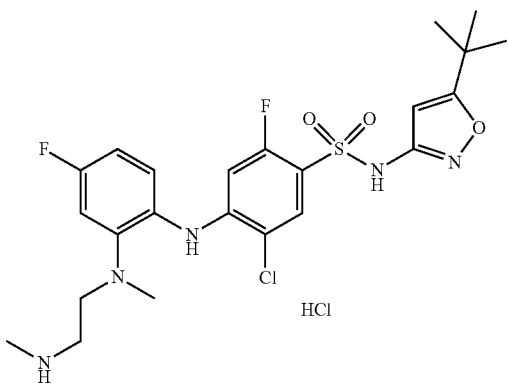 [SMILES: CNCCN(C)c1cc(F)ccc1Nc1cc(F)c(S(=O)(=O)Nc2cc(C(C)(C)C)on2)cc1Cl ; Cl]

An intermediate was prepared in the same manner as described in Example 133, except that 5-(tert-butyl) isoxazole-3-amine was used instead of 5-methylisoxazole-3-amine (iv). To the obtained intermediate tert-butyl (2-((2-((4-(N-(tert-butoxycarbonyl)-N-(5-tert-butyl)isoxazol-3-yl)sulfamoyl)-2-chloro-5-fluorophenyl)amino)-5-fluorophenyl)(methyl)amino)ethyl)(methyl)carbamate (0.03 g, 0.04 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.01 g, 46.4%).

1H NMR (500 MHz, MeOD): 7.78 (d, 1H), 7.19-7.16 (m, 1H), 6.97 (d, 1H), 6.82-6.79 (m, 1H), 6.42 (d, 1H), 5.87 (s, 1H), 3.30-3.29 (m, 2H), 2.67 (s, 3H), 2.64 (s, 3H), 1.23 (s, 9H)

Example 144: Preparation of N-(5-(tert-butyl)isoxazol-3-yl)-5-chloro-2-fluoro-4-((2-(methyl(2-(methylamino)ethyl)amino)phenyl)amino)benzenesulfonamide hydrochloride

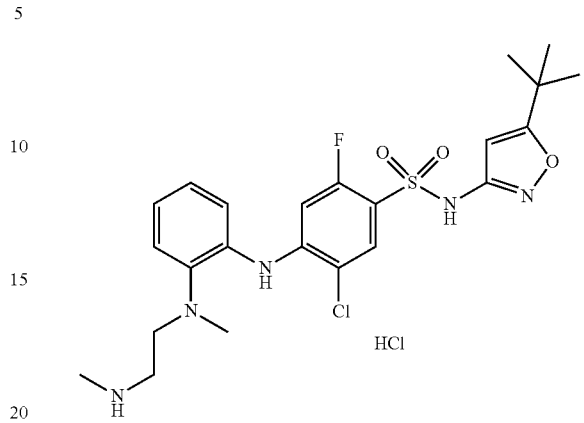

An intermediate was prepared in the same manner as described in Example 133, except that 5-(tert-butyl)isoxazole-3-amine was used instead of 5-methylisoxazole-3-amine (iv) and 1-fluoro-2-nitrobenzene was used instead of 2,4-difluoro-1-nitrobenzene (i). To the obtained intermediate tert-butyl (2-((2-((4-(N-(tert-butoxycarbonyl)-N-(5-tert-butyl)isoxazol-3-yl)sulfamoyl)-2-chloro-5-fluorophenyl)amino)phenyl)(methyl)amino)ethyl)(methyl)carbamate (0.03 g, 0.04 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.01 g, 46.0%).

1H NMR (500 MHz, MeOD): 7.83 (d, 1H), 7.23 (d, 2H), 7.14-7.10 (m, 2H), 6.70 (d, 1H), 5.89 (s, 1H), 3.30-3.27 (m, 2H), 3.13-3.11 (m, 2H), 2.66 (s, 6H), 1.23 (s, 9H)

Example 145: Preparation of 5-chloro-2-fluoro-4-((4-fluoro-2-(3-(methylamino)pyrrolidin-1-yl)phenyl)amino)-N-(1,2,4-thiadiazol-5-yl)benzenesulfonamide hydrochloride

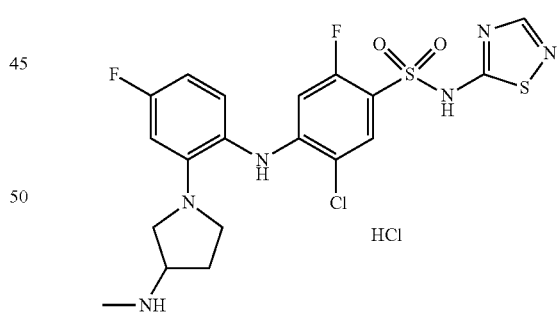

An intermediate was prepared in the same manner as described in Example 133, except that 1,2,4-thiadiazol-5-amine was used instead of 5-methylisoxazole-3-amine (iv) and tert-butyl methyl(pyrrolidin-3-yl)carbamate was used instead of tert-butyl methyl(2-(methylamino)ethyl)carbamate (ii). To the obtained intermediate tert-butyl (1-(2-((4-(N-(tert-butoxycarbonyl)-N-(1,2,4-thiadiazol-5-yl)sulfamoyl)-2-chloro-5-fluorophenyl)amino)-5-fluorophenyl)pyrrolidin-3-yl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.0%).

1H NMR (500 MHz, MeOD): 8.39 (s, 1H), 7.80 (d, 1H), 7.14 (t, 1H), 6.73 (d, 1H), 6.68 (t, 1H), 6.08 (d, 1H), 3.78 (t, 1H), 3.58 (dd, 1H), 3.48 (m, 1H), 3.40 (dd, 1H), 2.67 (s, 3H), 2.34 (m, 1H), 1.99 (m, 1H)

Example 146: Preparation of 5-chloro-2-fluoro-4-((4-fluoro-2-(3-(methylamino)pyrrolidin-1-yl)phenyl)amino)-N-(1-methyl-1H-pyrazol-3-yl)benzenesulfonamide hydrochloride

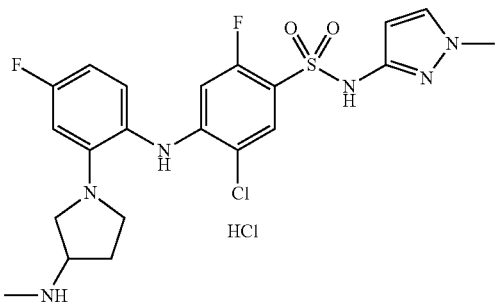

An intermediate was prepared in the same manner as described in Example 133, except that 1-methyl-1H-pyrazol-3-amine was used instead of 5-methylisoxazol-3-amine (iv) and tert-butyl methyl(pyrrolidin-3-yl)carbamate was used instead of tert-butyl methyl(2-(methylamino)ethyl)carbamate (ii). To the obtained intermediate tert-butyl (1-(2-((4-(N-(tert-butoxycarbonyl)-N-(1-methyl-1H-pyrazol-3-yl)sulfamoyl)-2-chloro-5-fluorophenyl)amino)-5-fluorophenyl)pyrrolidin-3-yl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.1%).

1H NMR (500 MHz, MeOD): 7.68 (d, 1H), 7.38 (s, 1H), 7.13 (t, 1H), 6.75 (dd, 1H), 6.86 (t, 1H), 6.06 (d, 1H), 6.00 (s, 1H), 3.78 (t, 1H), 3.70 (s, 3H), 3.56 (dd, 1H), 3.48 (m, 1H), 3.41 (dd, 1H), 3.39 (s. 3H), 2.36 (m, 1H), 1.98 (m, 1H)

Example 147: Preparation of 5-chloro-2-fluoro-4-((4-fluoro-2-(3-(methylamino)pyrrolidin-1-yl)phenyl)amino)-N-(pyrimidin-4-yl)benzenesulfonamide hydrochloride

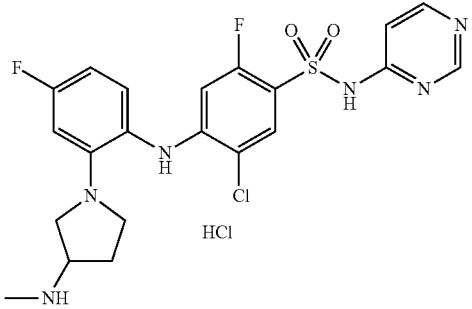 [SMILES: CNC1CCN(c2cc(F)ccc2Nc2cc(F)c(S(=O)(=O)Nc3ccncn3)cc2Cl)C1 ; Cl]

An intermediate was prepared in the same manner as described in Example 133, except that pyrimidin-4-amine was used instead of 5-methylisoxazol-3-amine (iv) and tert-butyl methyl(pyrrolidin-3-yl)carbamate was used instead of tert-butyl methyl(2-(methylamino)ethyl)carbamate (ii). To the obtained intermediate tert-butyl ((4-((2-(3-((tert-butoxycarbonyl)(methyl)amino)pyrrolidin-1-yl)-4-fluorophenyl)amino)-5-chloro-2-fluorophenyl)sulfonyl)(pyrimidin-4-yl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.2%).

1H NMR (500 MHz, MeOD): 8.45 (s, 1H), 8.44 (s, 1H), 7.95 (d, 1H), 7.12 (d, 1H), 7.00 (t, 1H), 6.72 (dd, 1H), 6.66 (td, 1H), 6.04 (d, 1H), 3.78 (t, 1H), 3.56 (dd, 1H), 3.47 (m, 1H), 3.40 (dd, 1H), 2.65 (s, 3H), 2.31 (m, 1H), 1.98 (m, 1H)

Example 148: Preparation of 5-chloro-2-fluoro-4-((4-fluoro-2-(3-(methylamino)pyrrolidin-1-yl)phenyl)amino)-N-(5-fluoropyrimidin-2-yl)benzenesulfonamide hydrochloride

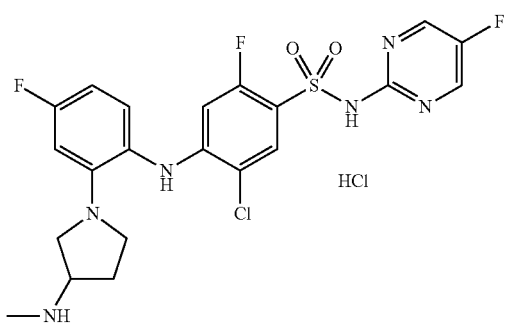 [SMILES: CNC1CCN(c2cc(F)ccc2Nc2cc(F)c(S(=O)(=O)Nc3ncc(F)cn3)cc2Cl)C1 ; Cl]

An intermediate was prepared in the same manner as described in Example 96, except that tert-butyl methyl(pyrrolidin-3-yl)carbamate was used instead of tert-butyl methyl(2-(methylamino)ethyl)carbamate (ii). To the obtained intermediate tert-butyl (1-(2-((2-chloro-4-(N-(2,4-dimethoxybenzyl)-N-(5-fluoropyrimidin-2-yl)sulfamoyl)-5-fluorophenyl)amino)-5-fluorophenyl)pyrrolidin-3-yl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 59.8%).

1H NMR (500 MHz, MeOD): 8.46 (s, 2H), 7.94 (d, 1H), 7.11 (td, 1H), 6.72 (d, 1H), 6.66 (td, 1H), 6.04 (d, 1H), 3.77 (t, 1H), 3.57 (dd, 1H), 3.48 (m, 1H), 3.41 (dd, 1H), 2.66 (s, 3H), 2.33 (m, 1H), 1.99 (m, 1H)

Example 149: Preparation of 5-chloro-2-fluoro-4-((4-fluoro-2-(3-(methylamino)pyrrolidin-1-yl)phenyl)amino)-N-(pyrazin-2-yl)benzenesulfonamide hydrochloride

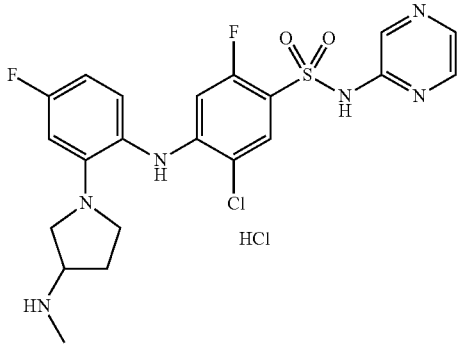 [SMILES: CNC1CCN(c2cc(F)ccc2Nc2cc(F)c(S(=O)(=O)Nc3cnccn3)cc2Cl)C1 ; Cl]

An intermediate was prepared in the same manner as described in Example 96, except that 2-chloropyrazine was used instead of 2-chloro-5-fluoropyrimidine (iv) and tert-butyl methyl(pyrrolidin-3-yl)carbamate was used instead of tert-butyl methyl(2-(methylamino)ethyl)carbamate (ii). To the obtained intermediate tert-butyl (1-(2-((2-chloro-4-(N-(2,4-dimethoxyphenyl)-N-(pyrazin-2-yl)sulfamoyl)-5-fluorophenyl)amino)-5-fluorophenyl)pyrrolidin-3-yl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 60.9%).

1H NMR (500 MHz, MeOD): 8.29 (s, 1H), 8.15 (s, 1H), 8.09 (s, 1H), 7.88 (d, 1H), 7.09 (dd, 1H), 6.70 (dd, 1H), 6.64 (t, 1H), 6.05 (d, 1H), 5.45 (d, 1H), 3.76 (m, 1H), 3.54 (dd, 1H), 3.44 (m, 2H), 2.67 (s, 3H), 2.29 (m, 1H), 1.90 (m, 1H)

Example 150: Preparation of 5-chloro-2-fluoro-4-((4-fluoro-2-(3-(methylamino)pyrrolidin-1-yl)phenyl)amino)-N-(5-methylisoxazol-3-yl)benzenesulfonamide hydrochloride

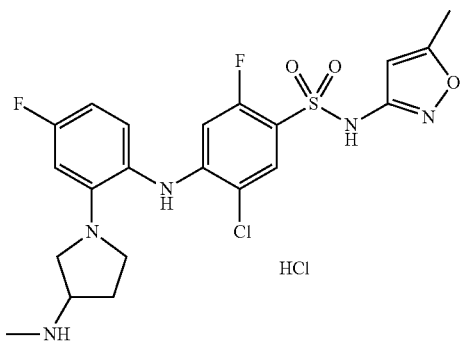 [SMILES: CNC1CCN(c2cc(F)ccc2Nc2cc(F)c(S(=O)(=O)Nc3cc(C)on3)cc2Cl)C1 ; Cl]

An intermediate was prepared in the same manner as described in Example 133, except that tert-butyl methyl(pyrrolidin-3-yl)carbamate was used instead of tert-butyl methyl(2-(methylamino)ethyl)carbamate (ii). To the obtained intermediate tert-butyl (1-(2-((4-(N-(tert-butoxycarbonyl)-N-(5-methylisoxazol-3-yl)sulfamoyl)-2-chloro-5-fluorophenyl)amino)-5-fluorophenyl)pyrrolidin-3-yl)(methyl)carbamate (0.05 g, 0.06 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.1%).

1H NMR (500 MHz, MeOD): 7.80 (d, 1H), 7.14 (dd, 1H), 6.73 (d, 1H), 6.69 (dd, 1H), 6.09 (d, 1H), 6.07 (s, 1H), 3.76 (t, 1H), 3.58 (m, 2H), 3.43 (m, 2H), 2.66 (s, 3H), 2.32 (s, 3H), 2.05 (m, 2H)

Example 151: Preparation of 5-chloro-2-fluoro-4-((4-fluoro-2-(3-(methylamino)pyrrolidin-1-yl)phenyl)amino)-N-(pyrimidin-5-yl)benzenesulfonamide hydrochloride

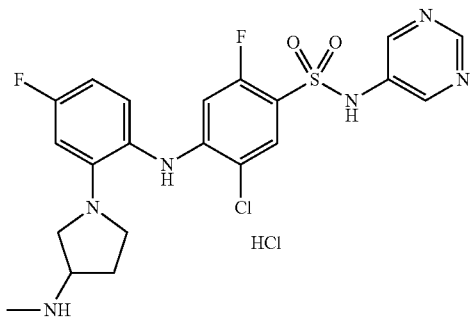 [SMILES: CNC1CCN(c2cc(F)ccc2Nc2cc(F)c(S(=O)(=O)Nc3cncnc3)cc2Cl)C1 ; Cl]

An intermediate was prepared in the same manner as described in Example 133, except that pyrimidin-5-amine was used instead of 5-methylisoxazol-3-amine (iv) and tert-butyl methyl(pyrrolidin-3-yl)carbamate was used instead of tert-butyl methyl(pyrrolidin-3-yl)carbamate (ii). To the obtained intermediate tert-butyl (1-(2-((4-(N-(tert-butoxycarbonyl)(pyrimidin-5-yl)sulfamoyl)-2-chloro-5-fluorophenyl)amino)pyrrolidin-3-yl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.2%).

1H NMR (500 MHz, MeOD): 8.87 (s, 1H), 8.59 (d, 2H), 7.79 (d, 1h), 7.12 (td, 1H), 6.73 (d, 1H), 6.67 (td, 1H), 6.07 (d, 1H), 3.76 (t, 1H), 3.50 (m, 2H), 3.54 (m, 2H), 2.67 (s, 3H), 2.32 (m, 1H), 1.98 (m, 1H)

Example 152: Preparation of 5-chloro-2-fluoro-4-((4-fluoro-2-((2-(methylamino)ethyl)amino)phenyl)amino)-N-(thiazol-4-yl)benzenesulfonamide hydrochloride

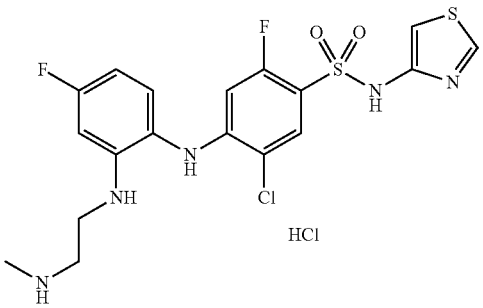 [SMILES: CNCCNc1cc(F)ccc1Nc1cc(F)c(S(=O)(=O)Nc2cscn2)cc1Cl ; Cl]

An intermediate was prepared in the same manner as described in Example 92, except that tert-butyl (2-aminoethyl)(methyl)carbamate was used instead of tert-butyl methyl(2-(methylamino)ethyl)carbamate (ii). To the obtained intermediate tert-butyl (2-((2-((4-(N-(tert-butoxycarbonyl)-N-(thiazol-4-yl)sulfamoyl)-2-chloro-5-fluorophenyl)amino)-5-fluorophenyl)amino)ethyl)(methyl)carbamate (0.05 g, 0.07 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 56.9%).

1H NMR (500 MHz, MeOD): 8.72 (s, 1H), 7.75 (d, 1H), 7.07 (t, 1H), 7.00 (s, 1H), 6.63 (d, 1H), 6.49 (t, 1H), 6.05 (d, 1H), 3.46 (t, 2H), 3.17 (t, 2H), 2.70 (s, 3H)

Example 153: Preparation of 5-chloro-4-((2-((2-(dimethylamino)ethyl)amino)-4-fluorophenyl)amino)-2-fluoro-N-(thiazol-4-yl)benzenesulfonamide hydrochloride

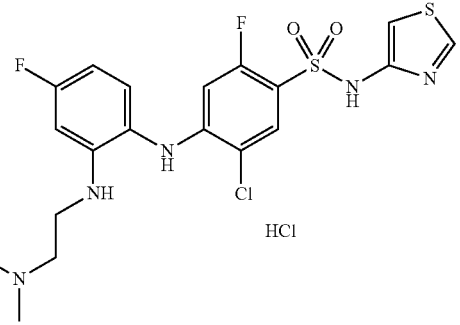

An intermediate was prepared in the same manner as described in Example 92, except that N,N-dimethylethane-1,2-diamine(3-(methylamino)propyl)carbamate was used instead of tert-butyl methyl(2-(methylamino)ethyl)carbamate (ii). To the obtained intermediate tert-butyl (2-((4-(N-(tert-butoxycarbonyl)-N-(thiazol-4-yl)sulfamoyl)-2-chloro-5-fluorophenyl)amino)-5-fluorophenyl)(2-(dimethylamino)ethyl)carbamate (0.02 g, 0.0003 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.01 g, 70.5%).

1H NMR (500 MHz, MeOD): 8.73 (s, 1H), 7.75 (d, 1H), 7.08 (t, 1H), 7.01 (s, 1H), 6.66 (d, 1H), 6.50 (t, 1H), 6.04 (d, 1H), 3.53 (t, 2H), 3.30 (t, 2H), 2.90 (s, 6H)

Example 154: Preparation of 5-chloro-2-fluoro-4-((4-fluoro-2-(methyl(3-(methylamino)propyl)amino)phenyl)amino)-N-(thiazol-4-yl)benzenesulfonamide hydrochloride

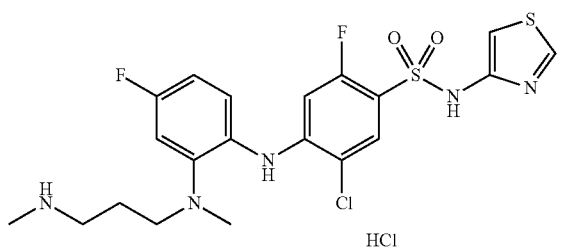 [SMILES: CNCCCN(C)c1cc(F)ccc1Nc1cc(F)c(S(=O)(=O)Nc2cscn2)cc1Cl ; Cl]

An intermediate was prepared in the same manner as described in Example 92, except that tert-butyl methyl(3-(methylamino)propyl)carbamate was used instead of tert-butyl methyl(2-(methylamino)ethyl)carbamate (ii). To the obtained intermediate tert-butyl (3-((2-((4-(N-(tert-butoxycarbonyl)-N-(thiazol-4-yl)sulfamoyl)-2-chloro-5-fluorophenyl)amino)-5-fluorophenyl)(methyl)amino)propyl)(methyl)carbamate (0.05 g, 0.7 mmol) was added 1 M HCl in ethyl acetate (5 mL). After stirring the mixture stirred overnight while heating to 50 to 60° C., the completion of the reaction was confirmed by TLC. The reaction solution was filtered to obtain the target compound (0.02 g, 55.9%).

1H NMR (500 MHz, MeOD): 8.74 (s, 1H), 7.78 (d, 1h), 7.25 (m, 1H), 7.03 (m, 2H), 6.88 (m, 1H), 6.29 (d, 1H), 3.06 (d, 2H), 2.80 (d, 2H), 2.70 (s, 3H), 2.60 (s, 3H), 1.81 (d, 2H)

Experimental Example

In order to measure the activities of the inventive compounds as antagonists, an experiment of blocking effect against sodium ion channel 1.7 (Nav1.7) and sodium ion channel 1.5 (Nav1.5) was carried out as follows.

1) Cell Culture

The hNav 1.7 HEK 293 cell line was a cell line in which a human sodium ion channel 1.7 gene (type IX voltage-gated sodium channel alpha subunit) was stably expressed in human embryonic kidney (HEK) 293 cells, and was purchased from Millipore. The culture medium used was prepared by adding 1% 100×NEAA and 10% heat-inactivated FBS to DMEM F-12, and then adding 1% P/S as an antibiotic thereto. G-418 as a restriction enzyme was added during subculture. The hNav1.7 HEK293 cells were cultured at a confluence of about 80% in a 5% $CO_2$ incubator at 37° C. in a T75 flask for 2 or 3 days, and detached from the flask by treatment with 0.05% trypsin solution. Then, the cells were collected by centrifugation and used in the experiment.

The hNav 1.5 HEK 293 cell line was a cell line in which a human sodium ion channel 1.5 gene (Homo sapiens sodium channel, voltage-gated, type V, alpha subunit (SCN 5 A)) was stably expressed in human embryonic kidney (HEK) 293 cells, and was purchased from Creacell. The culture medium used was prepared by mixing 2% 100× L-glutamine and 10% heat-inactivated FBS to DMEM, and then adding 1% P/S as an antibiotic thereto. G-418 as a restriction enzyme was added during subculture, and the hNav1.5 HEK293 cells were cultured at a confluence of about 80% in a 5% CO2 incubator at 37° C. in a T75 flask for 2 or 3 days, and detached from the flask by treatment with 0.05% trypsin solution. Then, the cells were collected by centrifugation and used in the experiment.

2) Preparation of Compound Samples

The compounds prepared in the Examples of the present invention were dissolved in dimethyl sulfoxide (DMSO) and used in the experiment. 90 mM and 10 mM DMSO stock solutions were prepared from each of the compounds and diluted in an extracellular solution (4 mM KCl, 138 mM NaCl, 1 mM $MgCl_2$, 1.8 mM $CaCl_2$, 5.6 mM Glucose, 10 mM HEPES, pH 7.45) at various concentrations, so that the final concentration of DMSO was 0.3% or less.

3) Measurement of Sodium Ion Channel Blocking Effects

In order to measure the sodium ion channel blocking effect, an IonFlux16 Auto patch clamp system (Fluxion, Inc.) and a plate for exclusive use were used. The cells were distributed in an extracellular solution (4 mM KCl, 138 mM NaCl, 1 mM $MgCl_2$, 1.8 mM $CaCl_2$, 5.6 mM glucose, 10 mM HEPES, pH 7.45), and then dispensed in the specified region of the plate, and each of the prepared compound samples was diluted at various concentrations, and then dispensed in the specified region of the plate. After the dispensation of the cells, the compound samples and an intracellular solution (100 mM CsF, 45 mM CsCl, 5 mM NaCl, 5 mM EGTA, 10 mM HEPES, pH 7.2) in the plate has been completed, the plate was mounted in the patch clamp system, and whether the compounds inhibited the ion channel was measured according to a set program.

Specifically, eight concentrations per compound were set, and percent inhibition was determined by calculating the percentage of inhibition of the peak current, generated after treating the cells with each concentration of the compound for 50 seconds, relative to the peak current generated before treatment with the compound, and the IC50 value was calculated using the Sigma plot program. The results of the calculation are shown in Tables 2 to 5 below.

TABLE 2

| Example | Nav1.7 ($IC_{50}$) |
| --- | --- |
| 1 | 0.035 |
| 2 | 0.026 |
| 3 | 0.103 |
| 4 | 0.044 |
| 5 | 0.120 |
| 6 | 0.182 |
| 7 | 0.125 |
| 8 | 0.489 |
| 9 | 1.505 |
| 10 | 0.396 |
| 11 | 1.007 |
| 12 | 0.412 |
| 13 | 0.372 |
| 14 | 0.447 |

TABLE 2-continued

| Example | Nav1.7 (IC$_{50}$) |
|---|---|
| 15 | 0.369 |
| 16 | 0.108 |
| 17 | 0.053 |
| 18 | >1 |
| 19 | >1 |
| 20 | 0.021 |
| 21 | 0.066 |
| 22 | >1 |
| 23 | 0.357 |
| 24 | 0.049 |
| 25 | n/a |
| 26 | 0.066 |
| 27 | >1 |
| 28 | >0.3 |
| 29 | 0.362 |
| 30 | >1 |
| 31 | 0.044 |
| 32 | 0.017 |
| 33 | >1 |
| 34 | 0.241 |
| 35 | 0.205 |
| 36 | 0.051 |
| 37 | 0.058 |
| 38 | 0.027 |
| 39 | 0.053 |
| 40 | 0.013 |
| 41 | >1 |
| 42 | >1 |
| 43 | >1 |
| 44 | >1 |
| 45 | 0.236 |
| 46 | 0.686 |
| 47 | 0.375 |
| 48 | 0.086 |
| 49 | 0.609 |
| 50 | 0.328 |
| 51 | n/a |
| 52 | 0.061 |
| 53 | >1 |
| 54 | >1 |
| 55 | 0.012 |
| 56 | >1 |
| 57 | >1 |
| 58 | >1 |
| 59 | >1 |
| 60 | 0.073 |
| 61 | >1 |
| 62 | >1 |
| 63 | >10 |
| 64 | 1.174 |
| 65 | 0.541 |
| 66 | 0.160 |
| 67 | 0.028 |
| 68 | 0.103 |
| 69 | 0.241 |
| 70 | 0.050 |
| 71 | 0.435 |
| 72 | 0.046 |
| 73 | 0.100 |
| 74 | 0.278 |
| 75 | 0.126 |
| 76 | 0.149 |
| 77 | 0.032 |
| 78 | 0.212 |
| 79 | 0.216 |
| 80 | 0.028 |

TABLE 3

| Example | Nav1.7 (IC$_{50}$) |
|---|---|
| 81 | 0.023 |
| 82 | |
| 83 | |
| 84 | |
| 85 | |
| 86 | 0.277 |
| 87 | 0.140 |
| 88 | 1.929 |
| 89 | 1.216 |
| 90 | 0.352 |
| 91 | 6.581 |
| 92 | 0.04 |
| 93 | 0.35 |
| 94 | 0.10 |
| 95 | 0.03 |
| 96 | 0.08 |
| 97 | 0.06 |
| 98 | 0.04 |
| 99 | 0.12 |
| 100 | 1.09 |
| 101 | 0.10 |
| 102 | 0.11 |
| 103 | 0.04 |
| 104 | 0.11 |
| 105 | 0.02 |
| 106 | 0.23 |
| 107 | 0.46 |
| 108 | 0.02 |
| 109 | 0.05 |
| 110 | 0.07 |
| 111 | 0.01 |
| 112 | 0.22 |
| 113 | 0.59 |
| 114 | 0.02 |
| 115 | 0.07 |
| 116 | 0.05 |
| 117 | 0.12 |
| 118 | 0.20 |
| 119 | 0.02 |
| 120 | 0.14 |
| 121 | 0.06 |
| 122 | 0.47 |
| 123 | 0.05 |
| 124 | 0.12 |
| 125 | 0.08 |
| 126 | 0.02 |
| 127 | 0.008 |
| 128 | 0.009 |
| 129 | 0.004 |
| 130 | 0.006 |
| 131 | 0.027 |
| 132 | 0.184 |
| 133 | 0.67 |
| 134 | 0.02 |
| 135 | 0.24 |
| 136 | >10 |
| 137 | 0.30 |
| 138 | 0.24 |
| 139 | 0.06 |
| 140 | 3.67 |
| 141 | 0.05 |
| 142 | 0.36 |
| 143 | 0.19 |
| 144 | >10 |
| 145 | 1.40 |
| 146 | 0.39 |
| 147 | 0.25 |
| 148 | 0.11 |
| 149 | 0.30 |
| 150 | 0.36 |
| 151 | >10 |
| 152 | |
| 153 | |
| 154 | |

TABLE 4

| Example | Nav1.5(IC$_{50}$) |
|---|---|
| 1 | >10 |
| 2 | >10 |
| 3 | 6.723 |
| 9 | >10 |
| 10 | >10 |
| 21 | >3 |
| 24 | >10 |
| 26 | >10 |
| 32 | >10 |
| 36 | >10 |
| 37 | >10 |
| 39 | >10 |
| 40 | >10 |
| 48 | >10 |
| 52 | >10 |
| 55 | >10 |
| 67 | >10 |

TABLE 5

| Example | Nav1.5(IC$_{50}$) |
|---|---|
| 92 | 25.03 |
| 95 | 8.2 |
| 96 | >10 |
| 97 | >10 |
| 98 | >10 |
| 99 | >10 |
| 100 | >10 |
| 101 | >10 |
| 102 | >10 |
| 103 | >10 |
| 104 | >10 |
| 105 | >10 |
| 106 | >10 |
| 127 | 5.54 |
| 128 | 1.83 |
| 148 | >10 |
| 149 | >10 |
| 150 | >10 |
| 151 | >10 |

The invention claimed is:

1. A compound represented by Chemical Formula 1:

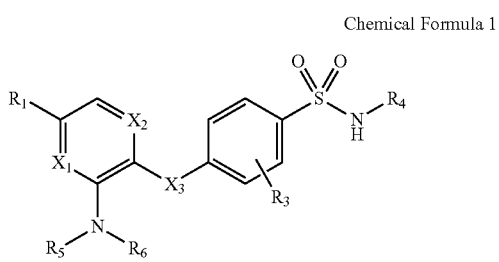

Chemical Formula 1 or a pharmaceutically acceptable salt thereof, wherein:

$R_1$ is hydrogen, $C_{1-4}$ alkyl, $C_{1-4}$ alkoxy, $C_{1-4}$ haloalkyl, $C_{1-4}$ haloalkoxy, halogen or cyano;

$R_2$ is hydrogen or halogen;

$R_3$ is hydrogen or halogen;

$R_4$ is $C_{2-10}$ heteroaryl, wherein the $C_{2-10}$ heteroaryl contains 1 or 2 heteroatoms independently selected from the group consisting of nitrogen, sulfur and oxygen and further wherein the $C_{2-10}$ heteroaryl is optionally substituted with $C_{1-4}$ alkyl or halogen;

$R_5$ is —(CH$_2$)$_2$N(R$_7$)(R$_8$) or —(CH$_2$)$_3$N(R$_7$)(R$_8$);

$R_6$ is hydrogen or $C_{1-4}$ alkyl; or $R_5$ and $R_6$, together form $C_{3-5}$ alkylene, ($C_{2-4}$ alkylene)-N(R$_9$)—($C_{2-4}$ alkylene) or ($C_{2-4}$ alkylene)-O—($C_{2-4}$ alkylene), wherein the $C_{3-5}$ alkylene or each $C_{2-4}$ alkylene is independently and optionally substituted with 1 or 2 R$_{10}$;

$R_7$ is hydrogen or $C_{1-4}$ alkyl;

$R_8$ is hydrogen or $C_{1-4}$ alkyl;

$R_9$ is hydrogen or $C_{1-4}$ alkyl;

$R_{10}$ is $C_{1-4}$ alkyl, $C_{1-4}$ alkoxy, halogen, NH$_2$, NH($C_{1-4}$ alkyl), N($C_{1-4}$ alkyl)$_2$, NHCO($C_{1-4}$ alkyl) or pyrrolidinyl;

R' is hydrogen or halogen;

R" is hydrogen or $C_{1-4}$ alkyl;

$X_1$ is CR' or N;

$X_2$ is CH or N; and $X_3$ is NR".

2. The compound according to claim 1, wherein the compound is represented by Chemical Formula 1':

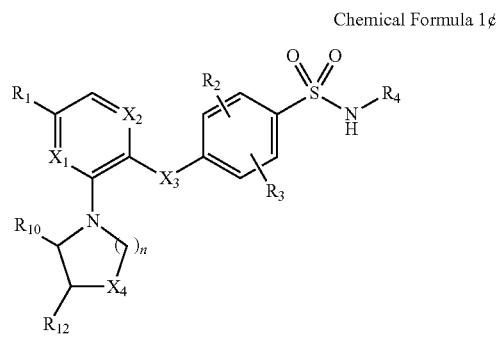

Chemical Formula 1' or a pharmaceutically acceptable salt thereof, wherein:

n is 1, 2, 3 or 4;

$R_{11}$ is hydrogen or $C_{1-4}$ alkyl;

$R_{12}$ is hydrogen $C_{1-4}$ alkyl, $C_{1-4}$ alkoxy, halogen, NH$_2$, NH($C_{1-4}$ alkyl), N($C_{1-4}$ alkyl)$_2$, NHCO($C_{1-4}$ alkyl) or pyrrolidinyl; and $X_4$ is a bond, NH, N($C_{1-4}$ alkyl) or O.

3. The compound according to claim 2, or a pharmaceutically acceptable salt thereof, wherein:

$R_1$ is hydrogen, methyl, methoxy, trifluoromethyl, trifluoromethoxy, difluoromethoxy, fluoro, chloro or cyano.

4. The compound according to claim 2, or a pharmaceutically acceptable salt thereof, wherein:

$R_2$ is hydrogen, fluoro or chloro; and $R_3$ is hydrogen, fluoro or chloro.

5. The compound according to claim 2, or a pharmaceutically acceptable salt thereof, wherein:

$R_4$ is thiadiazolyl, thiazolyl, isoxazolyl, oxazolyl, pyrazolyl, pyridinyl, pyrimidinyl or pyrazinyl, each optionally substituted.

6. The compound according to claim 2, or a pharmaceutically acceptable salt thereof, wherein:

$X_1$ is CH, CF or N; and $X_2$ is CH or N;

provided that both $X_1$ and $X_2$ are not N.

7. The compound according to claim 2, or a pharmaceutically acceptable salt thereof, wherein:

$X_3$ is NH.

8. The compound according to claim 1, or a pharmaceutically acceptable salt thereof, wherein:
$R_1$ is hydrogen, methyl, methoxy, trifluoromethyl, trifluoromethoxy, difluoromethoxy, fluoro, chloro or cyano.

9. The compound according to claim 1, or a pharmaceutically acceptable salt thereof, wherein:
$R_2$ is hydrogen, fluoro or chloro; and
$R_3$ is hydrogen, fluoro or chloro.

10. The compound according to claim 1, or a pharmaceutically acceptable salt thereof, wherein:
$R_4$ is thiadiazolyl, thiazolyl, isoxazolyl, oxazolyl, pyrazolyl, pyridinyl, pyrimidinyl or pyrazinyl, each optionally substituted.

11. The compound according to claim 1, or a pharmaceutically acceptable salt thereof, wherein:
$R_5$ is —$(CH_2)_2N(H)(CH_3)$, —$(CH_2)_2N(CH_3)_2$ or —$(CH_2)_3N(H)(CH_3)$; and
$R_6$ is hydrogen or methyl.

12. The compound according to claim 1, or a pharmaceutically acceptable salt thereof, wherein:
$R_5$ and $R_6$, together form $C_{3-5}$ alkylene, ($C_{2-4}$ alkylene)-$N(R^9)$—($C_{2-4}$ alkylene) or ($C_{2-4}$ alkylene)-O—($C_{2-4}$ alkylene), wherein the $C_{3-5}$ alkylene or each $C_{2-4}$ alkylene is independently and optionally substituted with 1 or 2 methyl, methoxy, fluoro, $NH_2$, $NH(CH_3)$, $N(CH_3)_2$, $N(CH_2CH_3)_2$, $NHCO(CH_3)$ or pyrrolidinyl.

13. The compound according to claim 1, or a pharmaceutically acceptable salt thereof, wherein:
$R_5$ and $R_6$, together with the nitrogen atom to which they are attached, form a heterocyclic ring selected from the group consisting of:

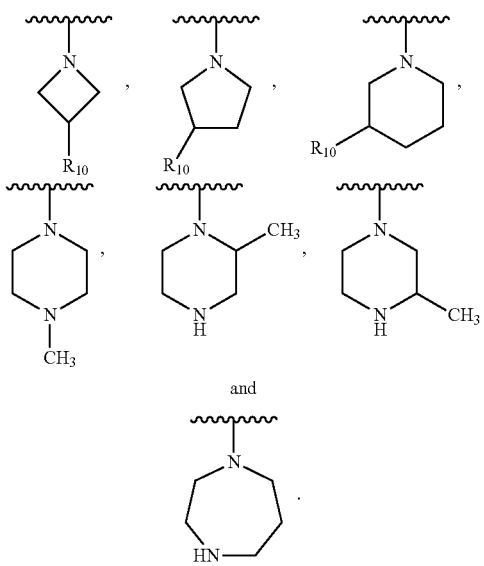

14. The compound according to claim 1, or a pharmaceutically acceptable salt thereof, wherein:
$X_1$ is CH, CF or N; and
$X_2$ is CH or N;
provided that both $X_1$ and $X_2$ are not N.

15. The compound according to claim 1, or a pharmaceutically acceptable salt thereof, wherein:
$X_3$ is NH.

16. The compound according to claim 1, or a pharmaceutically acceptable salt thereof, wherein the compound is selected from the group consisting of:
1) 5-chloro-2-fluoro-4-((4-fluoro-2-(3-(methylamino)pyrrolidin-1-yl)phenyl)amino)-N-(thiazol-4-yl)benzenesulfonamide,
2) 5-chloro-4-((4-chloro-2-(3-(methylamino)pyrrolidin-1-yl)phenyl)amino)-2-fluoro-N-(thiazol-4-yl)benzenesulfonamide,
3) (R)-5-chloro-4-((4-chloro-2-(2-methylpiperazin-1-yl)phenyl)amino)-2-fluoro-N-(thiazol-4-yl)benzenesulfonamide,
4) (R)-5-chloro-4-((4-chloro-2-(3-(methylamino)piperidin-1-yl)phenyl)amino)-2-fluoro-N-(thiazol-4-yl)benzenesulfonamide,
5) (R)—N-(1-(5-chloro-2-((2-chloro-5-fluoro-4-(N-(thiazol-4-yl)sulfamoyl)phenyl)amino)phenyl)pyrrolidin-3-yl)acetamide,
6) 5-chloro-4-((4-chloro-2-(3-(diethylamino)pyrrolidin-1-yl)phenyl)amino)-2-fluoro-N-(thiazol-4-yl)benzenesulfonamide,
7) 4-((2-([1,3'-bipyrrolidin]-1'-yl)-4-chlorophenyl)amino)-5-chloro-2-fluoro-N-(thiazol-4-yl)benzenesulfonamide,
8) 5-chloro-2-fluoro-4-((4-methyl-2-(3-(methylamino)pyrrolidin-1-yl)phenyl)amino)-N-(thiazol-4-yl)benzenesulfonamide,
9) (S)-5-chloro-4-((4-chloro-2-(3-methylpiperazin-1-yl)phenyl)amino)-2-fluoro-N-(thiazol-4-yl)benzenesulfonamide,
10) 4-((4-fluoro-2-(3-(methylamino)pyrrolidin-1-yl)phenyl)amino)-N-(thiazol-4-yl)benzenesulfonamide,
11) 3-chloro-4-((4-fluoro-2-(3-(methylamino)pyrrolidin-1-yl)phenyl)amino)-N-(thiazol-4-yl)benzenesulfonamide,
12) 3,5-difluoro-4-((4-fluoro-2-(3-(methylamino)pyrrolidin-1-yl)phenyl)amino)-N-(thiazol-4-yl)benzenesulfonamide,
13) 2-fluoro-4-((4-fluoro-2-(3-(methylamino)pyrrolidin-1-yl)phenyl)amino)-N-(thiazol-4-yl)benzenesulfonamide,
14) 4-((2-(3-(methylamino)pyrrolidin-1-yl)-4-(trifluoromethoxy)phenyl)amino)-N-(thiazol-4-yl)benzenesulfonamide,
15) 3,5-difluoro-4-((2-(3-(methylamino)pyrrolidin-1-yl)-4-(trifluoromethoxy)phenyl)amino)-N-(thiazol-4-yl)benzenesulfonamide,
16) 2-fluoro-4-((2-(3-(methylamino)pyrrolidin-1-yl)-4-(trifluoromethoxy)phenyl)amino)-N-(thiazol-4-yl)benzenesulfonamide,
17) 5-chloro-2-fluoro-4-((2-(3-(methylamino)pyrrolidin-1-yl)-4-(trifluoromethoxy)phenyl)amino)-N-(thiazol-4-yl)benzenesulfonamide,
18) 5-chloro-4-((5-chloro-3-(3-(methylamino)pyrrolidin-1-yl)pyridin-2-yl)amino)-2-fluoro-N-(thiazol-4-yl)benzenesulfonamide,
19) 5-chloro-4-((6-chloro-2-(3-(methylamino)pyrrolidin-1-yl)pyridin-3-yl)amino)-2-fluoro-N-(thiazol-4-yl)benzenesulfonamide,
20) 5-chloro-2-fluoro-4-((2-(3-(methylamino)pyrrolidin-1-yl)-4-(trifluoromethyl)phenyl)amino)-N-(thiazol-4-yl)benzenesulfonamide,
21) 5-chloro-4-((4-(difluoromethoxy)-2-(3-(methylamino)pyrrolidin-1-yl)phenyl)amino)-2-fluoro-N-(thiazol-4-yl)benzenesulfonamide,
22) (R)-4-((4-fluoro-2-(3-(methylamino)piperidin-1-yl)phenyl)amino)-N-(thiazol-4-yl)benzenesulfonamide, 23) (R)-2-fluoro-4-((4-fluoro-2-(3-(methylamino)piperidin-1-yl)phenyl)amino)-N-(thiazol-4-yl)benzenesulfonamide,
24) (R)-3-chloro-4-((4-fluoro-2-(3-(methylamino)piperidin-1-yl)phenyl)amino)-N-(thiazol-4-yl)benzenesulfonamide,
25) (R)-3,5-difluoro-4-((4-fluoro-2-(3-(methylamino)piperidin-1-yl)phenyl)amino)-N-(thiazol-4-yl)benzenesulfonamide,
26) (R)-5-chloro-2-fluoro-4-((4-fluoro-2-(3-(methylamino)piperidin-1-yl)phenyl)amino)-N-(thiazol-4-yl)benzenesulfonamide,
27) (R)-4-((4-fluoro-2-(3-(methylamino)pyrrolidin-1-yl)phenyl)amino)-N-(thiazol-4-yl)benzenesulfonamide,
28) (R)-2-fluoro-4-((4-fluoro-2-(3-(methylamino)pyrrolidin-1-yl)phenyl)amino)-N-(thiazol-4-yl)benzenesulfonamide,
29) (R)-3-chloro-4-((4-fluoro-2-(3-(methylamino)pyrrolidin-1-yl)phenyl)amino)-N-(thiazol-4-yl)benzenesulfonamide,
30) (R)-3,5-difluoro-4-((4-fluoro-2-(3-(methylamino)pyrrolidin-1-yl)phenyl)amino)-N-(thiazol-4-yl)benzenesulfonamide,
31) (R)-5-chloro-2-fluoro-4-((4-fluoro-2-(3-(methylamino)pyrrolidin-1-yl)phenyl)amino)-N-(thiazol-4-yl)benzenesulfonamide,
32) 5-chloro-2-fluoro-4-((4-fluoro-2-(3-(methylamino)pyrrolidin-1-yl)phenyl)amino)-N-(thiazol-4-yl)benzenesulfonamide,
33) 4-((2-(3-aminopyrrolidin-1-yl)-4-fluorophenyl)amino)-2-fluoro-N-(thiazol-4-yl)benzenesulfonamide,
34) 4-((2-(3-aminopyrrolidin-1-yl)-4-fluorophenyl)amino)-3-chloro-N-(thiazol-4-yl)benzenesulfonamide,
35) 4-((2-(3-aminopyrrolidin-1-yl)-4-fluorophenyl)amino)-5-chloro-2-fluoro-N-(thiazol-4-yl)benzenesulfonamide,
36) 4-((2-(3-(methylamino)pyrrolidin-1-yl)phenyl)amino)-N-(thiazol-4-yl)benzenesulfonamide,
37) 2-fluoro-4-((2-(3-(methylamino)pyrrolidin-1-yl)-4-(trifluoromethyl)phenyl)amino)-N-(thiazol-4-yl)benzenesulfonamide,
38) 3-chloro-4-((2-(3-(methylamino)pyrrolidin-1-yl)-4-(trifluoromethyl)phenyl)amino)-N-(thiazol-4-yl)benzenesulfonamide,
39) 4-((4-(difluoromethoxy)-2-(3-(methylamino)pyrrolidin-1-yl)phenyl)amino)-2-fluoro-N-(thiazol-4-yl)benzenesulfonamide,
40) 3-chloro-4-((4-(difluoromethoxy)-2-(3-(methylamino)pyrrolidin-1-yl)phenyl)amino)-N-(thiazol-4-yl)benzenesulfonamide,
41) (R)-4-((4-fluoro-2-(3-fluoropyrrolidin-1-yl)phenyl)amino)-N-(thiazol-4-yl)benzenesulfonamide,
42) (R)-2-fluoro-4-((4-fluoro-2-(3-fluoropyrrolidin-1-yl)phenyl)amino)-N-(thiazol-4-yl)benzenesulfonamide,
43) (R)-3-chloro-4-((4-fluoro-2-(3-fluoropyrrolidin-1-yl)phenyl)amino)-N-(thiazol-4-yl)benzenesulfonamide,
44) (R)-3,5-difluoro-4-((4-fluoro-2-(3-fluoropyrrolidin-1-yl)phenyl)amino)-N-(thiazol-4-yl)benzenesulfonamide,
45) (R)-5-chloro-2-fluoro-4-((4-fluoro-2-(3-fluoropyrrolidin-1-yl)phenyl)amino)-N-(thiazol-4-yl)benzenesulfonamide,
46) 2-fluoro-4-((3-fluoro-2-(3-(methylamino)pyrrolidin-1-yl)phenyl)amino)-N-(thiazol-4-yl)benzenesulfonamide,
47) 3-chloro-4-((3-fluoro-2-(3-(methylamino)pyrrolidin-1-yl)phenyl)amino)-N-(thiazol-4-yl)benzenesulfonamide,
48) 5-chloro-2-fluoro-4-((3-fluoro-2-(3-(methylamino)pyrrolidin-1-yl)phenyl)amino)-N-(thiazol-4-yl)benzenesulfonamide,
49) 2-fluoro-4-((2-(3-(methylamino)pyrrolidin-1-yl)phenyl)amino)-N-(thiazol-4-yl)benzenesulfonamide,
50) 3-chloro-4-((2-(3-(methylamino)pyrrolidin-1-yl)phenyl)amino)-N-(thiazol-4-yl)benzenesulfonamide,
51) 3,5-difluoro-4-((2-(3-(methylamino)pyrrolidin-1-yl)phenyl)amino)-N-(thiazol-4-yl)benzenesulfonamide,
52) 5-chloro-2-fluoro-4-((2-(3-(methylamino)pyrrolidin-1-yl)phenyl)amino)-N-(thiazol-4-yl)benzenesulfonamide,
53) 2-fluoro-4-((4-methoxy-2-(3-(methylamino)pyrrolidin-1-yl)phenyl)amino)-N-(thiazol-4-yl)benzenesulfonamide,
54) 3-chloro-4-((4-methoxy-2-(3-(methylamino)pyrrolidin-1-yl)phenyl)amino)-N-(thiazol-4-yl)benzenesulfonamide,
55) 5-chloro-2-fluoro-4-((4-methoxy-2-(3-(methylamino)pyrrolidin-1-yl)phenyl)amino)-N-(thiazol-4-yl)benzenesulfonamide,
56) (R)-4-((4-methoxy-2-(3-(methylamino)piperidin-1-yl)phenyl)amino)-N-(thiazol-4-yl)benzenesulfonamide,
57) (R)-2-fluoro-4-((4-methoxy-2-(3-(methylamino)piperidin-1-yl)phenyl)amino)-N-(thiazol-4-yl)benzenesulfonamide,
58) (R)-3-chloro-4-((4-methoxy-2-(3-(methylamino)piperidin-1-yl)phenyl)amino)-N-(thiazol-4-yl)benzenesulfonamide,
59) (R)-3,5-difluoro-4-((4-methoxy-2-(3-(methylamino)piperidin-1-yl)phenyl)amino)-N-(thiazol-4-yl)benzenesulfonamide,
60) (R)-5-chloro-2-fluoro-4-((4-methoxy-2-(3-(methylamino)piperidin-1-yl)phenyl)amino)-N-(thiazol-4-yl)benzenesulfonamide,
61) 3-chloro-4-((4-fluoro-2-(4-methylpiperazin-1-yl)phenyl)amino)-N-(thiazol-4-yl)benzenesulfonamide,
62) 5-chloro-2-fluoro-4-((4-fluoro-2-(4-methylpiperazin-1-yl)phenyl)amino)-N-(thiazol-4-yl)benzenesulfonamide,
63) (S)-5-chloro-4-((2-(3-(dimethylamino)pyrrolidin-1-yl)-4-fluorophenyl)amino)-2-fluoro-N-(thiazol-4-yl)benzenesulfonamide,
64) (S)-5-chloro-4-((2-(3-(dimethylamino)pyrrolidin-1-yl)-4-(trifluoromethyl)phenyl)amino)-2-fluoro-N-(thiazol-4-yl)benzenesulfonamide,
65) 5-chloro-2-fluoro-4-((2-(4-methylpiperazin-1-yl)-4-(trifluoromethyl)phenyl)amino)-N-(thiazol-4-yl)benzenesulfonamide,
66) 5-chloro-4-((4-(difluoromethoxy)-2-(4-methylpiperazin-1-yl)phenyl)amino)-2-fluoro-N-(thiazol-4-yl)benzenesulfonamide,
67) 5-chloro-2-fluoro-4-((2-(4-methylpiperazin-1-yl)-4-(trifluoromethoxy)phenyl)amino)-N-(thiazol-4-yl)benzenesulfonamide,
68) (S)-3-chloro-4-((2-(3-(dimethylamino)pyrrolidin-1-yl)-4-(trifluoromethyl)phenyl)amino)-N-(thiazol-4-yl)benzenesulfonamide,
69) (S)-2-fluoro-4-((4-fluoro-2-(3-(methylamino)pyrrolidin-1-yl)phenyl)amino)-N-(thiazol-4-yl)benzenesulfonamide, 70) (S)-5-chloro-2-fluoro-4-((4-fluoro-2-(3-(methylamino)pyrrolidin-1-yl)phenyl)amino)-N-(thiazol-4-yl)benzenesulfonamide,
71) (S)-5-chloro-4-((2-(3-(dimethylamino)pyrrolidin-1-yl)-4-methoxyphenyl)amino)-2-fluoro-N-(thiazol-4-yl)benzenesulfonamide,
72) (S)-5-chloro-4-((4-(difluoromethoxy)-2-(3-(dimethylamino)pyrrolidin-1-yl)phenyl)amino)-2-fluoro-N-(thiazol-4-yl)benzenesulfonamide,
73) (R)-5-chloro-4-((2-(3-(dimethylamino)pyrrolidin-1-yl)-4-fluorophenyl)amino)-2-fluoro-N-(thiazol-4-yl)benzenesulfonamide,
74) (R)-5-chloro-4-((2-(3-(dimethylamino)pyrrolidin-1-yl)-4-(trifluoromethyl)phenyl)amino)-2-fluoro-N-(thiazol-4-yl)benzenesulfonamide,
75) (R)-5-chloro-4-((4-(difluoromethoxy)-2-(3-(dimethylamino)pyrrolidin-1-yl)phenyl)amino)-2-fluoro-N-(thiazol-4-yl)benzenesulfonamide,
76) 4-((2-(1,4-diazepan-1-yl)-4-fluorophenyl)amino)-5-chloro-2-fluoro-N-(thiazol-4-yl)benzenesulfonamide,
77) 5-chloro-4-((4-cyano-2-(3-(methylamino)pyrrolidin-1-yl)phenyl)amino)-2-fluoro-N-(thiazol-4-yl)benzenesulfonamide,
78) (R)—N-(1-(2-((2-chloro-5-fluoro-4-(N-(thiazol-4-yl)sulfamoyl)phenyl)amino)-5-(trifluoromethyl)phenyl)pyrrolidin-3-yl)acetamide,
79) (R)—N-(1-(2-((2-chloro-4-(N-(thiazol-4-yl)sulfamoyl)phenyl)amino)-5-(trifluoromethyl)phenyl)pyrrolidin-3-yl)acetamide,
80) (S)-3-chloro-4-((2-(3-(methylamino)pyrrolidin-1-yl)-4-(trifluoromethyl)phenyl)amino)-N-(thiazol-4-yl)benzenesulfonamide,
81) (S)-5-chloro-2-fluoro-4-((2-(3-(methylamino)pyrrolidin-1-yl)-4-(trifluoromethyl)phenyl)amino)-N-(thiazol-4-yl)benzenesulfonamide,
82) 5-chloro-2-fluoro-4-((4-fluoro-2-(3-(methylamino)azetidin-1-yl)phenyl)amino)-N-(thiazol-4-yl)benzenesulfonamide,
83) 4-((2-(3-aminoazetidin-1-yl)-4-fluorophenyl)amino)-5-chloro-2-fluoro-N-(thiazol-4-yl)benzenesulfonamide,
84) 5-chloro-4-((2-(3-(dimethylamino)azetidin-1-yl)-4-fluorophenyl)amino)-2-fluoro-N-(thiazol-4-yl)benzenesulfonamide,
85) N-(1-(2-((2-chloro-5-fluoro-4-(N-(thiazol-4-yl)sulfamoyl)phenyl)amino)-5-fluorophenyl)azetidin-3-yl)acetamide,
86) 5-chloro-2-fluoro-4-((4-fluoro-2-(3-methoxypyrrolidin-1-yl)phenyl)amino)-N-(thiazol-4-yl)benzenesulfonamide,
87) 5-chloro-2-fluoro-4-((2-(3-methoxypyrrolidin-1-yl)-4-(trifluoromethyl)phenyl)amino)-N-(thiazol-4-yl)benzenesulfonamide,
88) (R)—N-(1-(2-((2-chloro-5-fluoro-4-(N-(thiazol-4-yl)sulfamoyl)phenyl)amino)-5-fluorophenyl)pyrrolidin-3-yl)acetamide,
89) 3-chloro-4-((4-fluoro-2-(3-methoxypyrrolidin-1-yl)phenyl)amino)-N-(thiazol-4-yl)benzenesulfonamide,
90) 3-chloro-4-((2-(3-methoxypyrrolidin-1-yl)-4-(trifluoromethyl)phenyl)amino)-N-(thiazol-4-yl)benzenesulfonamide,
91) (R)—N-(1-(2-((2-chloro-4-(N-(thiazol-4-yl)sulfamoyl)phenyl)amino)-5-fluorophenyl)pyrrolidin-3-yl)acetamide,
92) 5-chloro-2-fluoro-4-((4-fluoro-2-(methyl(2-(methylamino)ethyl)amino)phenyl)amino)-N-(thiazol-4-yl)benzenesulfonamide,
93) 3-chloro-4-((2-((2-(dimethylamino)ethyl)(methyl)amino)-4-fluorophenyl)amino)-N-(thiazol-4-yl)benzenesulfonamide,
94) 5-chloro-4-((2-((2-(dimethylamino)ethyl)(methyl)amino)-4-fluorophenyl)amino)-2-fluoro-N-(thiazol-4-yl)benzenesulfonamide,
95) 5-chloro-2-fluoro-4-((2-(methyl(2-(methylamino)ethyl)amino)-4-(trifluoromethyl)phenyl)amino)-N-(thiazol-4-yl)benzenesulfonamide,
96) 5-chloro-2-fluoro-4-((4-fluoro-2-(methyl(2-(methylamino)ethyl)amino)phenyl)amino)-N-(5-fluoropyrimidin-2-yl)benzenesulfonamide,
97) 5-chloro-2-fluoro-N-(5-fluoropyrimidin-2-yl)-4-((2-(methyl(2-(methylamino)ethyl)amino)-4-(trifluoromethyl)phenyl)amino)benzenesulfonamide,
98) 5-chloro-4-((4-(difluoromethoxy)-2-(methyl(2-(methylamino)ethyl)amino)phenyl)amino)-2-fluoro-N-(thiazol-4-yl)benzenesulfonamide,
99) 5-chloro-4-((4-cyano-2-(methyl(2-(methylamino)ethyl)amino)phenyl)amino)-2-fluoro-N-(thiazol-4-yl)benzenesulfonamide,
100) 5-chloro-4-((4-cyano-2-(methyl(2-(methylamino)ethyl)amino)phenyl)amino)-2-fluoro-N-(5-fluoropyrimidin-2-yl)benzenesulfonamide,
101) 5-chloro-4-((4-(difluoromethoxy)-2-(methyl(2-(methylamino)ethyl)amino)phenyl)amino)-2-fluoro-N-(5-fluoropyrimidin-2-yl)benzenesulfonamide,
102) 5-chloro-2-fluoro-N-(5-fluoropyrimidin-2-yl)-4-((2-(methyl(2-(methylamino)ethyl)amino)phenyl)amino)benzenesulfonamide,
103) 5-chloro-2-fluoro-4-((4-fluoro-2-(methyl(2-(methylamino)ethyl)amino)phenyl)amino)-N-(5-fluoropyridin-2-yl)benzenesulfonamide,
104) 5-chloro-2-fluoro-4-((4-fluoro-2-(methyl(2-(methylamino)ethyl)amino)phenyl)amino)-N-(pyridin-2-yl)benzenesulfonamide,
105) 5-chloro-2-fluoro-4-((4-fluoro-2-(methyl(2-(methylamino)ethyl)amino)phenyl)amino)-N-(thiazol-2-yl)benzenesulfonamide,
106) 5-chloro-4-((4-cyano-2-(methyl(2-(methylamino)ethyl)amino)phenyl)amino)-2-fluoro-N-(5-fluoropyridin-2-yl)benzenesulfonamide,
107) 5-chloro-4-((4-cyano-2-(methyl(2-(methylamino)ethyl)amino)phenyl)amino)-2-fluoro-N-(pyridin-2-yl)benzenesulfonamide,
108) 5-chloro-4-((4-cyano-2-(methyl(2-(methylamino)ethyl)amino)phenyl)amino)-2-fluoro-N-(thiazol-2-yl)benzenesulfonamide,
109) 5-chloro-2-fluoro-N-(5-fluoropyridin-2-yl)-4-((2-(methyl(2-(methylamino)ethyl)amino)-4-(trifluoromethyl)phenyl)amino)benzenesulfonamide,
110) 5-chloro-2-fluoro-4-((2-(methyl(2-(methylamino)ethyl)amino)-4-(trifluoromethyl)phenyl)amino)-N-(pyridin-2-yl)benzenesulfonamide,
111) 5-chloro-2-fluoro-4-((2-(methyl(2-(methylamino)ethyl)amino)-4-(trifluoromethyl)phenyl)amino)-N-(thiazol-2-yl)benzenesulfonamide,
112) 5-chloro-2-fluoro-N-(5-fluoropyridin-2-yl)-4-((2-(methyl(2-(methylamino)ethyl)amino)phenyl)amino)benzenesulfonamide,
113) 5-chloro-2-fluoro-4-((2-(methyl(2-(methylamino)ethyl)amino)phenyl)amino)-N-(pyridin-2-yl)benzenesulfonamide,
114) 5-chloro-2-fluoro-4-((2-(methyl(2-(methylamino)ethyl)amino)phenyl)amino)-N-(thiazol-2-yl)benzenesulfonamide, 115) 5-chloro-4-((4-(difluoromethoxy)-2-(methyl(2-(methylamino)ethyl)amino)phenyl)amino)-2-fluoro-N-(5-fluoropyridin-2-yl)benzenesulfonamide,
116) 5-chloro-4-((4-(difluoromethoxy)-2-(methyl(2-(methylamino)ethyl)amino)phenyl)amino)-2-fluoro-N-(thiazol-2-yl)benzenesulfonamide,
117) 5-chloro-4-((4-(difluoromethoxy)-2-(methyl(2-(methylamino)ethyl)amino)phenyl)amino)-2-fluoro-N-(pyridin-2-yl)benzenesulfonamide,
118) 5-chloro-2-fluoro-N-(5-fluoropyridin-2-yl)-4-((4-methoxy-2-(methyl(2-(methylamino)ethyl)amino)phenyl)amino)benzenesulfonamide,
119) 5-chloro-2-fluoro-4-((4-methoxy-2-(methyl(2-(methylamino)ethyl)amino)phenyl)amino)-N-(thiazol-2-yl)benzenesulfonamide,
120) 5-chloro-2-fluoro-4-((4-methoxy-2-(methyl(2-(methylamino)ethyl)amino)phenyl)amino)-N-(thiazol-4-yl)benzenesulfonamide,
121) 5-chloro-2-fluoro-4-((2-(methyl(2-(methylamino)ethyl)amino)phenyl)amino)-N-(thiazol-4-yl)benzenesulfonamide,
122) 5-chloro-2-fluoro-N-(5-fluoropyrimidin-2-yl)-4-((4-methoxy-2-(methyl(2-(methylamino)ethyl)amino)phenyl)amino)benzenesulfonamide,
123) 5-chloro-4-((4-chloro-2-(methyl(2-(methylamino)ethyl)amino)phenyl)amino)-2-fluoro-N-(thiazol-4-yl)benzenesulfonamide,
124) 5-chloro-4-((4-chloro-2-(methyl(2-(methylamino)ethyl)amino)phenyl)amino)-2-fluoro-N-(5-fluoropyrimidin-2-yl)benzenesulfonamide,
125) 5-chloro-4-((4-chloro-2-(methyl(2-(methylamino)ethyl)amino)phenyl)amino)-2-fluoro-N-(5-fluoropyridin-2-yl)benzenesulfonamide,
126) 5-chloro-4-((4-chloro-2-(methyl(2-(methylamino)ethyl)amino)phenyl)amino)-2-fluoro-N-(thiazol-2-yl)benzenesulfonamide,
127) 5-chloro-N-(5-chlorothiazol-2-yl)-2-fluoro-4-((4-fluoro-2-(methyl(2-(methylamino)ethyl)amino)phenyl)amino)benzenesulfonamide,
128) 5-chloro-2-fluoro-4-((4-fluoro-2-(methyl(2-(methylamino)ethyl)amino)phenyl)amino)-N-(5-fluorothiazol-2-yl)benzenesulfonamide,
129) 5-chloro-N-(5-chlorothiazol-2-yl)-2-fluoro-4-((2-(methyl(2-(methylamino)ethyl)amino)phenyl)amino)benzenesulfonamide,
130) 5-chloro-N-(5-chlorothiazol-2-yl)-2-fluoro-4-((4-methoxy-2-(methyl(2-(methylamino)ethyl)amino)phenyl)amino)benzenesulfonamide,
131) 5-chloro-2-fluoro-N-(5-fluorothiazol-2-yl)-4-((2-(methyl(2-(methylamino)ethyl)amino)phenyl)amino)benzenesulfonamide,
132) 5-chloro-2-fluoro-N-(5-fluorothiazol-2-yl)-4-((4-methoxy-2-(methyl(2-(methylamino)ethyl)amino)phenyl)amino)benzenesulfonamide,
133) 5-chloro-2-fluoro-4-((4-fluoro-2-(methyl(2-(methylamino)ethyl)amino)phenyl)amino)-N-(5-methylisoxazol-3-yl)benzenesulfonamide,
134) 5-chloro-2-fluoro-4-((2-(methyl(2-(methylamino)ethyl)amino)phenyl)amino)-N-(5-methylisoxazol-3-yl)benzenesulfonamide,
135) 5-chloro-2-fluoro-4-((4-fluoro-2-(methyl(2-(methylamino)ethyl)amino)phenyl)amino)-N-(5-methyl-1H-pyrazol-3-yl)benzenesulfonamide,
136) 5-chloro-2-fluoro-4-((2-(methyl(2-(methylamino)ethyl)amino)phenyl)amino)-N-(5-methyl-1H-pyrazol-3-yl)benzenesulfonamide,
137) 5-chloro-4-((2-((2-(dimethylamino)ethyl)(methyl)amino)-4-fluorophenyl)amino)-2-fluoro-N-(5-fluoropyridin-2-yl)benzenesulfonamide,
138) 5-chloro-4-((2-((2-(dimethylamino)ethyl)(methyl)amino)-4-fluorophenyl)amino)-2-fluoro-N-(thiazol-2-yl)benzenesulfonamide,
139) 5-chloro-N-(5-chlorothiazol-2-yl)-4-((2-((2-(dimethylamino)ethyl)(methyl)amino)-4-fluorophenyl)amino)-2-fluorobenzenesulfonamide,
140) 5-chloro-N-(5-chlorothiazol-2-yl)-4-((2-((2-(dimethylamino)ethyl)(methyl)amino)phenyl)amino)-2-fluorobenzenesulfonamide,
141) 5-chloro-2-fluoro-4-((4-fluoro-2-(methyl(2-(methylamino)ethyl)amino)phenyl)amino)-N-(5-methylthiazol-2-yl)benzenesulfonamide,
142) 5-chloro-2-fluoro-4-((4-fluoro-2-(methyl(2-(methylamino)ethyl)amino)phenyl)amino)-N-(oxazol-2-yl)benzenesulfonamide,
143) N-(5-(tert-butyl)isoxazol-3-yl)-5-chloro-2-fluoro-4-((4-fluoro-2-(methyl(2-(methylamino)ethyl)amino)phenyl)amino)benzenesulfonamide,
144) N-(5-(tert-butyl)isoxazol-3-yl)-5-chloro-2-fluoro-4-((2-(methyl(2-(methylamino)ethyl)amino)phenyl)amino)benzenesulfonamide,
145) 5-chloro-2-fluoro-4-((4-fluoro-2-(3-(methylamino)pyrrolidin-1-yl)phenyl)amino)-N-(1,2,4-thiadiazol-5-yl)benzenesulfonamide,
146) 5-chloro-2-fluoro-4-((4-fluoro-2-(3-(methylamino)pyrrolidin-1-yl)phenyl)amino)-N-(1-methyl-1H-pyrazol-3-yl)benzenesulfonamide,
147) 5-chloro-2-fluoro-4-((4-fluoro-2-(3-(methylamino)pyrrolidin-1-yl)phenyl)amino)-N-(pyrimidin-4-yl)benzenesulfonamide,
148) 5-chloro-2-fluoro-4-((4-fluoro-2-(3-(methylamino)pyrrolidin-1-yl)phenyl)amino)-N-(5-fluoropyrimidin-2-yl)benzenesulfonamide,
149) 5-chloro-2-fluoro-4-((4-fluoro-2-(3-(methylamino)pyrrolidin-1-yl)phenyl)amino)-N-(pyrazin-2-yl)benzenesulfonamide,
150) 5-chloro-2-fluoro-4-((4-fluoro-2-(3-(methylamino)pyrrolidin-1-yl)phenyl)amino)-N-(5-methylisoxazol-3-yl)benzenesulfonamide,
151) 5-chloro-2-fluoro-4-((4-fluoro-2-(3-(methylamino)pyrrolidin-1-yl)phenyl)amino)-N-(pyrimidin-5-yl)benzenesulfonamide,
152) 5-chloro-2-fluoro-4-((4-fluoro-2-((2-(methylamino)ethyl)amino)phenyl)amino)-N-(thiazol-4-yl)benzenesulfonamide,
153) 5-chloro-4-((2-((2-(dimethylamino)ethyl)amino)-4-fluorophenyl)amino)-2-fluoro-N-(thiazol-4-yl)benzenesulfonamide, and
154) 5-chloro-2-fluoro-4-((4-fluoro-2-(methyl(3-(methylamino)propyl)amino)phenyl)amino)-N-(thiazol-4-yl)benzenesulfonamide.

17. A pharmaceutical composition comprising the compound according to claim 1, or a pharmaceutically acceptable salt thereof, as an active ingredient and a pharmaceutically acceptable carrier.

18. A method for inhibiting a voltage-gated sodium channel in a patient, comprising administering to the patient in need thereof a pharmaceutical composition according to claim 17.

19. The method according to claim 18, wherein the patient has a sodium channel blocker-related disease.

20. The method according to claim 19, wherein the sodium channel blocker-related disease is a neuropathic disease.

21. The method according to claim 19, wherein the sodium channel blocker-related disease is selected from the group consisting of acute pain, chronic pain, neuropathic pain, postoperative pain, visceral pain, nerve damage, migraine, epilepsy, depression, anthralgia, erythralgia, arrhythmia, myotonia, ataxia, neuropathy, multiple sclerosis, irritable bowel syndrome, urinary incontinence and paroxysmal extreme pain disorder.

22. The method according to claim 21, wherein the neuropathy is diabetic neuropathy.

* * * * *